US012760087B2

(12) United States Patent
Wang et al.

(10) Patent No.: US 12,760,087 B2
(45) Date of Patent: Oct. 13, 2026

(54) MODIFIED T CELL, PREPARATION METHOD THEREFOR AND USE THEREOF

(71) Applicant: Institute of Zoology, Chinese Academy of Sciences, Beijing (CN)

(72) Inventors: Haoyi Wang, Beijing (CN); Xingying Zhang, Beijing (CN); Chen Cheng, Beijing (CN); Na Tang, Beijing (CN); Na Li, Beijing (CN)

(73) Assignee: Institute of Zoology, Chinese Academy of Sciences, Beijing (CN)

( * ) Notice: Subject to any disclaimer, the term of this patent is extended or adjusted under 35 U.S.C. 154(b) by 1319 days.

(21) Appl. No.: 17/277,274

(22) PCT Filed: Sep. 17, 2019

(86) PCT No.: PCT/CN2019/106109

§ 371 (c)(1),
(2) Date: Sep. 20, 2021

(87) PCT Pub. No.: WO2020/057486

PCT Pub. Date: Mar. 26, 2020

(65) Prior Publication Data

US 2022/0008464 A1 Jan. 13, 2022

(30) Foreign Application Priority Data

Sep. 17, 2018 (CN) ......................... 201811080440.7

(51) Int. Cl.

| | |
|---|---|
| ***C07K 14/705*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***C07K 14/715*** | (2006.01) |
| ***C07K 16/30*** | (2006.01) |
| ***C12N 5/0783*** | (2010.01) |

(52) U.S. Cl.

CPC ........ *C07K 14/70575* (2013.01); *A61K 40/11* (2025.01); *A61K 40/31* (2025.01); *A61K 40/4255* (2025.01); *A61P 35/00* (2018.01); *C07K 14/70578* (2013.01); *C07K 14/70596* (2013.01); *C07K 14/7155* (2013.01); *C07K 16/30* (2013.01); *C12N 5/0636* (2013.01); *A61K 2239/59* (2023.05)

(58) Field of Classification Search

None

See application file for complete search history.

(56) References Cited

U.S. PATENT DOCUMENTS

| | | | | |
|---|---|---|---|---|
| 2014/0301993 | A1* | 10/2014 | Powell, Jr. | A61K 39/4631 435/328 |
| 2019/0183932 | A1* | 6/2019 | Mackall | A61K 35/17 |
| 2019/0185860 | A1* | 6/2019 | Kim | C12N 15/63 |
| 2019/0321404 | A1 | 10/2019 | Fan et al. | |
| 2023/0061455 | A1* | 3/2023 | Burleigh | A61K 39/464417 |

FOREIGN PATENT DOCUMENTS

| | | | |
|---|---|---|---|
| CN | 107523545 | A | 12/2017 |
| CN | 107523547 | A | 12/2017 |
| CN | 108276493 | A | 7/2018 |
| EP | 3338800 | A1 | 6/2018 |
| WO | 201768349 | A1 | 4/2017 |
| WO | 2018107058 | A1 | 6/2018 |

* cited by examiner

*Primary Examiner* — Christopher M Babic
*Assistant Examiner* — Alyssa G Weston
(74) *Attorney, Agent, or Firm* — Mintz Levin Cohn Ferris Glovsky and Popeo, P.C.

(57) ABSTRACT

The present invention relates to the field of gene editing and tumor immunotherapy. In particular, the invention relates to methods for preparing modified T cells, such as CAR-T cells, by gene editing, and modified T cells prepared by the methods and uses thereof.

9 Claims, 45 Drawing Sheets

Specification includes a Sequence Listing.

A

B

| | sgRNA-1 | sgRNA-4 | sgRNA-5 | sgRNA-8 |
|---|---|---|---|---|
| **Target sequence** | TGCTGGCG ATACGCGT CCAC | CCATGGGTC GGGGCTG CTC | CGAGCAGC GGGGTCTG CCAT | CCTGAGC AGCCCCC GACCCA |
| KO efficiency | 27.0% | 13.6% | 28.0% | 64.0% |
| **TIDE (F/R)** | 11.0/10.6% | 9.0/8.3% | 19.0/21.0% | 62.0/57.0% |

B

| | sg8-1 | sg8-2 |
|---|---|---|
| KO efficiency | 83.39% | 81.56% |
| TIDE (F/R) | 91.7/94.6% | 90.8/93.6% |

B

A

B

MODIFIED T CELL, PREPARATION METHOD THEREFOR AND USE THEREOF

RELATED APPLICATIONS

This application is a U.S. national phase application, pursuant to 35 U.S.C. § 371, of PCT/CN2019/106109 filed Sep. 17, 2019 designating the United States, which claims priority to Chinese Patent Application No. 201811080440.7 filed Sep. 17, 2018. The entire contents of the aforementioned patent applications are incorporated herein by this reference.

INCORPORATION-BY-REFERENCE OF SEQUENCE LISTING

The instant application contains a Sequence Listing which has been submitted electronically in ASCII format and is hereby incorporated by reference in its entirety. Said ASCII copy, created on Apr. 13, 2021 is named NP2021TC724_seq.txt and is 16,384 bytes in size.

TECHNICAL FIELD

The present invention relates to the field of gene editing and tumor immunotherapy. In particular, the invention relates to methods for preparing modified T cells, such as CAR-T cells, by gene editing, and modified T cells prepared by the methods and uses thereof.

BACKGROUND

T cells play an important role in anti-tumor immunity. However, in patients with tumor, local specific cytotoxic T lymphocyte (CTL) content is very low. It is difficult to obtain and expand CTL in vitro, and the low affinity of CTL limits its application in the clinical treatment of tumors.

Adoptive transfer of T cells is a specific, low-toxicity anti-tumor method that has received high attention in recent years. For example, genetic modification of T cells with T cell receptor (TCR) or chimeric antigen receptor (CAR) is the most commonly-used method to generate tumor-specific T cells.

The TCR gene transfer technology is to clone TCR alpha and beta chains from tumor-reactive T cells, with retrovirus or lentivirus as the carrier using genetic engineering techniques to modify the initial T cells with antigen-specific TCR, thereby enabling T cells to specifically identify and kill tumor cells and increase the affinity of T cells to tumors. TCR gene transfer technologies are used to modify autologous T cells from a patient. After expansion in vitro, a large number of T cells with specific and efficient recognition ability were obtained and adoptive infused back to the patient to exert anti-tumor effect in vivo.

CAR consists of an extracellular domain, a hinge, a transmembrane domain, and an intracellular domain, wherein the extracellular domain is typically derived from a single-chain variable fragment (scFv), and the intracellular domain has one or more costimulatory or signaling domains (Kakarla and Gottschalk, 2014). Although CAR-T cell therapy has been successful in early clinical studies in the treatment of CD19-positive malignant hematologic tumors (Daviala et al, 2014; Lee et al, 2015; Maude et al, 2014), the clinical response to targeting solid tumor antigens with CAR-T cells is limited due to the large heterogeneity of solid tumors, complicated tumor microenvironment, and difficulty for infiltration of CAR-T cells.

Therefore, there is still a need to obtain T cells that are effective in inhibiting or killing tumors, especially solid tumors.

SUMMARY OF THE INVENTION

In one aspect, the invention provides a method for preparing a modified T cell, comprising a step of reducing or eliminating the expression of at least one inhibitory protein in the T cell, wherein the inhibitory protein is a T cell surface inhibitory receptor and/or a T cell exhaustion-related protein, for example, the inhibitory protein is selected from a TGFβ receptor (such as TGFBRII), TIGIT, BTLA, 2B4, CD160, CD200R, A2aR, IL10RA, ADRB2, BATF, GATA3, IRF4, RARA, LAYN, MYO7A, PHLDA1, RGS1, RGS2, SHP1, DGKa, Fas, FasL, or any combination thereof.

In some embodiments, said T cell is a T cell comprising an exogenous T cell receptor (TCR) or a chimeric antigen receptor (CAR).

In some embodiments, said reduction or elimination is achieved by antisense RNA, antagomir, siRNA, shRNA, meganuclease, zinc finger nuclease, transcription activator-like effector nuclease, or CRISPR system.

In some embodiments, said CRISPR system is a CRISPR/Cas9 system.

In some embodiments, said CRISPR/Cas9 system targets one or more of the nucleotide sequences in the cells selected from the group consisting of SEQ ID NOs: 1-21 and 28-31

In some embodiments, the TCR or CAR comprises an antigen binding domain against a tumor associated antigen.

In some embodiments, the tumor associated antigen is selected from the group consisting of CD16, CD64, CD78, CD96, CLL1, CD116, CD117, CD71, CD45, CD71, CD123, CD138, ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD30, CD40, disialylganglioside GD2, ductal epithelial mucin, gp36, TAG-72, glycosphingolipid, glioma-related antigens, β-human chorionic gonadotropin, a-fetoglobulin (AFP), lectin-responsive AFP, thyroglobulin, RAGE-1, MN-CA IX, human telomerase reverse transcriptase, RU1, RU2 (AS), intestinal carboxyl esterase, mut hsp70-2, M-CSF, prostase, prostatase specific antigen (PSA), PAP, NY-ESO-1, LAGA-1a, p53, Prostein, PSMA, survival and telomerase, prostate cancer tumor antigen-1 (PCTA-1), MAGE, ELF2M, neutrophil elastase, ephrin B2, CD22, insulin growth factor (IGF1)-I, IGF-II, IGFI receptor, mesothelin, major histocompatibility complex (MHC) molecules that present tumor-specific peptide epitopes, 5T4, ROR1, Nkp30, NKG2D, tumor stromal antigen, fibronectin extra domain A (EDA) and extra domain B (EDB), tenascin-C Al domain (TnC A1), fibroblast-associated protein (fap), CD3, CD4, CD8, CD24, CD25, CD33, CD34, CD133, CD138, Foxp3, B7-1 (CD80), B7-2 (CD86), GM-CSF, cytokine receptor, endothelial factor, BCMA (CD269, TNFRSF17), TNFRSF17 (UNIPROT Q02223), SLAMF7 (UNIPROT Q9NQ25), GPRC5D (UNIPROT Q9NZD1), FKBP11 (UNIPROT Q9NYL4), KAMP3, ITGA8 (UNIPROT P53708) and FCRL5 (UNIPROT Q68SN8).

In some embodiments, the antigen-binding domain is selected from a monoclonal antibody, a synthetic antibody, a human antibody, a humanized antibody, a single domain antibody, an antibody single-chain variable region, and an antigen-binding fragment thereof.

In some embodiments, the CAR comprises a scFv against mesothelin, a CD8 hinge region, a CD28 transmembrane domain, a CD28 costimulatory domain, and a CD3¢ signal transduction domain.

In some embodiments, the CAR comprises an amino acid sequence set forth in SEQ ID NO: 27.

In another aspect, the present invention provides a modified T cell, which is prepared by the method of the invention.

In another aspect, the present invention provides a modified T cell, wherein the expression of at least one inhibitory protein in the T cell is reduced or eliminated as compared with an unmodified T cell, wherein the inhibitory protein is a T cell surface inhibitory receptor and/or a T cell exhaustion-related protein, for example, the inhibitory protein is selected from a TGFβ receptor (such as TGFBRII), TIGIT, BTLA, 2B4, CD160, CD200R, A2aR, IL10RA, ADRB2, BATF, GATA3, IRF4, RARA, LAYN, MYO7A, PHLDA1, RGS1, RGS2, SHP1, DGKa, Fas, FasL, or any combination thereof.

In some embodiments, said T cell is a T cell comprising an exogenous T cell receptor (TCR) or a chimeric antigen receptor (CAR).

In some embodiments, the TCR or CAR comprises an antigen binding domain against a tumor associated antigen.

In some embodiments, the tumor associated antigen is selected from the group consisting of CD16, CD64, CD78, CD96, CLL1, CD116, CD117, CD71, CD45, CD71, CD123, CD138, ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD30, CD40, disialylganglioside GD2, ductal epithelial mucin, gp36, TAG-72, glycosphingolipid, glioma-related antigens, β-human chorionic gonadotropin, a-fetoglobulin (AFP), lectin-responsive AFP, thyroglobulin, RAGE-1, MN-CA IX, human telomerase reverse transcriptase, RU1, RU2 (AS), intestinal carboxyl esterase, mut hsp70-2, M-CSF, prostase, prostatase specific antigen (PSA), PAP, NY-ESO-1, LAGA-1a, p53, Prostein, PSMA, survival and telomerase, prostate cancer tumor antigen-1 (PCTA-1), MAGE, ELF2M, neutrophil elastase, ephrin B2, CD22, insulin growth factor (IGF1)-I, IGF-II, IGFI receptor, mesothelin, major histocompatibility complex (MHC) molecules that present tumor-specific peptide epitopes, 5T4, ROR1, Nkp30, NKG2D, tumor stromal antigen, fibronectin extra domain A (EDA) and extra domain B (EDB), tenascin-C Al domain (TnC A1), fibroblast-associated protein (fap), CD3, CD4, CD8, CD24, CD25, CD33, CD34, CD133, CD138, Foxp3, B7-1 (CD80), B7-2 (CD86), GM-CSF, cytokine receptor, endothelial factor, BCMA (CD269, TNFRSF17), TNFRSF17 (UNIPROT Q02223), SLAMF7 (UNIPROT Q9NQ25), GPRC5D (UNIPROT Q9NZD1), FKBP11 (UNIPROT Q9NYL4), KAMP3, ITGA8 (UNIPROT P53708) and FCRL5 (UNIPROT Q68SN8).

In some embodiments, wherein the antigen-binding domain is selected from a monoclonal antibody, a synthetic antibody, a human antibody, a humanized antibody, a single domain antibody, an antibody single-chain variable region, and an antigen-binding fragment thereof.

In some embodiments, wherein the CAR comprises a scFv against mesothelin, a CD8 hinge region, a CD28 transmembrane domain, a CD28 costimulatory domain, and a CD32 signal transduction domain.

In some embodiments, the CAR comprises an amino acid sequence set forth in SEQ ID NO: 27.

In another aspect, the present invention provides use of the modified T cell of the invention in the manufacture of a medicament for treatment of cancer.

In another aspect, the present invention provides a pharmaceutical composition for treating cancer comprising the modified T cell of the invention and a pharmaceutically acceptable carrier.

In embodiments of various aspects of the invention, the cancer is selected from the group consisting of lung cancer, ovarian cancer, colon cancer, rectal cancer, melanoma, kidney cancer, bladder cancer, breast cancer, liver cancer, lymphoma, hematological malignancies, head and neck cancers, glial tumor, stomach cancer, nasopharyngeal cancer, throat cancer, cervical cancer, uterine body tumor and osteosarcoma. Examples of other cancers that can be treated with the method or pharmaceutical composition of the present invention include: bone cancer, pancreatic cancer, skin cancer, prostate cancer, skin or intraocular malignant melanoma, uterine cancer, anal cancer, testicular cancer, fallopian tube cancer, endometrial cancer, vaginal cancer, vaginal cancer, Hodgkin's disease, non-Hodgkin's lymphoma, esophageal cancer, small intestine cancer, endocrine system cancer, thyroid cancer, parathyroid cancer, adrenal cancer, soft tissue sarcoma, urethral cancer, penile cancer, chronic or acute leukemia (including acute myeloid leukemia, chronic myeloid leukemia, acute lymphocytic leukemia, and chronic lymphocytic leukemia), childhood solid tumors, lymphocytic lymphoma, bladder cancer, kidney or ureteral cancer, renal pelvis cancer, central nervous system (CNS) tumor, primary CNS lymphoma, tumor angiogenesis, spinal tumor, brainstem glioma, pituitary adenoma, Kaposi's sarcoma, epidermal carcinoma, squamous cell carcinoma, T cell lymphoma, and environmentally induced cancers, including asbestos-induced cancers, and combinations of the cancers. Preferably, the cancer is a solid tumor cancer. In some embodiments, the cancer is lung cancer such as lung squamous cell carcinoma. In some specific embodiments, the cancer is ovarian cancer. In some specific embodiments, the cancer is colon cancer.

In another aspect, the present invention provides a kit for use in the method of the invention for preparing a modified T cell.

DESCRIPTION OF THE INVENTION

I. Definition

Figure 1:
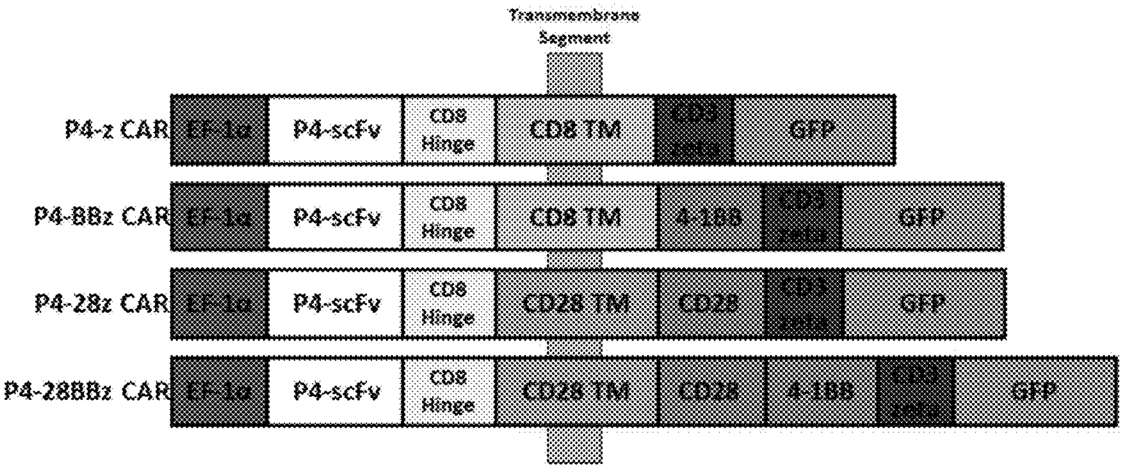
FIG. 1 shows different CAR structures.

In the present invention, the scientific and technical terms used herein have the meaning as commonly understood by a person skilled in the art unless otherwise specified. Also, the protein and nucleic acid chemistry, molecular biology, cell and tissue culture, microbiology, immunology related terms, and laboratory procedures used herein are terms and routine steps that are widely usedin the corresponding field. For example, standard recombinant DNA and molecular cloning techniques used in the present invention are well known to those skilled in the art and are more fully described in the following document: Sambrook, J., Fritsch, E. F. and Maniatis, T., Molecular Cloning: A Laboratory Manual; Cold Spring Harbor Laboratory Press: Cold Spring Harbor, 1989 (hereinafter referred to as "Sambrook"). In the meantime, in order to better understand the present invention, definitions and explanations of related terms are provided below.

"Genome" as used herein encompasses not only chromosomal DNA present in the nucleus, but also organellar DNA present in the subcellular components (eg, mitochondria, plastids) of the cell.

"Exogenous" in reference to a sequence means a sequence from a foreign species, or refers to a sequence in which significant changes in composition and/or locus occur from its native form through deliberate human intervention if from the same species.

"Polynucleotide", "nucleic acid sequence", "nucleotide sequence" or "nucleic acid fragment" are used interchangeably and are single-stranded or double-stranded RNA or DNA polymers, optionally containing synthetic, non-natural or altered nucleotide bases. Nucleotides are referred to by their single letter names as follows: "A" is adenosine or deoxyadenosine (corresponding to RNA or DNA, respectively), "C" means cytidine or deoxycytidine, "G" means guanosine or deoxyguanosine, "U" represents uridine, "T" means deoxythymidine, "R" means purine (A or G), "Y" means pyrimidine (C or T), "K" means G or T, "H" means A or C or T, "I" means inosine, and "N" means any nucleotide.

"Polypeptide," "peptide," and "protein" are used interchangeably in the present invention to refer to a polymer of amino acid residues. The terms apply to an amino acid polymer in which one or more amino acid residues is artificial chemical analogue of corresponding naturally occurring amino acid(s), as well as to a naturally occurring amino acid polymer. The terms "polypeptide," "peptide," "amino acid sequence," and "protein" may also include modified forms including, but not limited to, glycosylation, lipid ligation, sulfation, Y carboxylation of glutamic acid residues, and ADP-ribosylation.

As used in the present invention, "expression construct" refers to a vector such as a recombinant vector that is suitable for expression of a nucleotide sequence of interest in an organism. "Expression" refers to the production of a functional product. For example, expression of a nucleotide sequence may refer to the transcription of a nucleotide sequence (eg, transcription to produce a mRNA or a functional RNA) and/or the translation of an RNA into a precursor or mature protein.

The "expression construct" of the present invention may be a linear nucleic acid fragment, a circular plasmid, a viral vector or, in some embodiments, an RNA that is capable of translation (such as a mRNA).

The "expression construct" of the present invention may comprise regulatory sequences and nucleotide sequences of interes't from different origins, or regulatory sequences and nucleotide sequences of interest from the same source but arranged in a manner different from that normally occurring in nature.

"Regulatory sequence" and "regulatory element" are used interchangeably to refer to a nucleotide sequence that is located upstream (5 'non-coding sequence), middle or downstream (3' non-coding sequence) of a coding sequence and affects the transcription, RNA processing or stability or translation of the relevant coding sequence.

Regulatory sequences may include, but are not limited to, promoters, translation leaders, introns and polyadenylation recognition sequences.

"Promoter" refers to a nucleic acid fragment capable of controlling the transcription of another nucleic acid fragment. In some embodiments of the present invention, the promoter is a promoter capable of controlling the transcription of a gene in a cell, whether or not it is derived from the cell.

As used herein, the term "operably linked" refers to the linkage of a regulatory element (eg, but not limited to, a promoter sequence, a transcription termination sequence, etc.) to a nucleic acid sequence (eg, a coding sequence or an open reading frame) such that transcription of the nucleotide sequence is controlled and regulated by the transcriptional regulatory element. Techniques for operably linking regulatory element regions to nucleic acid molecules are known in the art.

"Gene editing" which is also known as genome editing uses engineered nuclease or "molecular scissors" to insert, delete or replace DNA in an organism's genome. Gene editing results in site-specific double-strand breaks (DSBs) at desired positions in genome, and then introduces desired DNA insertions, deletions or substitutions in the process of repairing DSBs. Meganucleases, zinc finger nucleases (ZFNs), transcription activator-like effector nucleases (TALENs), and CRISPR systems are typically used for gene editing.

"Meganucleases" are a class of deoxyribonuclease enzymes that have a large recognition site (12-40 bp double-stranded DNA sequences), which usually occurs only once in any given genome. For example, the 18 bp sequence identified by meganuclease I-SceI occurs occasionally once on average in a genome 20 times larger than the human genome.

"Zinc finger nucleases" are artificial restriction enzymes prepared by fusing a zinc finger DNA binding domain to a DNA cleavage domain. The zinc finger DNA binding domain of a single ZFN typically contains 3-6 individual zinc finger repeats, each of which can identify a sequence of, for example, 3 bp.

"Transcription activator-like effector nucleases" are restriction enzymes that can be engineered to cleave specific DNA sequences, and that are typically prepared by fusing the DNA-binding domain of a transcription activator-like effector (TALE) to a DNA cleavage domain. TALE can be engineered to bind almost any desired DNA sequence.

"Clustered regularly interspaced short palindromic repeats (CRISPR)" are prokaryotic DNA segments containing short repeats. The CRISPR system is a prokaryotic immune system that confers resistance to foreign genetic elements such as those present in plasmids and phages, and the resistance provides acquired immunity. In this system, Cas proteins or similar proteins cleave foreign nucleic acids under the guidance of RNA.

As used herein, the term "CRISPR nucleases" generally refer to nucleases present in naturally occurring CRISPR systems, as well as their modified forms, variants (including nickase mutants), or catalytically active fragments. CRISPR nucleases can identify and/or cleave target nucleic acids by interacting with a guide RNA such as a crRNA and optionally a tracrRNA or an artificial gRNA such as a sgRNA. The term encompasses any nuclease based on the CRISPR system that enables gene editing in cells.

"Cas9 Nuclease" and "Cas9" are used interchangeably herein and refer to an RNA-directed nuclease comprising a Cas9 protein or a fragment thereof (e.g., a protein comprising an active DNA cleavage domain of Cas9 and/or a gRNA binding domain of Cas9). Cas9 is a component of the CRISPR/Cas (clustered regularly interspaced short palindromic repeats and their associated systems) genome editing system that targets and cleaves DNA target sequences under the guidance of a guide RNA to form DNA double-strand breaks (DSBs).

"Guide RNA" and "gRNA" are used interchangeably herein and generally consist of a crRNA and tracrRNA molecule that partially complements to form a complex, wherein the crRNA comprises a sequence that is sufficiently complementary to a target sequence to hybridize to the target sequence and directs the CRISPR complex (Cas9+crRNA+tracrRNA) to specifically bind to the target sequence. However, it is known in the art to design a single-guide RNA (sgRNA) that simultaneously contains features of crRNA and tracrRNA.

"T cell receptors (TCRs)", which are also known as T cell antigen receptors, refer to molecular structures used by T cells to specifically identify and bind to antigen peptide-MHC molecules, and are usually present on the surface of T cells in a complex form with CD3 molecules. The TCRs of most T cells consist of an alpha chain and a beta peptide chain, and the TCRs of a minority of T cells consist of a gamma chain and a delta peptide chain.

"Chimeric antigen receptors (CARs)", which are also known as artificial T cell receptors, chimeric T cell receptors, or chimeric immune receptors, are artificially designed receptors that can confer immune effector cells a certain specificity. In general, this technique is used to confer T cells the ability to specifically recognize tumor surface antigens. In this way, a large number of cells targeting tumors can be produced.

As used herein, "subject" refers to an organism having or susceptible to a disease (e.g., cancer) that can be treated by the methods, or pharmaceutical compositions of the invention. Non-limiting examples include humans, cows, rats, mice, dogs, monkeys, goats, sheep, cows, deer, and other non-mammals. In a preferred embodiment, the subject is human.

II. Method of Preparing Modified T Cells

In a first aspect, the invention provides a method for preparing a modified T cell, comprising a step of reducing (knock down) or eliminating (knock out) the expression of at least one inhibitory protein in the T cell.

As used herein, an "inhibitory protein" of a T cell refers to a protein related to inhibition of T cell activity. In some embodiments, the inhibitory protein is selected from a T cell surface inhibitory receptor or a T cell exhaustion-related protein.

In some embodiments, the T cell surface inhibitory receptor may be a T cell surface receptor that recognizes a ligand expressed on the surface of tumor cells or surrounding stromal cells. Examples of such receptors include, but are not limited to, TIGIT, BTLA, 2B4, CD160, CD200R, RARA, or combinations thereof.

In some other embodiments, the T cell surface inhibitory receptor may be a receptor that recognizes secretions such as adenosine, epinephrine, etc., or cytokines such as IL-10, TGFβ, etc., present in the tumor microenvironment. Such secretions or cytokines may affect the tumor-killing effects of T cells. Examples of such receptors include, but are not limited to, A2aR, IL10RA, ADRB2, TGFBRII, or combinations thereof.

The inventors surprisingly found that the tumor-killing ability of therapeutic T cells such as CAR-T cells can be enhanced by inhibiting the TGFβ signaling pathway. Therefore, in some preferred embodiments, the T cell surface inhibitory receptor is a TGF β receptor. In some preferred embodiments, the T cell surface inhibitory receptor is a T cell receptor that recognizes the inhibitory cytokine TGFβ1, such as TGFBRII. In addition, the present invention also covers the reduction (knockdown) or elimination (knockout) of the expression of TGFβ signaling pathway related proteins such as FOXP3 in T cells. In some embodiments of the present invention, the expression of TGFβ receptor (such as TGFBRII) and/or FOXP3 in T cells is reduced (knocked down) or eliminated (knocked out).

In some embodiments, the T cell exhaustion-related protein is a T cell exhaustion-related transcription factor, for example, a transcription factor whose expression is significantly up-regulated in exhausted T cells. Examples of such transcription factors include, but are not limited to, BATF, GATA3, IRF4, or combinations thereof.

It was reported that the epigenetics of exhausted T cells are significantly different from those of non-exhausted T cells. Therefore, in some embodiments, the T cell exhaustion-associated protein is an epigenetic-associated protein, such as a methyltransferase. In some embodiments, the methyltransferase is DNMT3A.

The single-cell sequencing technology emerged in recent years has obtained a new class of proteins that are highly expressed in exhausted T cells, but how they affect T cell function is still unclear. Such proteins that are highly expressed in exhausted T cells are also included in the scope of the present invention. For example, in some embodiments, the T cell exhaustion-related protein is selected from LAYN, MYO7A, PHLDA1, RGS1, RGS2, or combinations thereof.

In some embodiments, the T cell exhaustion-related protein is a protein related to the endogenous mechanism of T cell exhaustion, such as a T cell apoptosis-related protein. Examples of such proteins related to the endogenous mechanism of T cell exhaustion include, but are not limited to, SHP1, DGKa, Fas, FasL, or combinations thereof.

In some embodiments, the method of the present invention includes reducing or eliminating the expression of at least 1, at least 2, at least 3, at least 4, or more of the above-mentioned inhibitory proteins in T cells, the inhibitory protein is for example selected from a TGFB receptor (such as TGFBRII), TIGIT, BTLA, 2B4, CD160, CD200R, A2aR, IL10RA, ADRB2, BATF, GATA3, IRF4, RARA, LAYN, MYO7A, PHLDA1, RGS1, RGS2, SHP1, DGKa, Fas, and FasL.

In some embodiments, the methods of the present invention further include reducing or eliminating PD1 expression in the T cells. In some embodiments, the methods of the invention include reducing or eliminating the expression of TGFβ receptors (such as TGFBRII) and PD1 in the T cells.

The T cells of the present invention may be T cells for adoptive immunotherapy produced by expanding antigen-specific T cells or by redirection of T cells through genetic engineering. The T cells can also be primary T cells isolated from a subject. In some embodiments, the T cells are T cells comprising exogenous T cell receptors (TCRs). In some other embodiments, the T cells are T cells comprising chimeric antigen receptors (CARs). In some embodiments, the T cells are CD4+ T cells. In some embodiments, the T cells are CD8+T cells.

In some embodiments, the method further comprises a step of providing unmodified T cells isolated from the subject, and a step of introducing a TCR or CAR into the unmodified T cells. In some embodiments, the step of introducing a TCR or CAR into the unmodified T cells is performed before or after or simultaneously with the step of reducing or eliminating expression of the inhibitory protein in the T cells.

In some embodiments, the TCR or CAR comprises an antigen binding domain against a tumor associated antigen, such as an extracellular antigen binding domain.

The tumor associated antigens include but are not limited to CD16, CD64, CD78, CD96, CLL1, CD116, CD117, CD71, CD45, CD71, CD123, CD138, ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD30, CD40, disialylganglioside GD2, ductal epithelial mucin, gp36, TAG-72, glycosphingolipid, glioma-related antigens, β-human chorionic gonadotropin, a-fetoglobulin (AFP), lectin-responsive AFP, thyroglobulin, RAGE-1, MN-CA IX, human telomerase reverse transcriptase, RUI, RU2

(AS), intestinal carboxyl esterase, mut hsp70-2, M-CSF, prostase, prostatase specific antigen (PSA), PAP, NY-ESO-1, LAGA-1a, p53, Prostein, PSMA, survival and telomerase, prostate cancer tumor antigen-1 (PCTA-1), MAGE, ELF2M, neutrophil elastase, ephrin B2, CD22, insulin growth factor (IGF1)-I, IGF-II, IGFI receptor, mesothelin, major histocompatibility complex (MHC) molecules that present tumor-specific peptide epitopes, 5T4, ROR1, Nkp30, NKG2D, tumor stromal antigen, fibronectin extra domain A (EDA) and extra domain B (EDB), tenascin-C Al domain (TnC A1), fibroblast-associated protein (fap), CD3, CD4, CD8, CD24, CD25, CD33, CD34, CD133, CD138, Foxp3, B7-1 (CD80), B7-2 (CD86), GM-CSF, cytokine receptor, endothelial factor, BCMA (CD269, TNFRSF17), TNFRSF17 (UNIPROT Q02223), SLAMF7 (UNIPROT Q9NQ25), GPRC5D (UNIPROT Q9NZD1), FKBP11 (UNIPROT Q9NYL4), KAMP3, ITGA8 (UNIPROT P53708) and FCRL5 (UNIPROT Q68SN8). In a preferred embodiment, the antigen is mesothelin.

According to the present invention, the antigen-binding domain may be, for example, a monoclonal antibody, a synthetic antibody, a human antibody, a humanized antibody, a single domain antibody, an antibody single-chain variable region, and an antigen-binding fragment thereof.

In a preferred embodiment, the antigen binding domain is a monoclonal antibody against mesothelin. In a preferred embodiment, the antigen binding domain is a scFv against mesothelin. In a preferred embodiment, the antigen binding domain is the scFv P4 against mesothelin, for example, a scFv having an amino acid sequence set forth in SEQ ID NO:22.

In some embodiments, the CAR comprises a transmembrane domain, such as a CD8 transmembrane domain or a CD28 transmembrane domain, preferably a CD28 transmembrane domain, e.g., a CD28 transmembrane structure having an amino acid sequence set forth in SEQ ID NO:23.

In some embodiments, the CAR further comprises a hinge region between the extracellular antigen binding domain and the transmembrane domain, e.g., the hinge region is a CD8 hinge region, such as a CD8 hinge region having amino acid sequence set forth in SEQ ID NO: 24.

In some embodiments, the CAR comprises a signal transduction domain that can be used for T cell activation, e.g., a signal transduction domain selected from the group consisting of TCRζ, FRγ, FcRβ, FcRε, CD3γ, CD3δ, CD3ε, CD3ζ, CD5, CD22, CD79a, CD79b, and CD66d. In some preferred embodiments, the CAR comprises a CD3} signal transduction domain, such as a CD3ζ signal transduction domain having an amino acid sequence set forth in SEQ ID NO:25.

In some embodiments, the CAR further comprises one or more costimulatory domains selected from the group consisting of CD3, CD27, CD28, CD83, CD86, CD127, 4-1BB, and 4-1BBL. In some embodiments, the CAR comprises a CD28 costimulatory domain, e.g., a CD28 costimulatory domain having an amino acid sequence set forth in SEQ ID NO:26.

In some embodiments, the CAR may further comprise a reporter molecule, such as a GFP protein, for displaying or tracking CAR expression.

In some preferred embodiments of the invention, the CAR comprises a scFv P4 against mesothelin, a CD8 hinge region, a CD28 transmembrane domain, a CD28 costimulatory domain, a CD3ζ signal transduction domain, and optionally a GFP protein. In some preferred embodiments of the invention, the CAR comprises an amino acid sequence set forth in SEQ ID NO: 27.

Several methods are known in the art to reduce or eliminate protein expression in cells. In some embodiments, the expression of an inhibitory protein in T cells is reduced or eliminated by antisense RNA, antagomir, siRNA, shRNA. In other embodiments, the expression of inhibitory proteins in T cells is reduced or eliminated by methods of gene editing, such as by meganucleases, zinc finger nucleases, transcription activator-like effector nucleases, or CRISPR systems. In a preferred embodiment of the method of the invention, the CRISPR system is used to reduce or eliminate the expression of inhibitory proteins in T cells.

In some embodiments, the nuclease used in the CRISPR system (CRISPR nuclease) can be selected, for example, from a group consisting of Cas3, Cas8a, Cas5, Cas8b, Cas8c, Cas10d, Cse1, Cse2, Csy1, Csy2, Csy3, GSU0054, Cas10, Csm2, Cmr5, Cas10, Csx11, Csx10, Csf1, Cas9, Csn2, Cas4, Cpf1, C2c1, C2c3 or C2c2 proteins, or functional variants of these nucleases.

In some embodiments, the CRISPR system is a CRISPR/Cas9 system. In some embodiments, the CRISPR system, e.g., a CRISPR/Cas9 system, targets one or more of the nucleotide sequences in the cells selected from the group consisting of SEQ ID NOs: 1-21 and 28-31.

In some embodiments, the CRISPR system is assembled in vitro and transferred to T cells. In some embodiments, an expression construct encoding all of the elements of the CRIPSR system is transformed into T cells. In some embodiments, an expression construct encoding part of the elements of the CRIPSR system, as well as other transcribed or translated elements are transferred into T cells.

The present invention also provides a CRISPR gene editing system for preparing a modified T cell, comprising at least one of the following i) to v):

i) a CRISPR nuclease, and at least one guide RNA;
ii) an expression construct comprising a nucleotide sequence encoding a CRISPR nuclease, and at least one guide RNA;
iii) a CRISPR nuclease, and an expression construct comprising a nucleotide sequence encoding at least one guide RNA;
iv) an expression construct comprising a nucleotide sequence encoding a CRISPR nuclease, and an expression construct comprising a nucleotide sequence encoding at least one guide RNA;
v) an expression construct comprising a nucleotide sequence encoding a CRISPR nuclease and a nucleotide sequence encoding at least one guide RNA;

wherein the at least one guide RNA targets an inhibitory protein encoding gene in the T cell, said inhibitory protein is selected from a T cell surface inhibitory receptor or a T cell exhaustion-related protein, such as a TGFβ receptor (such as TGFBRII), TIGIT, BTLA, 2B4, CD160, CD200R, A2aR, IL10RA, ADRB2, BATF, GATA3, IRF4, RARA, LAYN, MYO7A, PHLDA1, RGS1, RGS2, SHP1, DGKa, Fas, FasL, or combinations thereof. In some embodiments, the at least one guide RNA further includes a guide RNA that targets a gene encoding PD1 in the T cell. In some embodiments, the at least one guide RNA includes a guide RNA that targets the gene encoding a TGFβ receptor (such as TGFBRII) and the gene encoding PD1 in the T cell.

In some specific embodiments, the at least one guide RNA targets one or more nucleotide sequences selected from SEQ ID NOs: 1-21 and 28-31 in the T cell.

In some embodiments, the CRISPR nuclease can be, for example, selected from the group consisting of Cas3, Cas8a, Cas5, Cas8b, Cas8c, Cas10d, Cse1, Cse2, Csy1, Csy2, Csy3, GSU0054, Cas10, Csm2, Cmr5, Cas10, Csx11, Csx10, Csf1, Cas9, Csn2, Cas4, Cpf1, C2cl, C2c3 or C2c2 proteins, or functional variants of these nucleases. In some embodiments, the CRISPR nuclease is a Cas9 nuclease or a functional variant thereof.

In some embodiments of the methods of the invention, the introduction of the CRISPR gene editing system of the invention into T cells is included. In some embodiments, the CRISPR gene editing system of the invention results in a reduction or elimination of expression (knockdown or knockout) of the targeted protein after introduction into T cells.

The CRISPR system of the invention can be transformed into T cells by methods known in the art, such as: calcium phosphate transfection, protoplast fusion, electroporation, lipofection, microinjection, viral infection (e.g. baculovirus, vaccinia virus, adenoviruses and other viruses).

The modified T cells of the invention may be activated and proliferated before or after genetic modification. T cells may be proliferated in vitro or in vivo. Generally, the T cells of the present invention may be proliferated, for example, by contacting an agent that stimulates the CD3 TCR complex and costimulatory molecules on the surface of the T cell to generate a T cell activation signal. For example, chemicals such as a calcium ionophore A23187, phorbol 12-myristate 13-acetate (PMA), or mitotic lectins such as phytohemagglutinin (PHA) can be used to generate T cell activation signals. In some embodiments, the T cell population may be activated by contacting in vitro, for example, an anti-CD3 antibody or a antigen-binding fragment thereof, or an anti-CD2 antibody immobilized on a surface, or by contacting a protein kinase C activator (for example, a moss inhibitor) together with the calcium ionophore carrier. For example, under conditions suitable for stimulating T cell proliferation, the T cell population may be in contact with anti-CD3 antibodies and anti-CD28 antibodies. Conditions suitable for T cell culture include suitable culture media that may contain factors necessary for proliferation and viability (such as Minimal Essential Media or RPMI Media 1640, or X-vivo 5, (Lonza)), where the necessary factors include serum (such as fetal bovine or human serum), interleukin-2 (IL-2), insulin, IFN-γ, IL-4, IL-7, GM-CSF, IL-10, IL-2, IL-15, TGFβ and TNF, or additives for cell growth known to those skilled in the art. Other additives for cell growth include but are not limited to surfactants, human plasma protein powder, and reducing agents such as N-acetyl-cysteine and 2-mercaptoacetic acid. The culture media may include RPMI 1640, AIM-V, DMEM, MEM, a-MEM, F-12, X-Vivo 1 and X-Vivo 20, Optimizer, amino acids, sodium pyruvate and vitamins, serum-free or supplemented with appropriate amount of serum (or plasma) or a specific set of hormones, and/or a certain quantity of cytokines sufficient for the growth and proliferation of T cells. The target cells can be maintained under conditions necessary to support growth, such as an appropriate temperature (e.g., 37° C.) and environment (e.g., air plus 5% $CO_2$).

III. Modified T cells

In another aspect, the invention provides a modified T cell, wherein the expression of an inhibitory protein in the modified T cell is reduced or eliminated as compared with an unmodified T cell. In some embodiments, the modified T cell is prepared by the methods of the invention.

In some embodiments, the inhibitory protein is selected from a T cell surface inhibitory receptor or a T cell exhaustion-related protein.

In some embodiments, the T cell surface inhibitory receptor may be a T cell surface receptor that recognizes a ligand expressed on the surface of tumor cells or surrounding stromal cells. Examples of such receptors include, but are not limited to, TIGIT, BTLA, 2B4, CD160, CD200R, RARA, or combinations thereof.

In some other embodiments, the T cell surface inhibitory receptor may be a receptor that recognizes secretions such as adenosine, epinephrine, etc., or cytokines such as IL-10, TGFβ, etc., present in the tumor microenvironment. Such secretions or cytokines may affect the tumor-killing effects of T cells. Examples of such receptors include, but are not limited to, A2aR, IL10RA, ADRB2, TGFBRII, or combinations thereof.

The inventors surprisingly found that the tumor-killing ability of therapeutic T cells such as CAR-T cells can be enhanced by inhibiting the TGFβ signaling pathway. Therefore, in some preferred embodiments, the T cell surface inhibitory receptor is a TGF β receptor. In some preferred embodiments, the T cell surface inhibitory receptor is a T cell receptor that recognizes the inhibitory cytokine TGFβ1, such as TGFBRII. In addition, the present invention also covers the reduction (knockdown) or elimination (knockout) of the expression of TGFβ signaling pathway related proteins such as FOXP3 in T cells. In some embodiments of the present invention, the expression of TGFB receptor (such as TGFBRII) and/or FOXP3 in T cells is reduced (knocked down) or eliminated (knocked out).

In some embodiments, the T cell exhaustion-related protein is a T cell exhaustion-related transcription factor, for example, a transcription factor whose expression is significantly up-regulated in exhausted T cells. Examples of such transcription factors include, but are not limited to, BATF, GATA3, IRF4, or combinations thereof.

It was reported that the epigenetics of exhausted T cells are significantly different from those of non-exhausted T cells. Therefore, in some embodiments, the T cell exhaustion-associated protein is an epigenetic-associated protein, such as a methyltransferase. In some embodiments, the methyltransferase is DNMT3A.

The single-cell sequencing technology emerged in recent years has obtained a new class of proteins that are highly expressed in exhausted T cells, but how they affect T cell function is still unclear. Such proteins that are highly expressed in exhausted T cells are also included in the scope of the present invention. For example, in some embodiments, the T cell exhaustion-related protein is selected from LAYN, MYO7A, PHLDA1, RGS1, RGS2, or combinations thereof.

In some embodiments, the T cell exhaustion-related protein is a protein related to the endogenous mechanism of T cell exhaustion, such as a T cell apoptosis-related protein. Examples of such proteins related to the endogenous mechanism of T cell exhaustion include, but are not limited to, SHP1, DGKa, Fas, FasL, or combinations thereof.

In some embodiments, as compared with an unmodified T cell, the expression of at least 1, at least 2, at least 3, at least 4, or more of the above-mentioned inhibitory proteins in the modified T cell of the invention is reduced or eliminated, the inhibitory protein is for example selected from a TGFβ receptor (such as TGFBRII), TIGIT, BTLA, 2B4, CD160, CD200R, A2aR, IL10RA, ADRB2, BATF, GATA3, IRF4, RARA, LAYN, MYO7A, PHLDA1, RGS1, RGS2, SHP1, DGKa, Fas, and FasL. In some further embodiments, as compared with an unmodified T cell, the expression of PD1 in the modified T cell of the invention is reduced or eliminated. In some further embodiments, as compared with an unmodified T cell, the expression of the TGFB receptor (such as TGFBRII) in the modified T cell of the invention is reduced or eliminated.

In some embodiments, the gene encoding the inhibitory protein in the T cell is knocked out, for example, by introducing the gene editing system of the invention.

According to the present invention, the modified T cells have comparable expansion ability and similar immunological properties to the unmodified T cells, and have enhanced biological activity since immunosuppression is relieved, such as antitumor activity, especially activity of inhibiting or killing solid tumor cells.

In some embodiments, the T cells are T cells comprising exogenous T cell receptors (TCRs). In some other embodiments, the T cells are T cells comprising chimeric antigen receptors (CARs). In some preferred embodiments, the T cells are CAR-T cells.

In some embodiments, the TCR or CAR comprises an antigen binding domain against a tumor associated antigen, such as an extracellular antigen binding domain.

The tumor associated antigens include but are not limited to CD16, CD64, CD78, CD96, CLL1, CD116, CD117, CD71, CD45, CD71, CD123, CD138, ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD30, CD40, disialylganglioside GD2, ductal epithelial mucin, gp36, TAG-72, glycosphingolipid, glioma-related antigens, β-human chorionic gonadotropin, a-fetoglobulin (AFP), lectin-responsive AFP, thyroglobulin, RAGE-1, MN-CA IX, human telomerase reverse transcriptase, RU1, RU2 (AS), intestinal carboxyl esterase, mut hsp70-2, M-CSF, prostase, prostatase specific antigen (PSA), PAP, NY-ESO-1, LAGA-1a, p53, Prostein, PSMA, survival and telomerase, prostate cancer tumor antigen-1 (PCTA-1), MAGE, ELF2M, neutrophil elastase, ephrin B2, CD22, insulin growth factor (IGF1)-I, IGF-II, IGFI receptor, mesothelin, major histocompatibility complex (MHC) molecules that present tumor-specific peptide epitopes, 5T4, ROR1, Nkp30, NKG2D, tumor stromal antigen, fibronectin extra domain A (EDA) and extra domain B (EDB), tenascin-C Al domain (TnC A1), fibroblast-associated protein (fap), CD3, CD4, CD8, CD24, CD25, CD33, CD34, CD133, CD138, Foxp3, B7-1 (CD80), B7-2 (CD86), GM-CSF, cytokine receptor, endothelial factor, BCMA (CD269, TNFRSF17), TNFRSF17 (UNIPROT Q02223), SLAMF7 (UNIPROT Q9NQ25), GPRC5D (UNIPROT Q9NZD1), FKBP11 (UNIPROT Q9NYL4), KAMP3, ITGA8 (UNIPROT P53708) and FCRL5 (UNIPROT Q68SN8). In a preferred embodiment, the antigen is mesothelin.

According to the present invention, the antigen-binding domain may be, for example, a monoclonal antibody, a synthetic antibody, a human antibody, a humanized antibody, a single domain antibody, an antibody single-chain variable region, and an antigen-binding fragment thereof.

In a preferred embodiment, the antigen binding domain is a monoclonal antibody against mesothelin. In a preferred embodiment, the antigen binding domain is a scFv against mesothelin. In a preferred embodiment, the antigen binding domain is the scFv P4 against mesothelin, for example, a scFv having an amino acid sequence set forth in SEQ ID NO:22.

In some embodiments, the CAR comprises a transmembrane domain, such as a CD8 transmembrane domain or a CD28 transmembrane domain, preferably a CD28 transmembrane domain, e.g., a CD28 transmembrane structure having an amino acid sequence set forth in SEQ ID NO:23.

In some embodiments, the CAR further comprises a hinge region between the extracellular antigen binding domain and the transmembrane domain, e.g., the hinge region is a CD8 hinge region, such as a CD8 hinge region having amino acid sequence set forth in SEQ ID NO: 24.

In some embodiments, the CAR comprises a signal transduction domain that can be used for T cell activation, e.g., a signal transduction domain selected from the group consisting of TCRζ, FcRγ, FcRβ, FcRε, CD3γ, CD3δ, CD3ε, CD3ζ, CD5, CD22, CD79a, CD79b, and CD66d. In some preferred embodiments, the CAR comprises a CD3ζ signal transduction domain, such as a CD32 signal transduction domain having an amino acid sequence set forth in SEQ ID NO:25.

In some embodiments, the CAR further comprises one or more costimulatory domains selected from the group consisting of CD3, CD27, CD28, CD83, CD86, CD127, 4-1BB, and 4-1BBL. In some embodiments, the CAR comprises a CD28 costimulatory domain, e.g., a CD28 costimulatory domain having an amino acid sequence set forth in SEQ ID NO:26.

In some embodiments, the CAR may further comprise a reporter molecule, such as a GFP protein, for displaying or tracking CAR expression.

In some preferred embodiments of the invention, the CAR comprises a scFv P4 against mesothelin, a CD8 hinge region, a CD28 transmembrane domain, a CD28 costimulatory domain, a CD3ζ signal transduction domain, and optionally a GFP protein. In some preferred embodiments of the invention, the CAR comprises an amino acid sequence set forth in SEQ ID NO: 27.

In a specific embodiment of the present invention, the modified T cell is a CAR-T cell comprising the CAR of the amino acid sequence shown in SEQ ID NO: 27, wherein the expression of at least one inhibitory protein or a combination of inhibitory proteins selected from TGFB receptor (such as TGFBRII), TIGIT, BTLA, 2B4, CD160, CD200R, A2aR, IL10RA, ADRB2, BATF, GATA3, IRF4, RARA, LAYN, MYO7A, PHLDA1, RGS1, RGS2, SHP1, is reduced or eliminated. DGKa, Fas, FasL or any combination thereof is reduced or eliminated.

The cells of the present invention can be obtained from many non-limiting sources by various non-limiting methods, including peripheral blood mononuclear cells, bone marrow, lymph node tissues, umbilical cord blood, thymus tissues, ascites, pleural effusions, spleen tissues and tumors. In some embodiments, the cells may be derived from a healthy donor or from a patient diagnosed with cancer. In some embodiments, the cells may be part of a mixed population of cells exhibiting different phenotypic characteristics. In some embodiments, the T cell is a CD4+ T cell. In some embodiments, the T cell is a CD8+ T cell.

In some embodiments of various aspects of the present invention, the T cells are derived from autologous cells of the subject. As used herein, “autologous” refers to that cells, cell lines, or cell populations used to treat the subject are derived from the subject per se. In some embodiments, the T cells are derived from allogeneic cells, such as from a donor compatible with the subject’s human leukocyte antigen (HLA). Standard schemes can be used to convert cells from a donor into non-alloreactive cells and to replicate the cells as required, generating cells that can be administered to one or more patients.

The CAR T cells or TCR T cells of the invention can be prepared by a variety of means known in the art. For example, the CAR-T cells or TCR-T cells can be obtained by transducing T cells with an expression construct comprising a CAR or TCR coding sequence.

Those skilled in the art will be able to readily construct expression constructs suitable for protein expression, such as viral vectors.

IV. Pharmaceutical Compositions and Applications

In another aspect, the invention also provides a pharmaceutical composition for treating cancer comprising the modified T cell of the invention and a pharmaceutically acceptable carrier. Furthermore, the invention also provides the use of the modified T cell of the invention in the manufacture of a medicament for treatment of cancer.

As used herein, “pharmaceutically acceptable carrier” include any and all solvents, dispersion media, coatings, antibacterial and antifungal agents, isotonic and absorption delaying agents, and the like that are physiologically compatible. Preferably, the carriers are suitable for intravenous, intramuscular, subcutaneous, parenteral, spinal or epidermal administration (e.g., by injection or infusion).

In another aspect, the invention also provides a method for treating cancer, comprising administering to a subject in need a therapeutically effective amount of the modified T cell of the invention or a pharmaceutical composition of the invention.

In some embodiments, the method further comprises administering to the subject a radiation therapy and/or a chemotherapy and/or additional tumor targeting drugs (e.g., monoclonal antibodies or small molecule compounds that target other antigens).

As used herein, “therapeutically effective amount” or “therapeutically effective dose” or “effective amount” refers to an amount of a substance, compound, material or cell that is at least sufficient to produce a therapeutic effect after administration to a subject. Thus, it is an amount necessary to prevent, cure, ameliorate, arrest or partially arrest the symptoms of a disease or condition.

For example, an “effective amount” of cells or pharmaceutical composition of the invention preferably results in a decrease in the severity of the symptoms of the disease, an increase in the frequency and duration of the asymptomatic phase of the disease, or prevention of damage or disability caused by the disease. For example, for the treatment of a tumor, an “effective amount” of cells or pharmaceutical composition of the invention preferably inhibits tumor cell growth or tumor growth relative to a subject not receiving the treatment by at least about 10%, preferably at least about 20%, preferably at least about 30%, more preferably at least about 40%, more preferably at least about 50%, more preferably at least about 60%, more preferably at least about 70%, more preferably at least about 80%. The ability to inhibit tumor growth can be evaluated in animal model systems which can be used to predict the therapeutic effect on human tumors. Alternatively, it can also be evaluated by examining the ability to inhibit tumor cell growth, which can be determined in vitro by assays well known to those skilled in the art.

Actual dosage levels of the cells in the pharmaceutical compositions of the invention may be varied so as to obtain an amount of the cells which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Surprisingly, the modified T cells of the present invention can achieve superior therapeutic effects at lower doses relative to control T cells (in which the expression of the inhibitory protein is not reduced or eliminated). This is particularly advantageous in reducing the time and cost of preparation while reducing the side effects associated with high dose administration.

For example, the modified T cells of the present invention are administered at a dose that is about 2 times lower, about 3 times lower, about 4 times lower, about 5 times lower, about 6 times lower, about 7 times lower, about 8 times lower, about 9 times lower, about 10 times lower, about 15 times lower, about 20 times lower, about 30 times lower, about 40 times lower, about 50 lower, about 100 times lower, about 150 times lower, and about 200 or more times lower than control T cells in which expression of the inhibitory protein is not reduced or eliminated.

Non-limiting examples of cancers that can be treated by the cell or pharmaceutical composition of the invention include lung cancer, ovarian cancer, colon cancer, rectal cancer, melanoma, kidney cancer, bladder cancer, breast cancer, liver cancer, lymphoma, hematological malignancies, head and neck cancers, glial tumor, stomach cancer, nasopharyngeal cancer, throat cancer, cervical cancer, uterine body tumor and osteosarcoma. Examples of other cancers that can be treated with the method or pharmaceutical composition of the present invention include: bone cancer, pancreatic cancer, skin cancer, prostate cancer, skin or intraocular malignant melanoma, uterine cancer, anal cancer, testicular cancer, fallopian tube cancer, endometrial cancer, vaginal cancer, vaginal cancer, Hodgkin’s disease, non-Hodgkin’s lymphoma, esophageal cancer, small intestine cancer, endocrine system cancer, thyroid cancer, parathyroid cancer, adrenal cancer, soft tissue sarcoma, urethral cancer, penile cancer, chronic or acute leukemia (including acute myeloid leukemia, chronic myeloid leukemia, acute lymphocytic leukemia, and chronic lymphocytic leukemia), childhood solid tumors, lymphocytic lymphoma, bladder cancer, kidney or ureteral cancer, renal pelvis cancer, central nervous system (CNS) tumor, primary CNS lymphoma, tumor angiogenesis, spinal tumor, brainstem glioma, pituitary adenoma, Kaposi’s sarcoma, epidermal carcinoma, squamous cell carcinoma, T cell lymphoma, and environmentally induced cancers, including asbestos-induced cancers, and combinations of the cancers. Preferably, the cancer is a solid tumor cancer. In some embodiments, the cancer is lung cancer such as lung squamous cell carcinoma. In some specific embodiments, the cancer is ovarian cancer. In some specific embodiments, the cancer is colon cancer.

V. Kit

The invention also provides a kit for use in the method of preparing the modified T cell of the invention, which comprises a CRISPR gene editing system for preparing the modified T cell as described herein, and suitable reagents for introducing the gene editing system into cells.

In some embodiments, the kit includes a CRISPR nuclease such as Cas9 protein. In some embodiments, the kit includes one or more sgRNAs, for example, the sgRNA targets any one or more target sequences in SEQ ID NOs: 1-21 and 28-31. In some other embodiments, the kit contains reagents for in vitro transcription of sgRNA.

The kit may further comprise reagents for detecting T cells, isolating T cells, activating T cells, and/or expanding T cells. The kit may further comprise reagents for introducing a CAR or TCR into T cells, reagents for detecting and/or isolating cells expressing the CAR or TCR. The kit may also contain instructions for carrying out the methods of the invention.

EXAMPLES

A further understanding of the present invention may be obtained by reference to the examples set forth herein, which are not intended to limit the scope of the invention. It is apparent that various modifications and changes can be made to the present invention without departing from the spirit of the invention, and such modifications and variations are also within the scope of the present invention.

Materials and Methods

1. In Vitro Transcription of sgRNA

First, a forward primer containing a T7 promoter and a 20 bp target sequence (sgRNA) was synthesized by a biotechnology company, and then the T7-sgRNA PCR product was amplified in vitro using the pX330 plasmid (Addgene plasmid #4223) as a PCR template and the PCR product was purified using a PCR purification kit. The purified T7-sgRNA PCR product was then used as a template, the sgRNA was in vitro transcribed using MEGAshortscript T7 kit (Thermo Fisher Scientific), and the sgRNA was recovered by MEGAclear columns (Thermo Fisher Scientific), and the sgRNA was dissolved in RNase-free deionized water, frozen separately or reserved for subsequent use.

| Genes to be knocked out | Genbank Gene ID | sgRNA target sequence | SEQ ID NO: |
|---|---|---|---|
| TIGIT | 201633 | tcctcctgatctgggcccag | 1 |
| BTLA | 151888 | aagacattgcctgccatgct | 2 |
| CD160 | 11126 | tgcaggatgctgttggaacc | 3 |
| 2B4 (CD244) | 51744 | gatacaccttgaggagcagg | 4 |
| CD200R (CD200R1) | 131450 | cctaggttagcagttctcca | 5 |
| BATF | 10538 | gctgtcggagctgtgaggca | 6 |
| GATA3 | 2625 | ttccgtagtagggcgggacg | 7 |
| IRF4 | 3662 | ctgatcgaccagatcgacag | 8 |
| RARA | 5914 | ccattgaggtgcccgccccc | 9 |
| A2aR | 135 | ctcctcggtgtacatcacgg | 10 |
| IL10RA | 3587 | gcgccgccagcagcactacg | 11 |
| ADRB2 | 154 | caagaaggcgctgccgttcc | 12 |
| LAYN | 143903 | tagcgcggttcccggcctca | 13 |
| MYO7A | 4647 | agcttcaccaccgccccgat | 14 |
| PHLDA1 | 22822 | ggcgcacgcctcattaactt | 15 |
| RGS1 | 5996 | gtcgtctagaagtgaatgag | 16 |
| RGS2 | 5997 | agacccatggacaagagcgc | 17 |

-continued

| Genes to be knocked out | Genbank Gene ID | sgRNA target sequence | SEQ ID NO: |
|---|---|---|---|
| SHP1 | 5777 | tcggcccagtcgcaagaacc | 18 |
| DGKA | 1606 | gttgcttggacctcttcaga | 19 |
| Fas | 355 | gagggtccagatgcccagca | 20 |
| FasL | 356 | gtaattgaagggctgctgca | 21 |

2. Complex of Cas9 Protein with sgRNA

First, an appropriate amount of the corresponding sgRNA was added to a RNase-free EP tube, then the Cas9 protein was slowly added, gently mixed, and incubated at room temperature for 15 minutes to form RNP for subsequent use.

3. Electroporation Transformation

1) P3 Primary Cell 4D-Nucleofector X Kit was used;
2) 1.5 ml/well complete medium was added to a 12-well plate and was preheated for more than 30 min at 37° C.; simultaneously, medium in a 15 ml centrifuge tube was preheated; 50 ml PBS was preheated;
3) the corresponding sgRNA was added to a RNase-free EP tube, then a corresponding amount of Cas9 protein was slowly added, gently mixed and incubated for 20 min at room temperature to form RNP complex;
4) preparation of electrorotation buffer: in 100 μl system, 82 μl nuclepfector solution+18 μl supplement;
5) during the incubation of sgRNA and cas9 protein, cells required for electroporation were prepared synchronously;
6) T cells activated for 3 days were collected, counted, and the required amount of cells (3e6 cells/sample) was taken out;
7) the solution was centrifuged at 200g and room temperature for 5 min;
8) the supernatant was removed, the cells were washed once with pre-heated PBS, then centrifuged at 200g and room temperature for 5 min;
9) the supernatant was removed and residual liquid was further removed as much as possible;
10) the cells were resuspended with the previously prepared electroporation buffer and mixed gently;
11) 200 μl/sample (including duplicate wells) were removed from the resuspended cells into the incubated RNP, mixed gently, and then 100 μl/sample of the mixture was added to an electroporation cuvette;
12) the program for electroporation is stimulated T cells (EO-115);
13) 500 μl pre-heated medium was rapidly added to the cuvette after electroporation, mixed gently with a pipette, the cell suspension was pipetted into the preheated 12-well plate and placed back into the incubator, incubated at 5% $CO_2$,37° C.;
14) half medium was refreshed after 6 hours of electroporation, the cells were carefully removed from the incubator without shaking, 1 ml/well of medium was carefully pipetted out along the well wall, and then 1 ml of pre-heated T cell culture medium was added to each well;
15) Thereafter, according to the state of cell growth, passage was carried out on time, and the cell density was maintained at 1e6 cells/ml.

4. Isolation of CD3+ Cells and Preparation of CAR-T Cells

After the peripheral blood or cord blood was sorted into mononuclear cells (PBMC) with the lymphocyte separator (Histopaque-1077), the PBMCs were then separated from the CD3+ cells using the EasySeq human T cell Enrichment kit. After obtaining CD3+ cells, CAR lentivirus infection was carried out to obtain CAR-T cells.

Subsequently, as described above, each RNP was electroporated into CAR-T cells, the target gene was knocked out, and gene-edited CAR-T cells were obtained.

5. Tumor Cell Lines

The tumor cells CRL5826 (NCI-H226 human lung squamous cell line), OVCAR3 (human ovarian cancer cell) and HCT116 (human colon cancer cell) were purchased from ATCC, all expressing the antigen Mesothelin. The cell line was infected with a virus for expressing luciferase to obtain a cell line stably expressing luciferase (CRL5826-luci, OVCAR3-luci, HCT116-luci). On this basis, the virus expressing PDL1 was transfected to obtain a cell line (CRL5826-PDL1-luci) with high expression of PDL1.

6. In Vitro Killing of CAR-T Cells

The tumor cells were placed in a 96-well micro-assay-plate (greiner bio-one) at a density of 104/100 μl. CAR-T cells were accurately counted, diluted according to different ratios of effector cells: target cells, and 100 μl was added to the corresponding wells. For the control group, 100 μl of culture medium was add. At the specified time points, 10 μl Steady-Glo® Luciferase Assay System=was added to all the wells, 5 minutes later, read on the microplate reader. After getting the reading, the percentage of killing wase calculated: killing (%)=100-(reading of the experimental group/reading of the control group)*100.

Example 1. The Effects of CAR-T Cells with Different CAR Structures

Four types of CAR (P4-z, P4-BBz, P4-28z, and P4-28BBz) were designed, the structures of which were shown in FIG. 1, wherein P4 is anti-mesothelin scFv), and CAR-T cells were prepared.

At a ratio of 1:1 effector cells: target cells, the obtained CAR-T cells and H226 cells were co-cultured for 20 hours, and the release of IFN-γ and IL-2 was measured.

At a 2:1 ratio of effector cells to target cells, the obtained CAR-T cells were co-cultured with luciferase-expressing H226 cells (H226-luci) for 3 days, and the target cell lysis percentage was calculated by measuring the luciferase activity of the remaining tumor cells.

Figure 2:
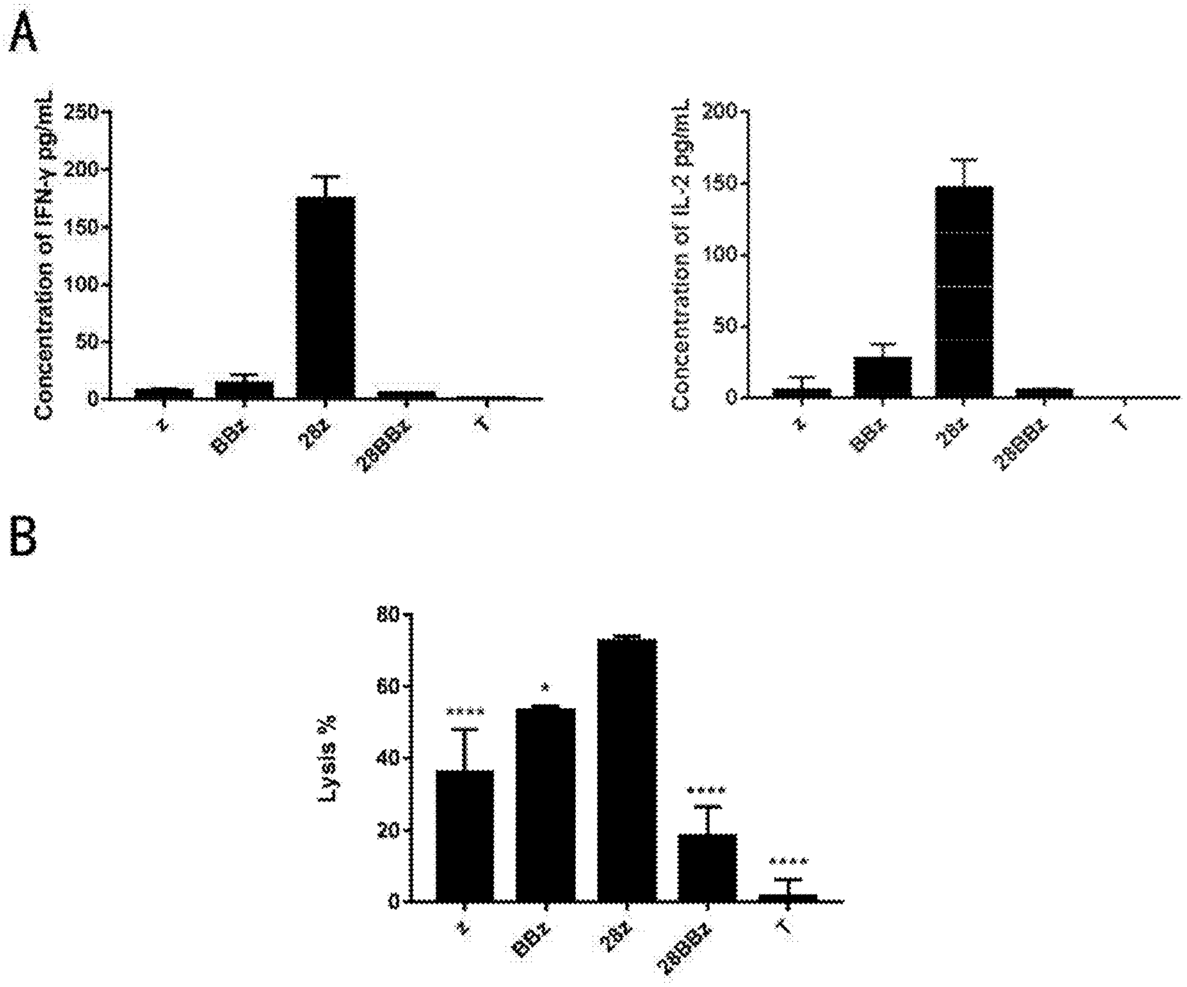
FIG. 2 shows the effects of CAR-T cells with different CAR structures.

As shown in FIG. 2, compared with P4-z, P4-BBz and P4-28BBz, P4-28z showed higher release of IFN-γ and IL-2 (FIG. 2A), and higher specific cell lysis (FIG. 2B, * means $P<0.05$, **** means $P<0.0001$).

CAR-T cells containing P4-28z, referred to as P4-CAR-T cells, were used in all the following experiments.

Example 2. The Effect of Editing Inhibitory Receptors in CAR-T Cells on Tumor Killing In this example, the inhibitory receptors TIGIT, BTLA, CD160, 2B4 and CD200R in CAR-T cells were knocked out through gene editing and their effects on tumor killing were studied.

Figure 3:
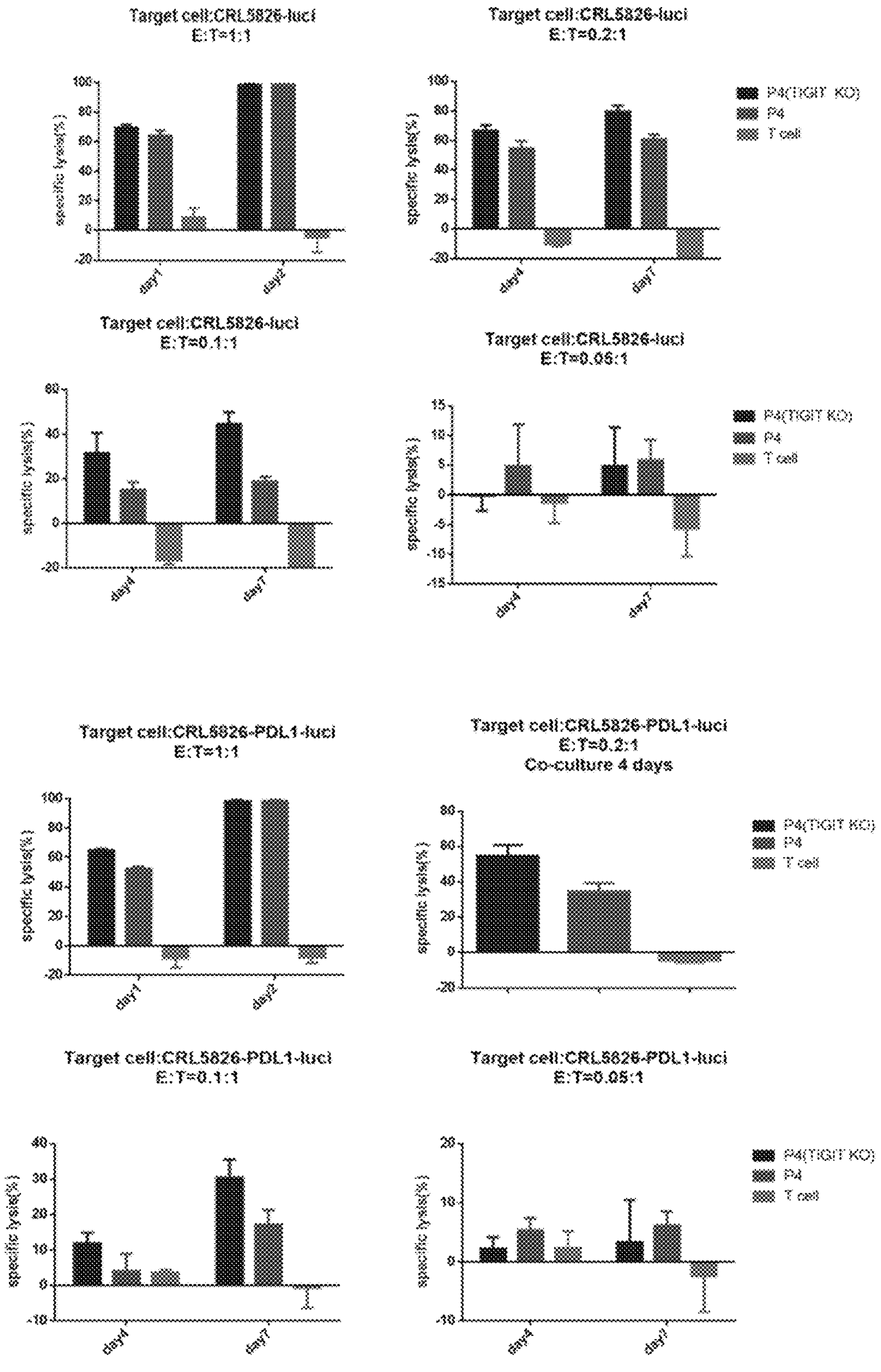
FIG. 3 shows the specific lysis of target cells CRL5826-luci and CRL5826-PDL1-luci by P4 CAR-T cells with TIGIT gene knocked out under different effector: target ratios and treatment times.

At a high-efficor: target ratio (1:1) and in a short term (24h, 48h), the TIGIT knock-out group showed a killing effect for CRL5826-luci and CRL5826-PDL1-luci not lower than that of the control CAR-T cells. For long-term and low-efficor: target ratio killing, it showed a stronger killing than the control CAR-T cells. (FIG. 3)

Figure 4:
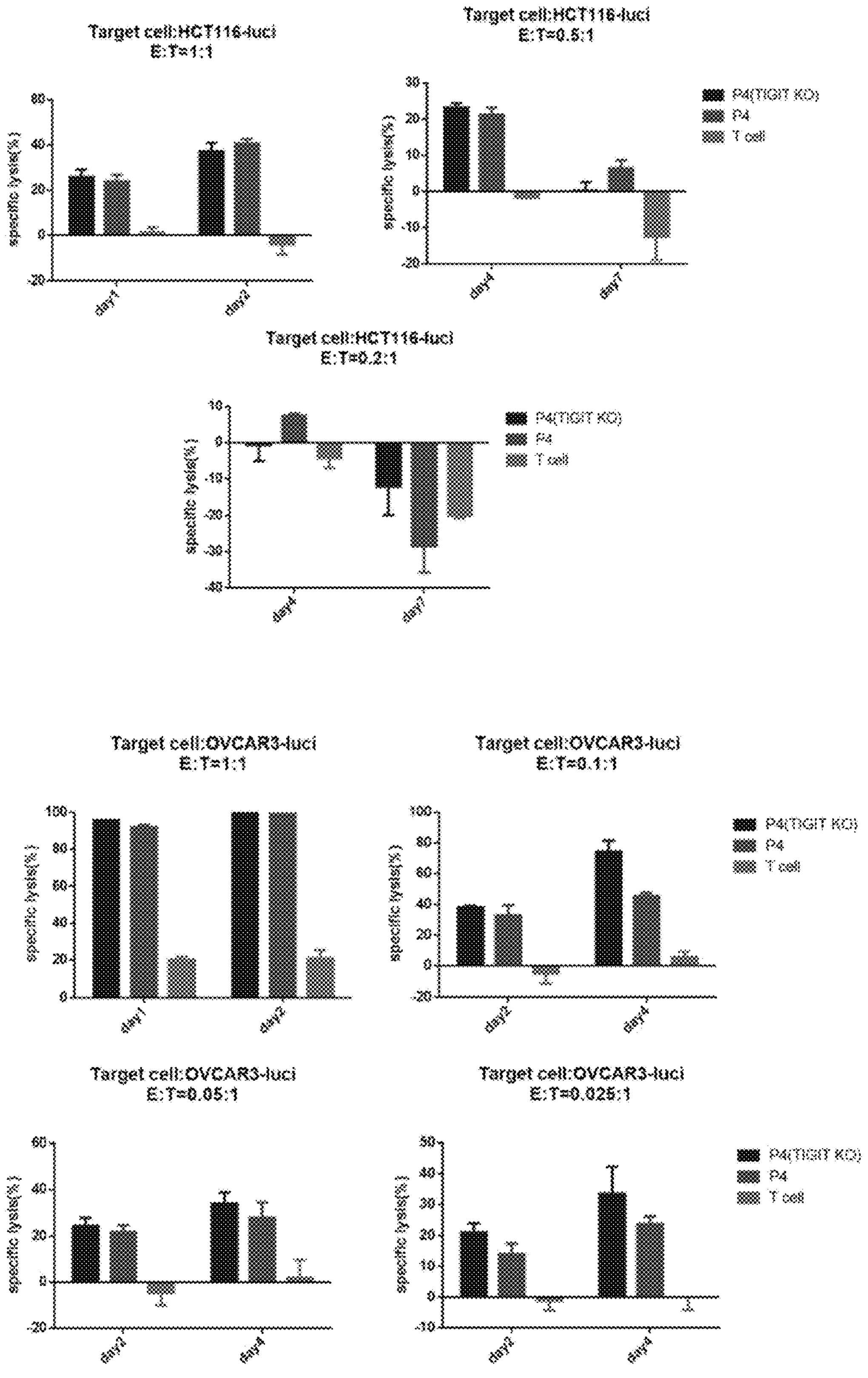
FIG. 4 shows the effect of TIGIT knocked-out P4 CAR-T cells on target cells HCT116-luci and OVCAR3-luci under different effector: target ratios and treatment times.

At high effector: target ratio (1:1) and in short term (24h, 48h), the TIGIT knock-out group showed a killing effect for OVCAR3-luci and HCT116-luci not lower than that of the control CAR-T cells. For long-term and low-efficor: target ratio killing, it showed a stronger killing than the control CAR-T cells. (FIG. 4)

Figure 5:
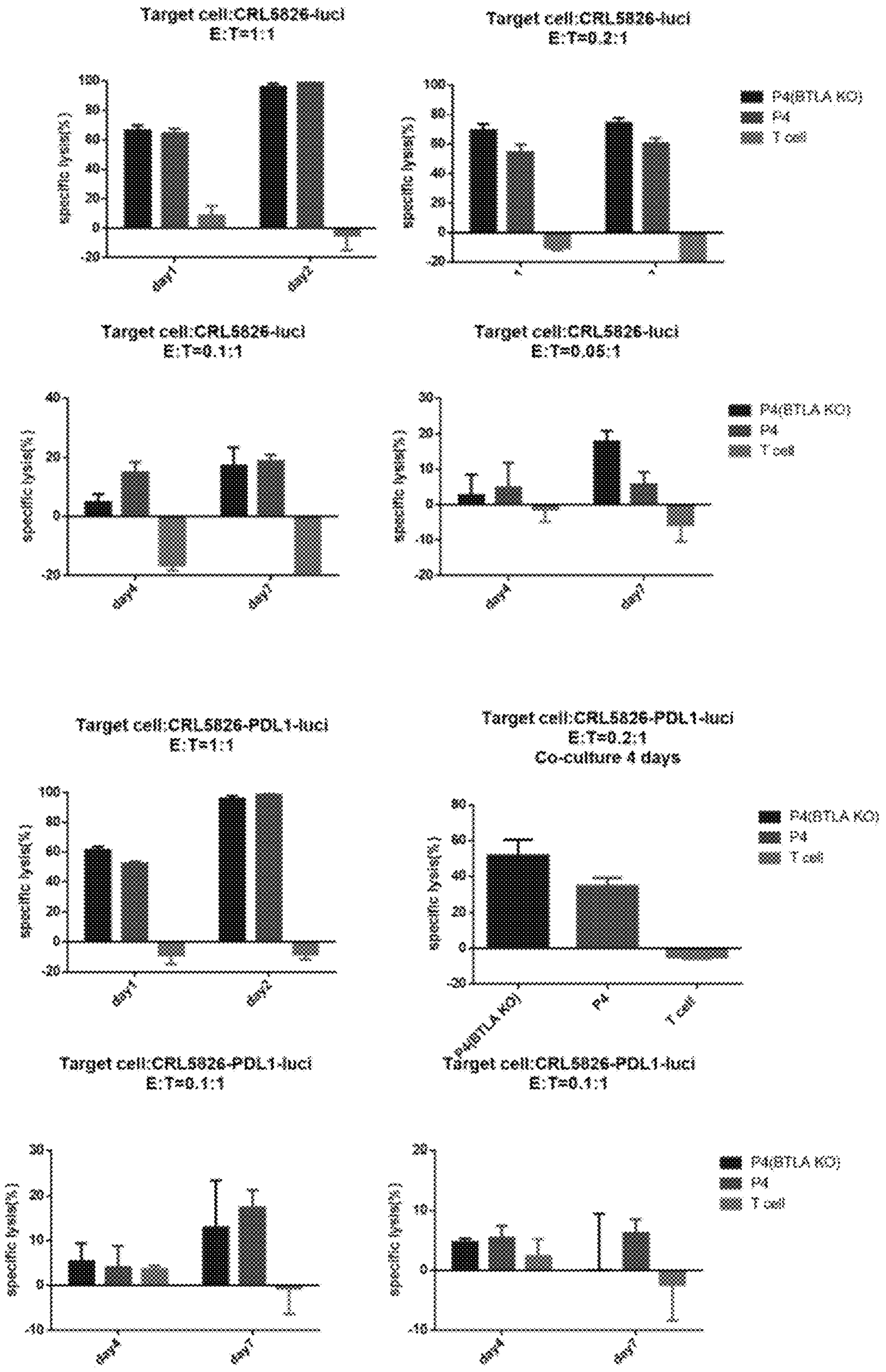
FIG. 5 shows the specific lysis of target cells CRL5826-luci and CRL5826-PDL1-luci by P4 CAR-T cells with BTLA gene knocked out under different effector: target ratios and treatment times.

At high effector: target ratio (1:1) and in short term (24h, 48h), the BTLA knock-out group showed a killing effect for CRL5826-luci and CRL5826-PDL1-luci not lower than that of the control CAR-T cells. For long-term and low-efficor: target ratio killing, it showed a stronger killing than the control CAR-T cells. (FIG. 5)

Figure 6:
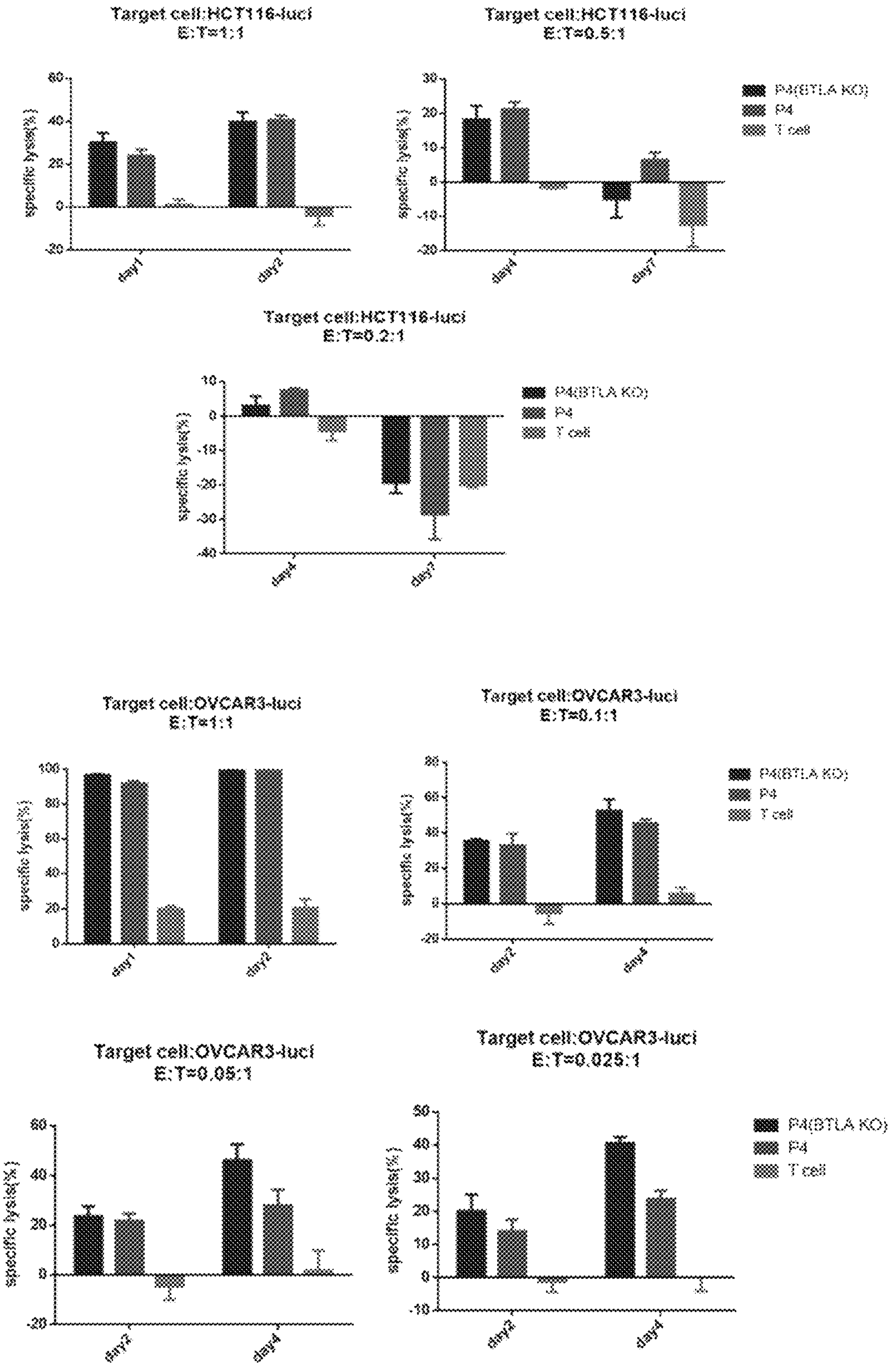
FIG. 6 shows the effect of BTLA knocked-out P4 CAR-T cells on target cells HCT116-luci and OVCAR3-luci under different effector: target ratios and treatment times.

At high effector: target ratio (1:1) and in short term (24h, 48h), the BTLA knock-out group showed a killing effect for OVCAR3-luci and HCT116-luci not lower than that of the control CAR-T cells. For long-term and low-efficor: target ratio killing, it showed a stronger killing than the control CAR-T cells. (FIG. 6)

Figure 7:
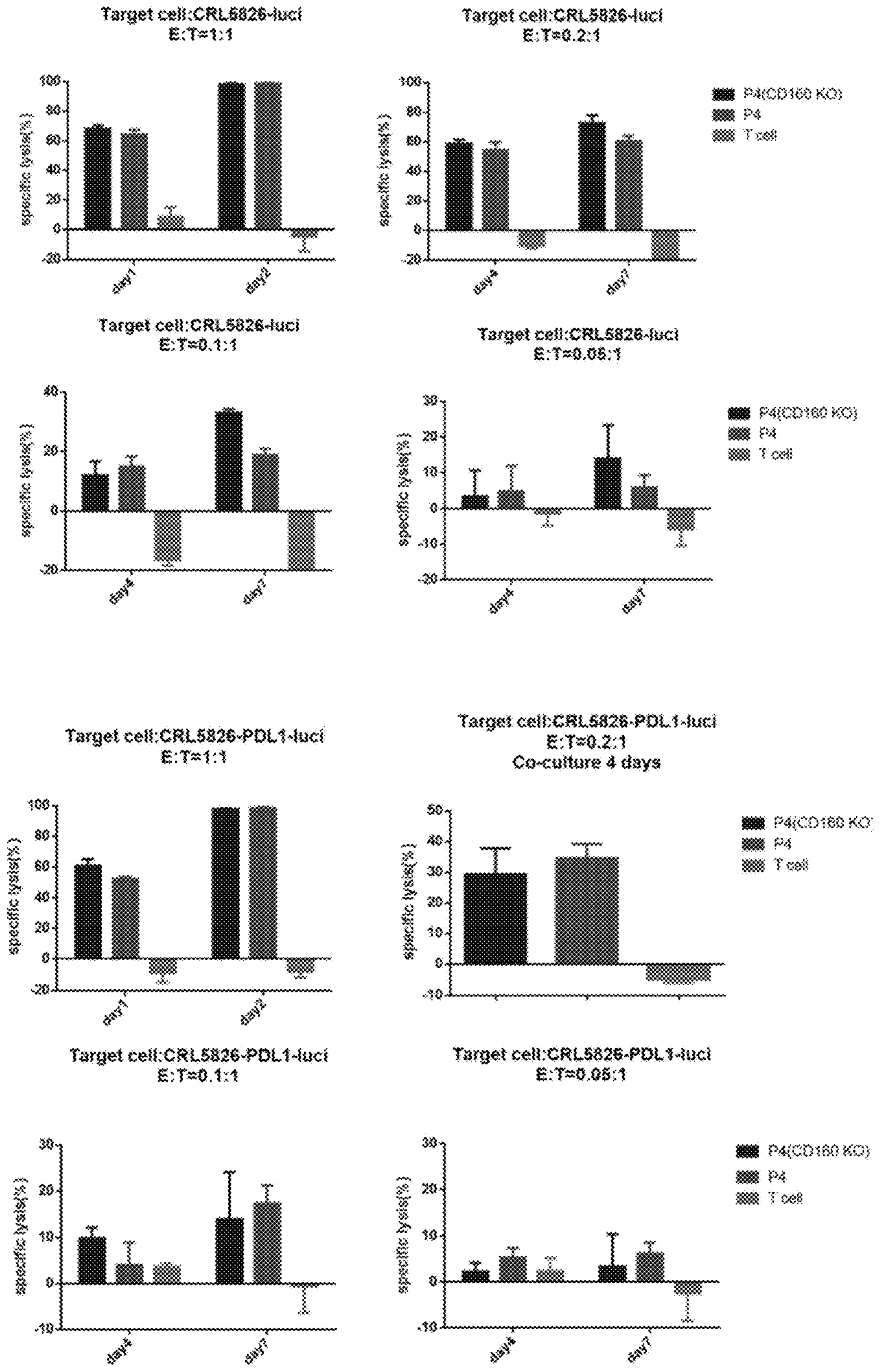
FIG. 7 shows the specific lysis of target cells CRL5826-luci and CRL5826-PDL1-luci by P4 CAR-T cells with CD160 gene knocked out under different effector: target ratios and treatment times.

At high effector: target ratio (1:1) and in short term (24h, 48h), the CD160 knock-out group showed a killing effect for CRL5826-luci and CRL5826-PDL1-luci not lower than that of the control CAR-T cells. For long-term and low-efficor: target ratio killing, it showed a stronger killing than the control CAR-T cells. (FIG. 7)

Figure 8:
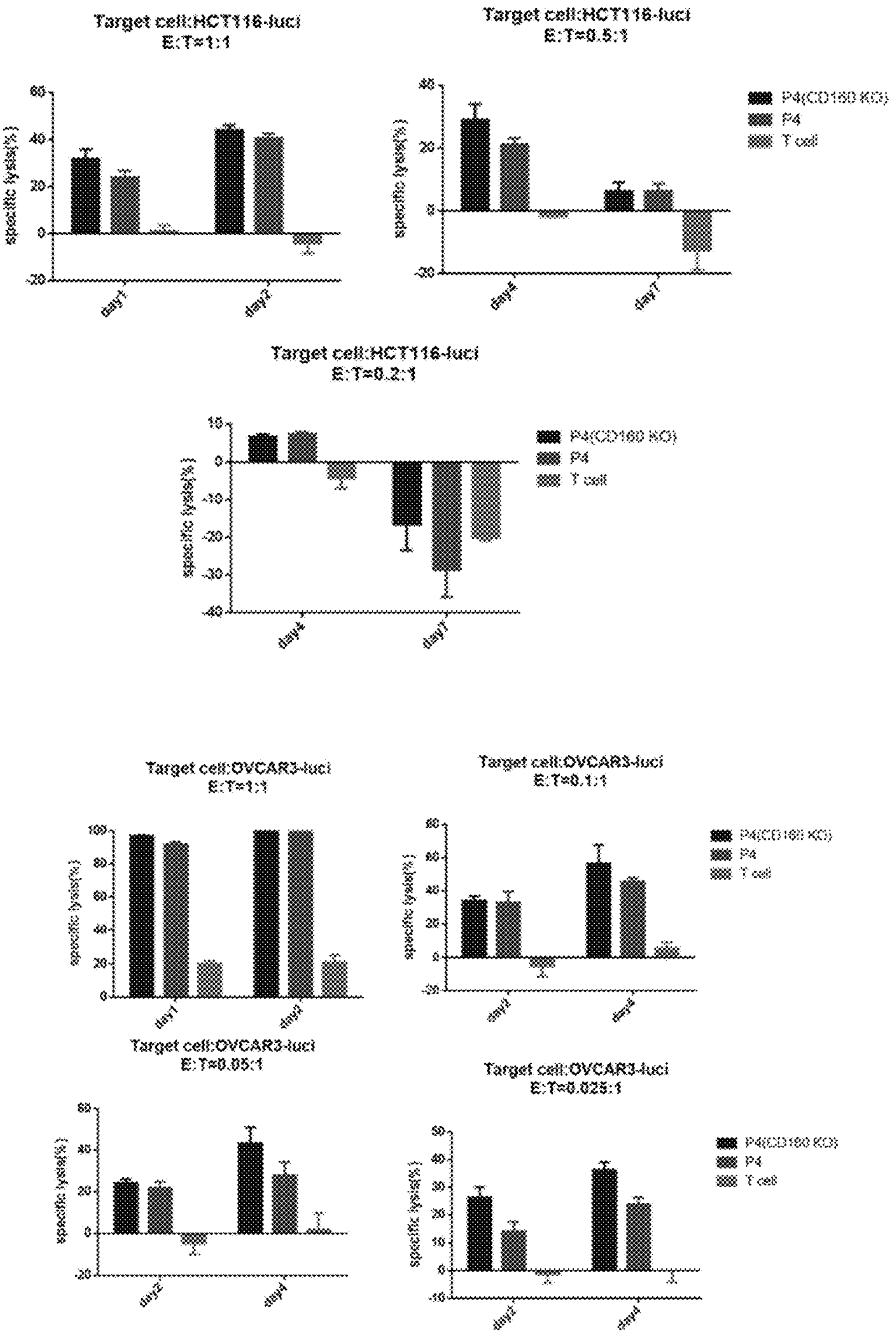
FIG. 8 shows the effect of CD160 knocked-out P4 CAR-T cells on target cells HCT116-luci and OVCAR3-luci under different effector: target ratios and treatment times.

At high effector: target ratio (1:1) and in short term (24h, 48h), the CD160 knock-out group showed a killing effect for OVCAR3-luci and HCT116-luci not lower than that of the control CAR-T cells. For long-term and low-efficor: target ratio killing, it showed a stronger killing than the control CAR-T cells. (FIG. 8)

Figure 9:
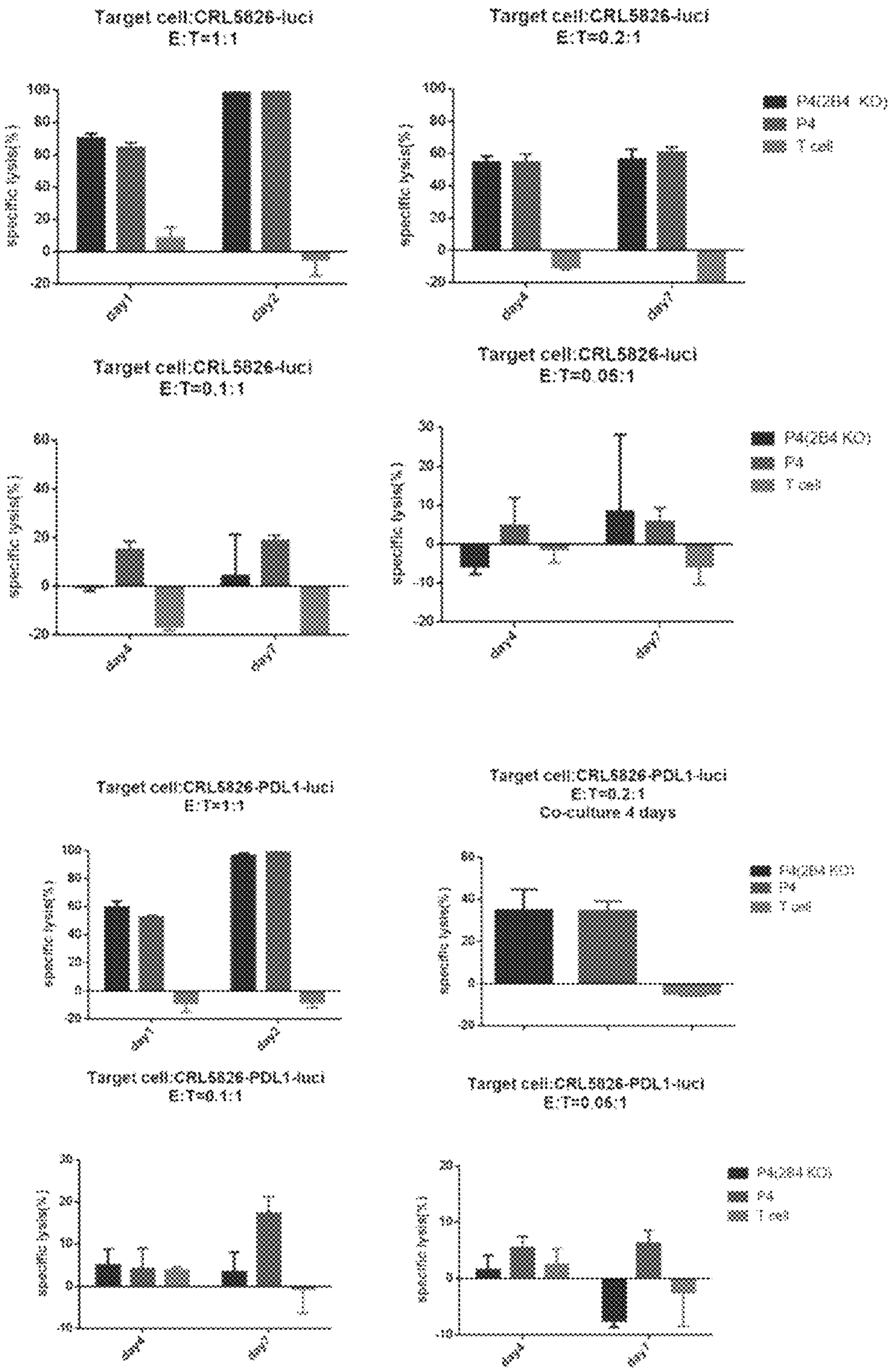
FIG. 9 shows the specific lysis of target cells CRL5826-luci and CRL5826-PDL1-luci by P4 CAR-T cells with 2B4 gene knocked-out under different effector: target ratios and treatment times.

At high effector: target ratio (1:1) and in short term (24h, 48h), the 2B4 knock-out group showed a killing effect for CRL5826-luci and CRL5826-PDL1-luci not lower than that of the control CAR-T cells. For long-term and low-efficor: target ratio killing, it showed a killing not lower than that of the control CAR-T cells. (FIG. 9)

Figure 10:
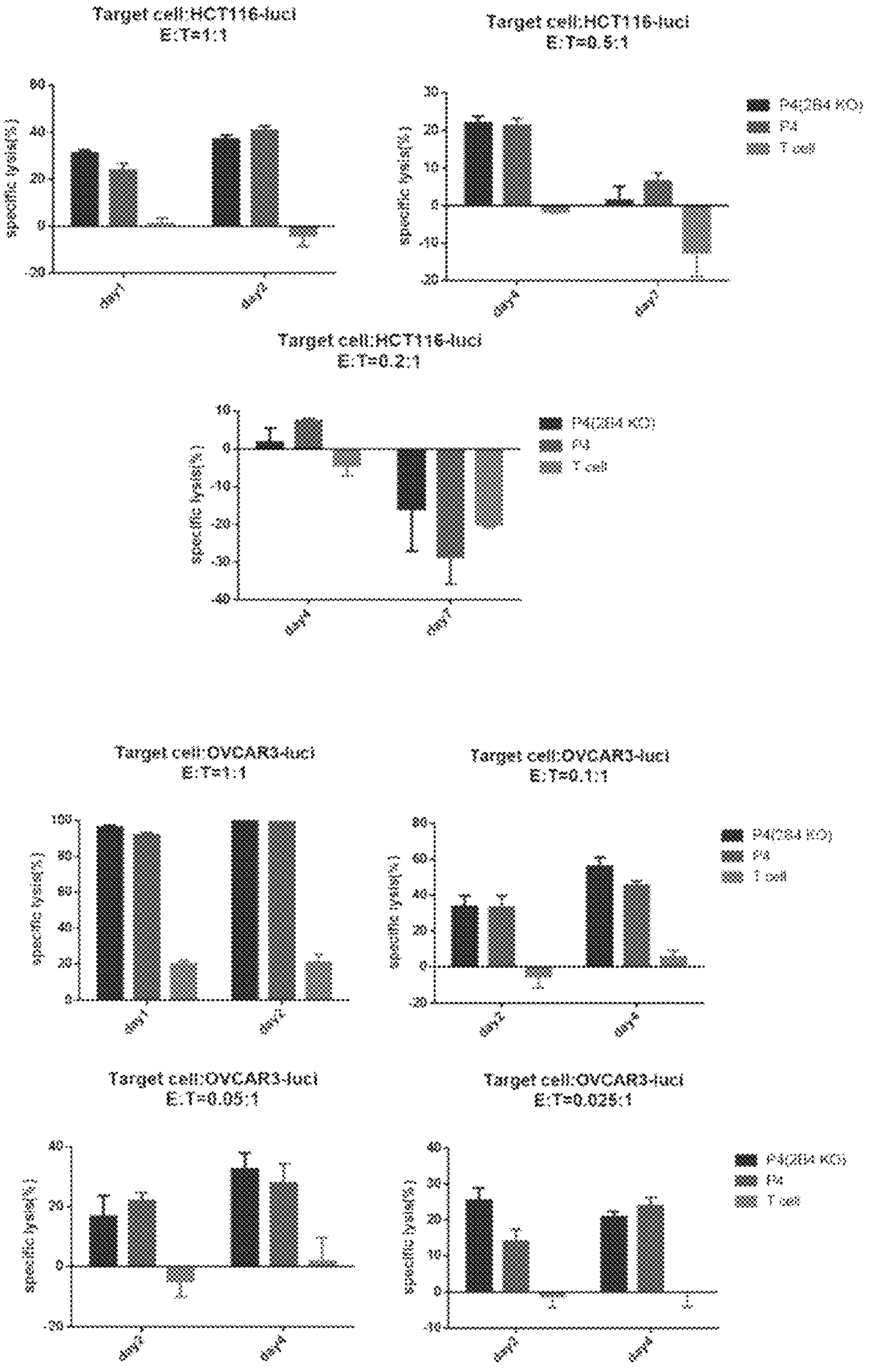
FIG. 10 shows the effect of 2B4 gene knocked-out P4 CAR-T cells on target cells HCT116-luci and OVCAR3-luci under different effector: target ratios and treatment times.

At high effector: target ratio (1:1) and in short term (24h, 48h), the 2B4 knock-out group showed a killing effect for OVCAR3-luci and HCT116-luci not lower than that of the control CAR-T cells. For long-term and low-efficor: target ratio killing, it showed a stronger killing than the control CAR-T cells. (FIG. 10)

Figure 11:
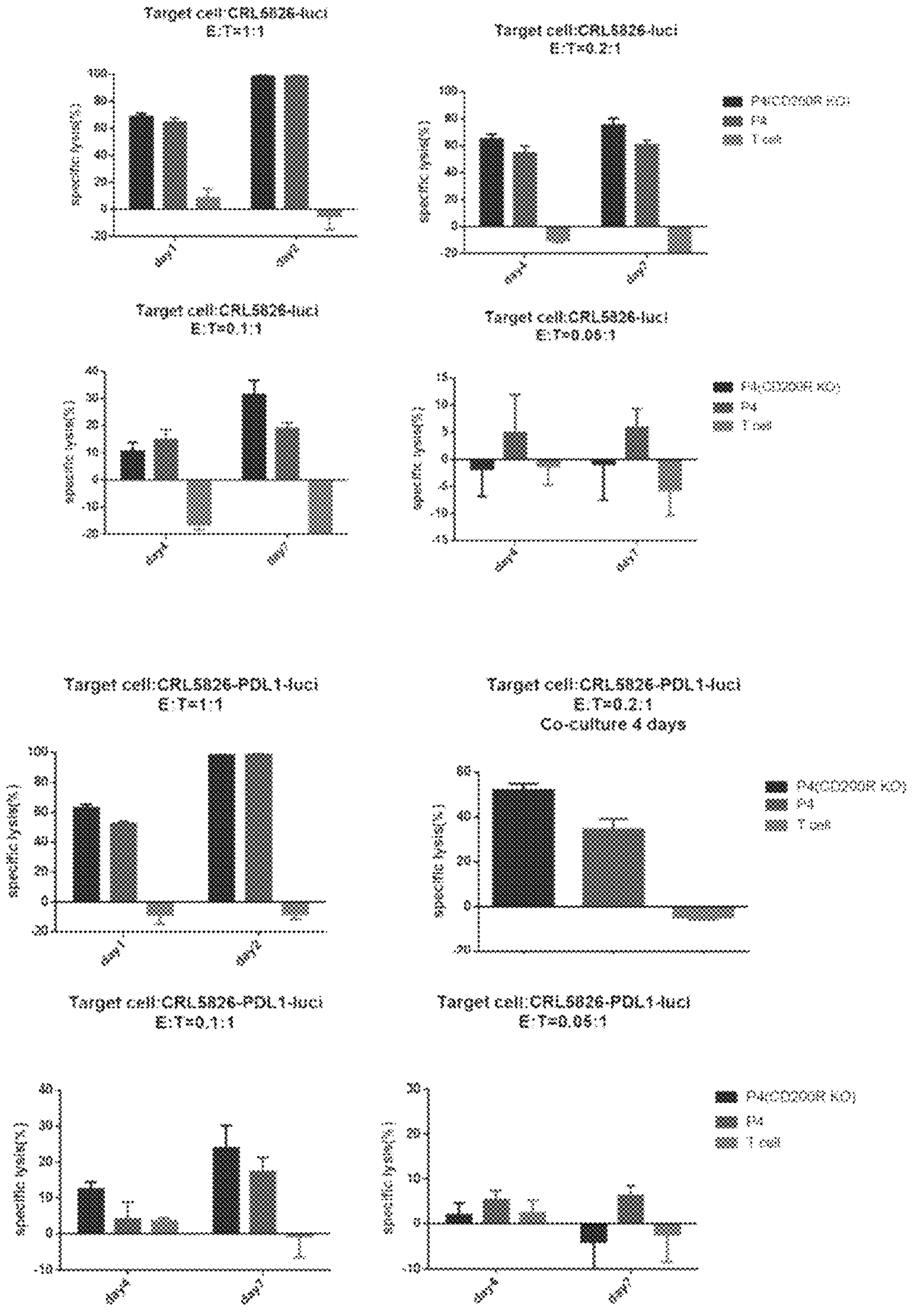
FIG. 11 shows the specific lysis of target cells CRL5826-luci and CRL5826-PDL1-luci by CD200R knocked-out P4 CAR-T cells under different effector: target ratios and treatment times.

At high effector: target ratio (1:1) and in short term (24h, 48h), the CD200R knock-out group showed a killing effect for CRL5826-luci and CRL5826-PDL1-luci not lower than that of the control CAR-T cells. For long-term and low-efficor: target ratio killing, it showed a stronger killing than the control CAR-T cells. (FIG. 11)

Figure 12:
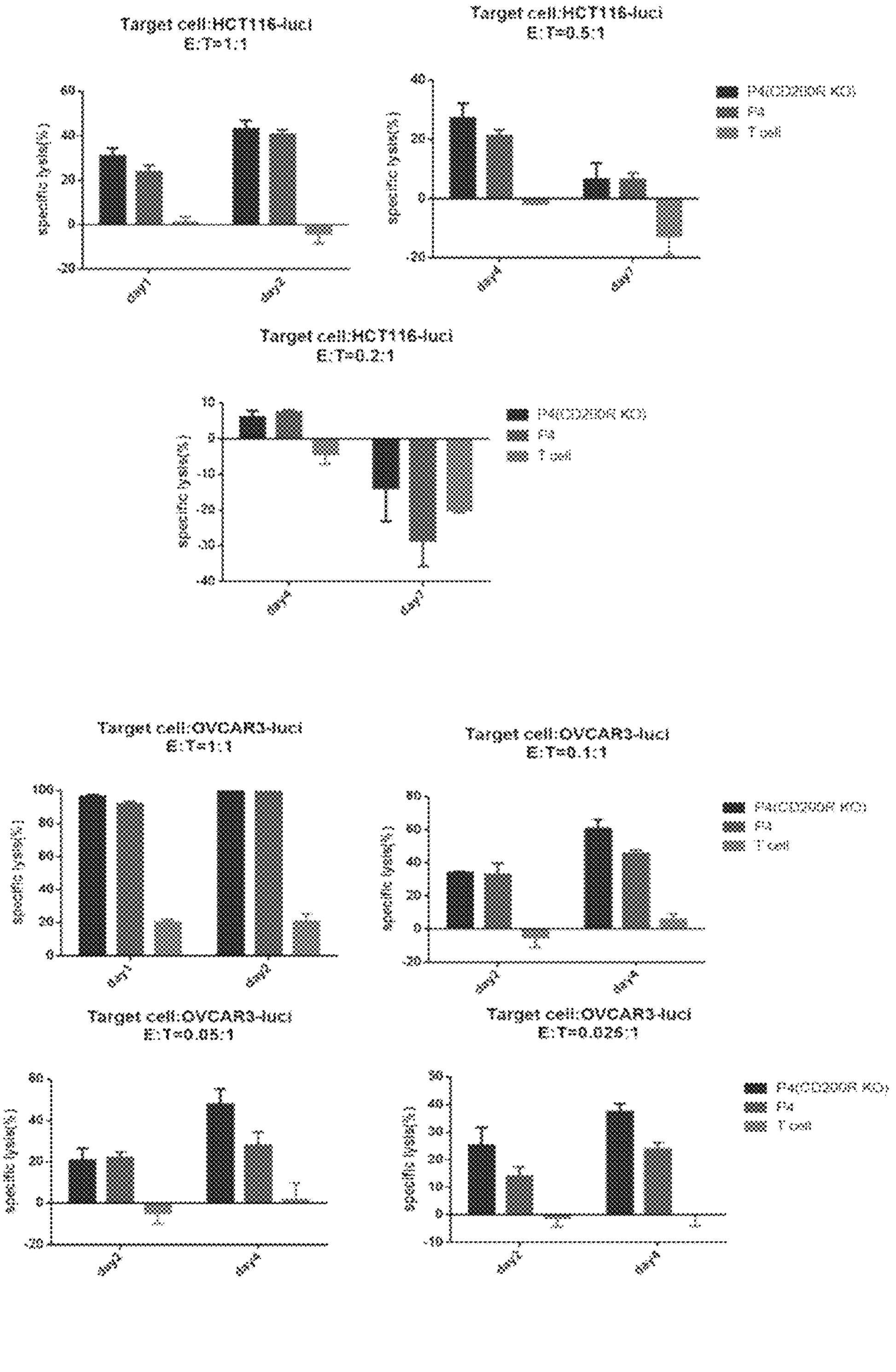
FIG. 12 shows the effects of CD200R knocked-out P4 CAR-T cells on target cells HCT116-luci and OVCAR3-luci under different effector: target ratios and treatment times.

At high effector: target ratio (1:1) and in short term (24h, 48h), the CD200R knock-out group showed a killing effect for OVCAR3-luci and HCT116-luci not lower than that of the control CAR-T cells. For long-term and low-efficor: target ratio killing, it showed a stronger killing than the control CAR-T cells. (FIG. 12)

Example 3. The Effect of Editing T Cell Exhaustion-Related Transcription Factors in CAR-T Cells on Tumor Killing In this example, the T cell exhaustion-related transcription factors BATF, GATA3, IRF4, and RARA in CAR-T cells were knocked out through gene editing and their effects on tumor killing were studied.

Figure 13:
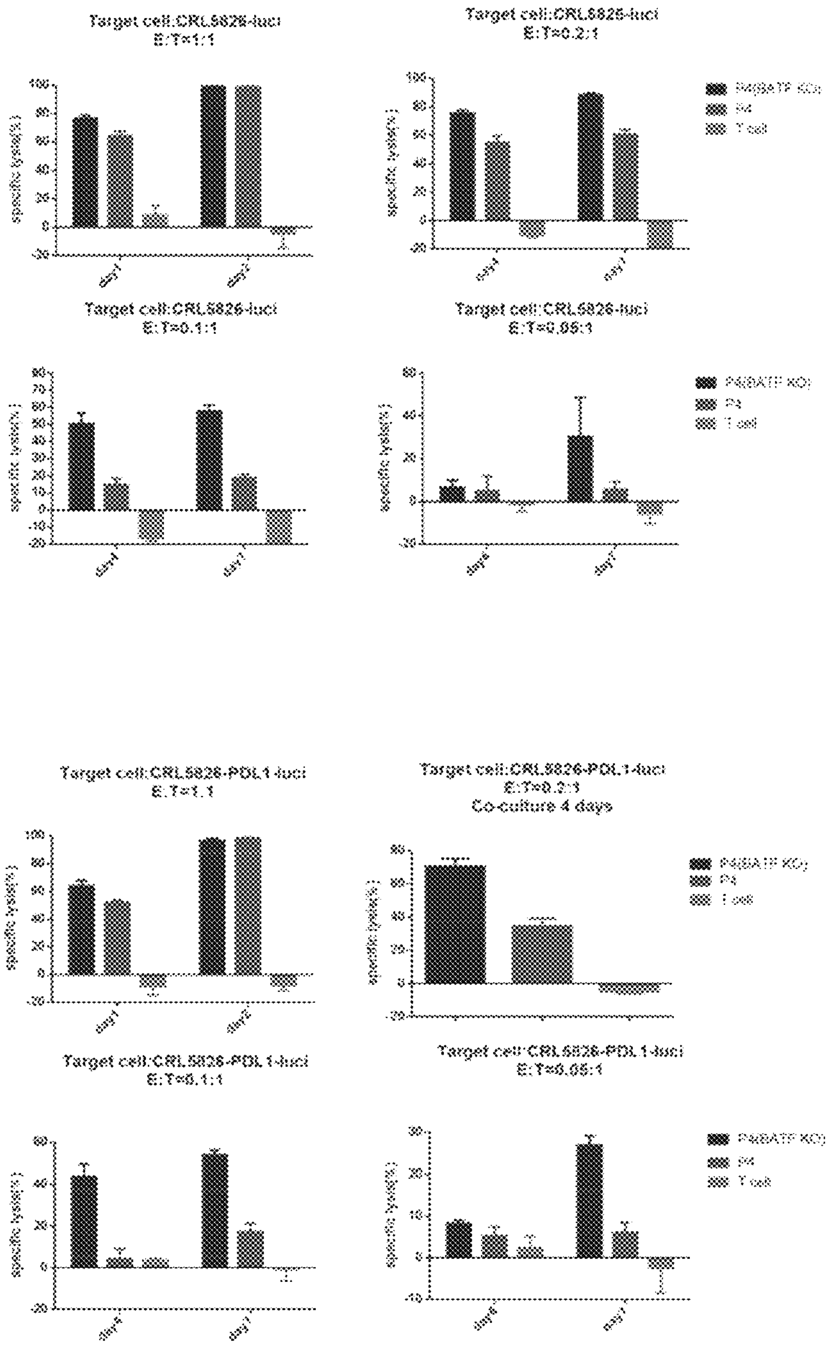
FIG. 13 shows the specific lysis of target cells CRL5826-luci and CRL5826-PDL1-luci by P4 CAR-T cells with BATF gene knocked out under different effector: target ratios and treatment times.

At high effector: target ratio (1:1) and in short term (24h, 48h), the BATF knock-out group showed a killing effect for CRL5826-luci and CRL5826-PDL1-luci not lower than that of the control CAR-T cells. For long-term and low-efficitor: target ratio killing, it showed a significantly stronger killing than the control CAR-T cells. (FIG. 13)

Figure 14:
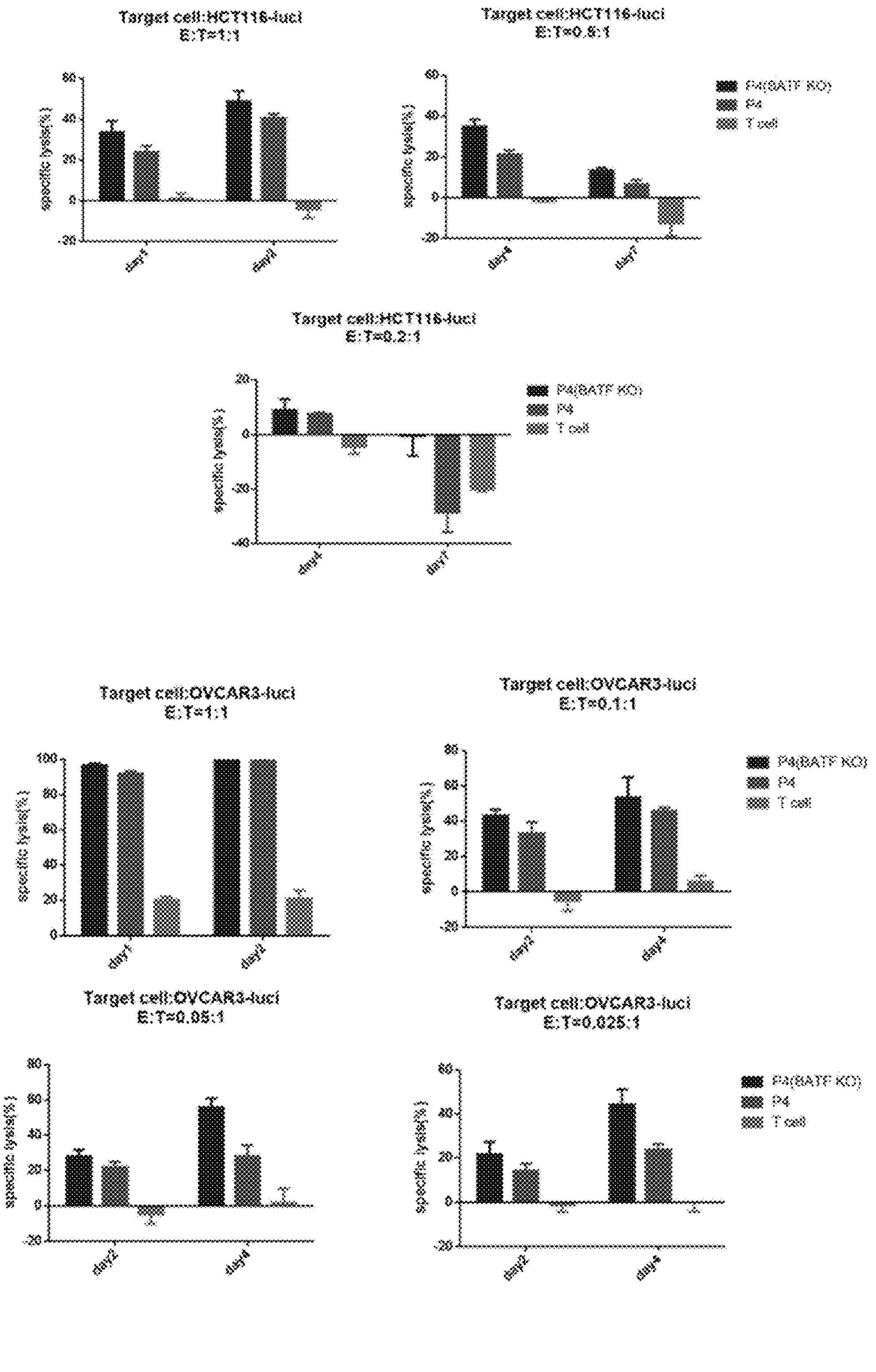
FIG. 14 shows the effects of P4 CAR-T cells with BATF gene knocked out on target cells HCT116-luci and OVCAR3-luci under different effector: target ratios and treatment times.

At high effector: target ratio (1:1) and in short term (24h, 48h), the BATF knock-out group showed a killing effect for OVCAR3-luci and HCT116-luci not lower than that of the control CAR-T cells. For long-term and low-efficitor: target ratio killing, it showed a significantly stronger killing than the control CAR-T cells. (FIG. 14)

Figure 15:
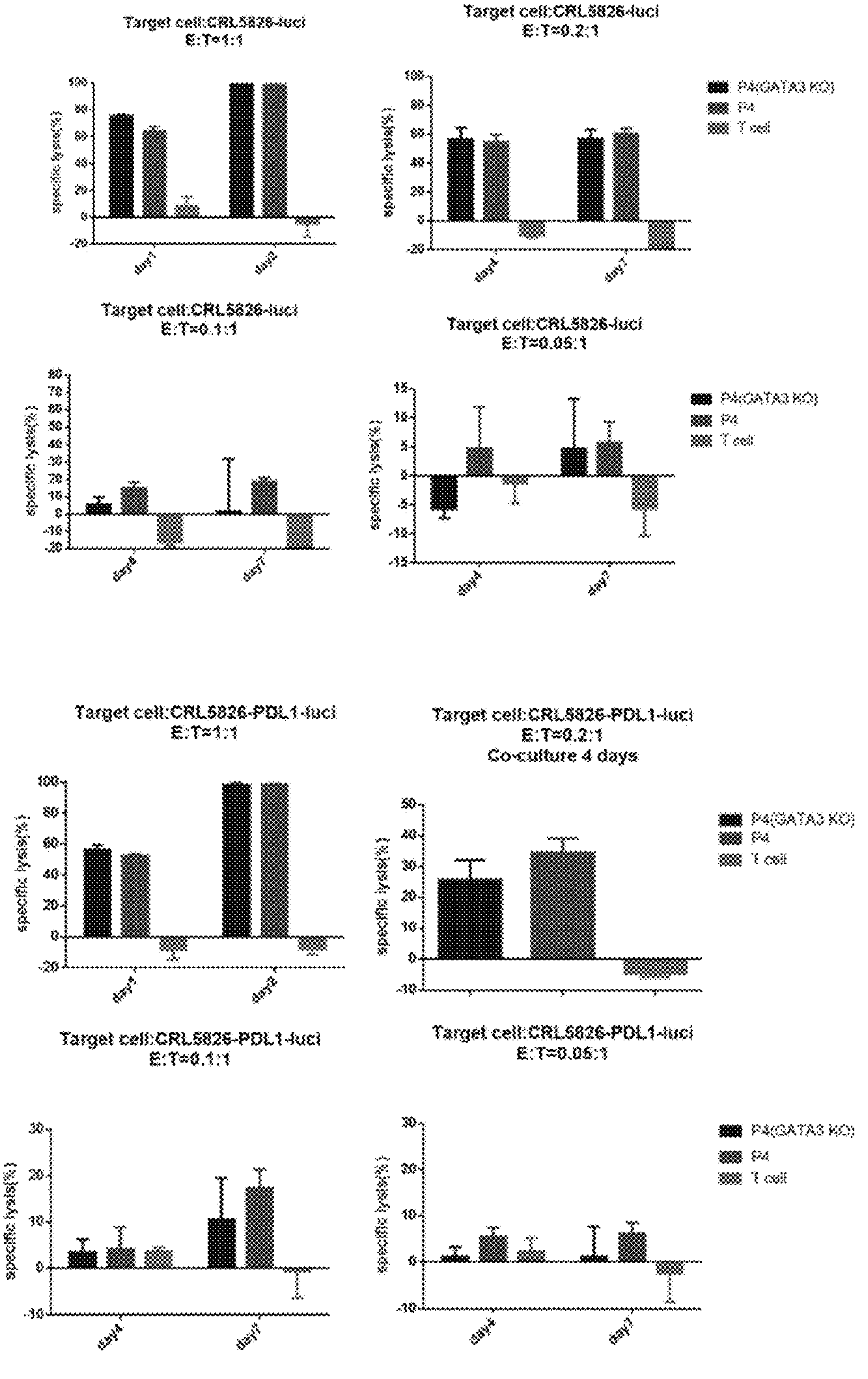
FIG. 15 shows the specific lysis of target cells CRL5826-luci and CRL5826-PDL1-luci by P4 CAR-T cells with GATA3 gene knocked out under different effector: target ratios and treatment times.

At high effector: target ratio (1:1) and in short term (24h, 48h), the GATA3 knock-out group showed a killing effect for CRL5826-luci and CRL5826-PDL1-luci not lower than that of the control CAR-T cells. For long-term and low-efficitor: target ratio killing, it showed a killing not lower than that of the control CAR-T cells. (FIG. 15)

Figure 16:
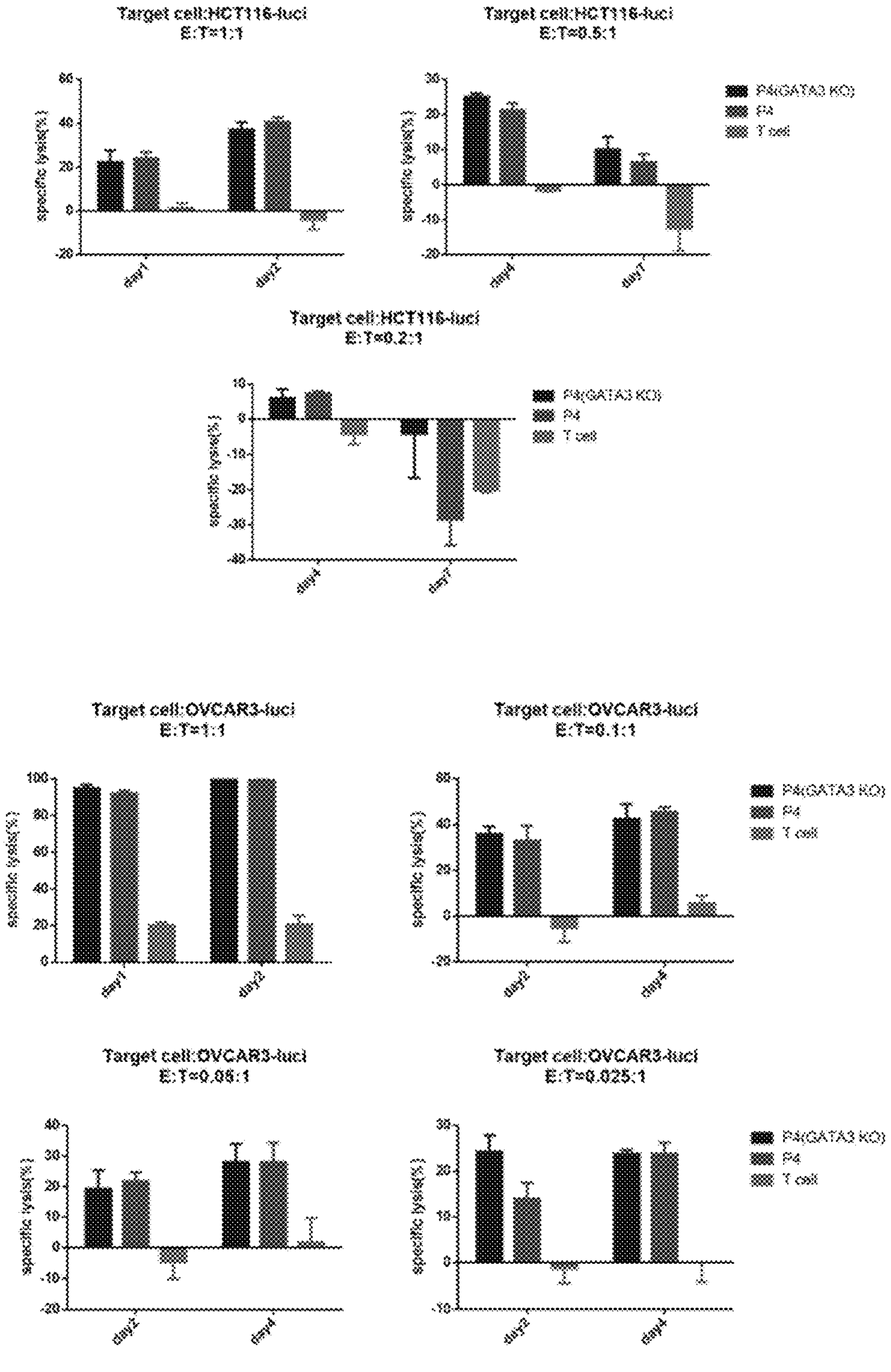
FIG. 16 shows the effects of GATA3 knocked-out P4 CAR-T cells on target cells HCT116-luci and OVCAR3-luci under different effector: target ratios and treatment times.

At high effector: target ratio (1:1) and in short term (24h, 48h), the GATA3 knock-out group showed a killing effect for OVCAR3-luci and HCT116-luci not lower than that of the control CAR-T cells. For long-term and low-efficitor: target ratio killing, it showed a killing not lower than that of the control CAR-T cells. (FIG. 16)

Figure 17:
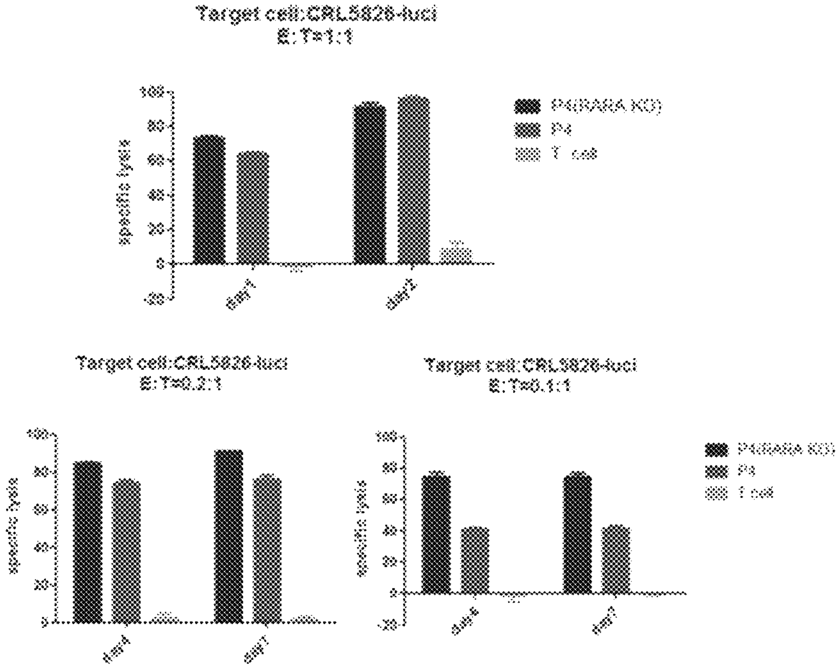
FIG. 17 shows the specific lysis of the target cell CRL5826-luci by P4 CAR-T cells with RARA gene knocked out under different effector: target ratios and treatment times.

At high effector: target ratio (1:1) and in short term (24h, 48h), the RARA knock-out group showed a killing effect for CRL5826-luci not lower than that of the control CAR-T cells. At 0.2:1, the killing of the knock-out group on the fourth and seventh days achieved above 70%, not lower than that of the control CAR-T cells. At an effector: target ratio reduced to 0.1:1, the killing of the RARA knock-out group on the fourth and seventh days was stronger than the control CAR-T cells. (FIG. 17)

Figure 45:
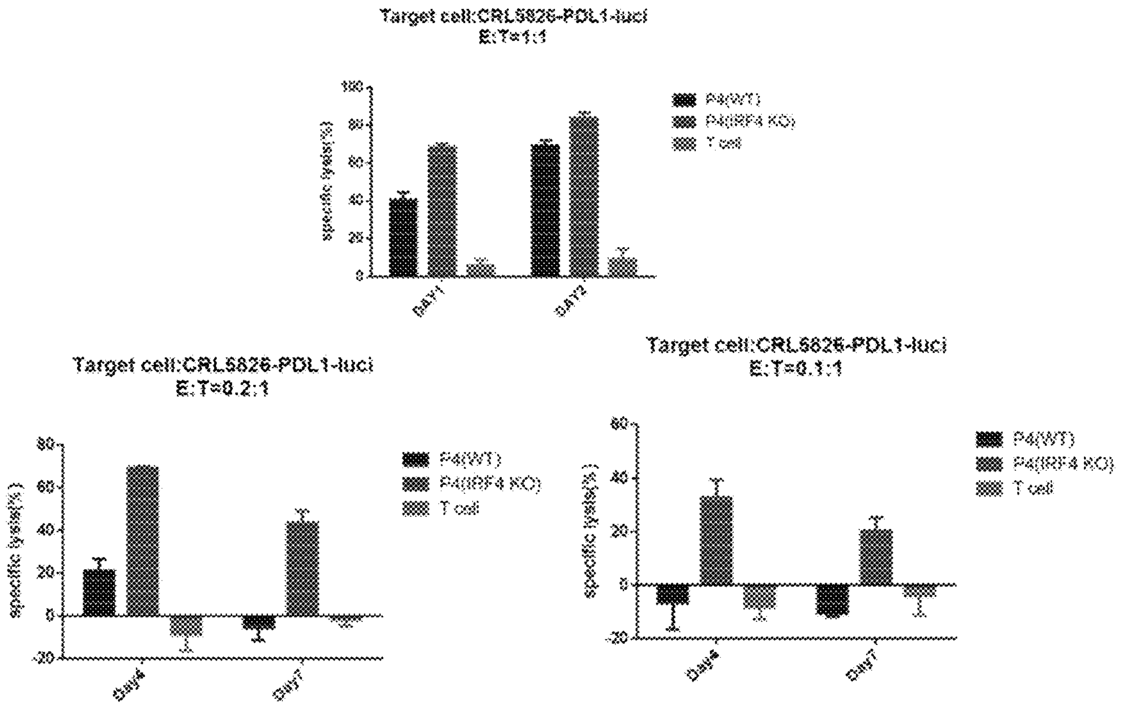
FIG. 45 shows the specific lysis of target cells CRL5826-PDL1-luci by P4 CAR-T cells with IRF4 gene knocked out under different effector: target ratios and treatment times.

At high effector: target ratio (1:1) and in short term (24h, 48h), the IRF4 knock-out group showed a killing effect for CRL5826-luci not lower than that of the control CAR-T cells. At 0.2:1, the killing of the knock-out group on the fourth and seventh days was stronger than that of the control CAR-T cells. At an effector: target ratio reduced to 0.1:1, the killing of the IRF4 knock-out group on the fourth and seventh days was stronger than the control CAR-T cells. (FIG. 45)

Example 4. The Effect of Editing Tumor Microenvironment-Related Receptors in CAR-T Cells on Tumor Killing In this example, the tumor microenvironment-related receptors A2aR, IL10RA, and ADRB2 in CAR-T cells were knocked out through gene editing and their effects on tumor killing were studied.

Figure 18:
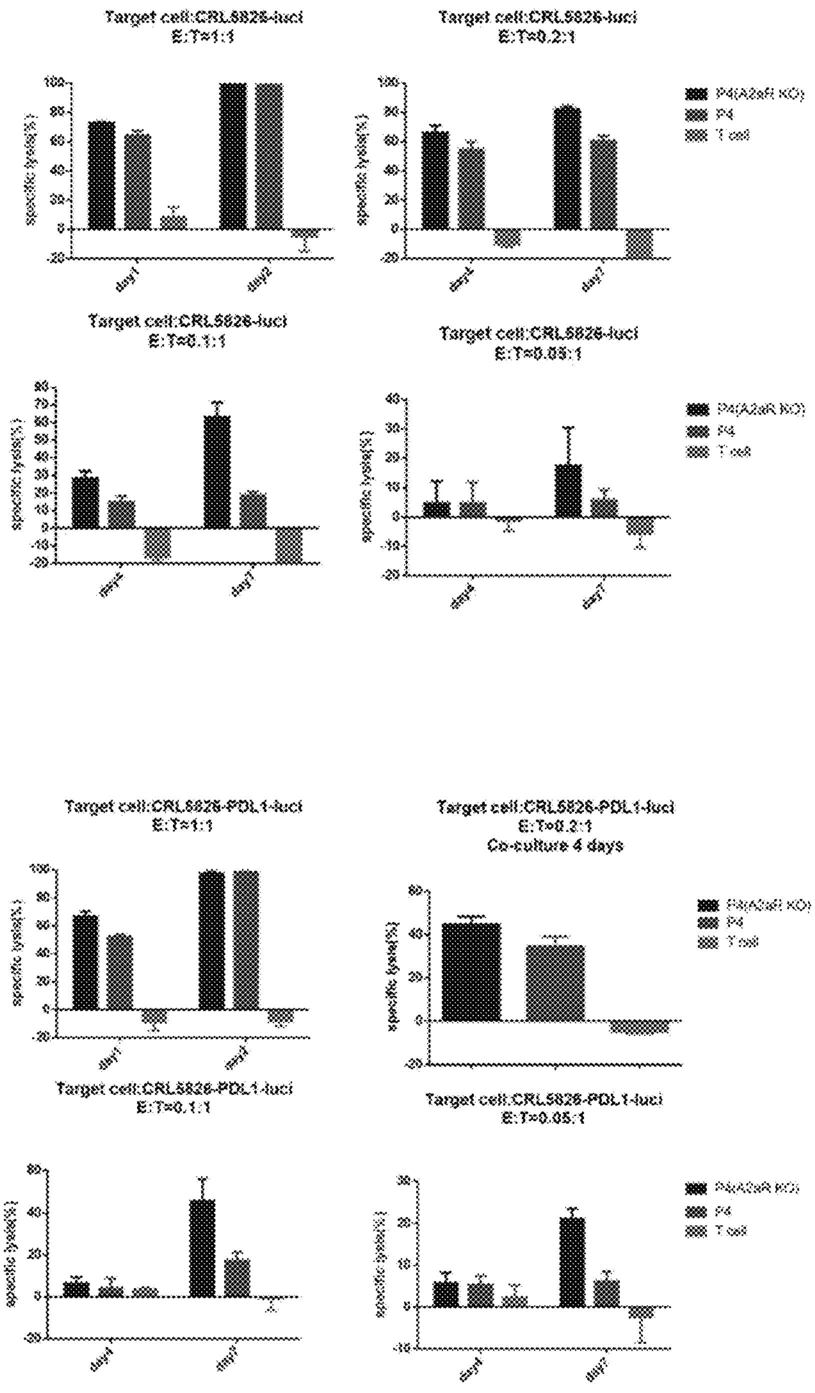
FIG. 18 shows the specific lysis of target cells CRL5826-luci and CRL5826-PDL1-luci by A2aR knocked-out P4 CAR-T cells under different effector: target ratios and treatment times.

At high effector: target ratio (1:1) and in short term (24h, 48h), the A2aR knock-out group showed a killing effect for CRL5826-luci and CRL5826-PDL1-luci not lower than that of the control CAR-T cells. For long-term and low-efficitor: target ratio killing, it showed a killing significantly stronger than that of the control CAR-T cells. (FIG. 18)

Figure 19:
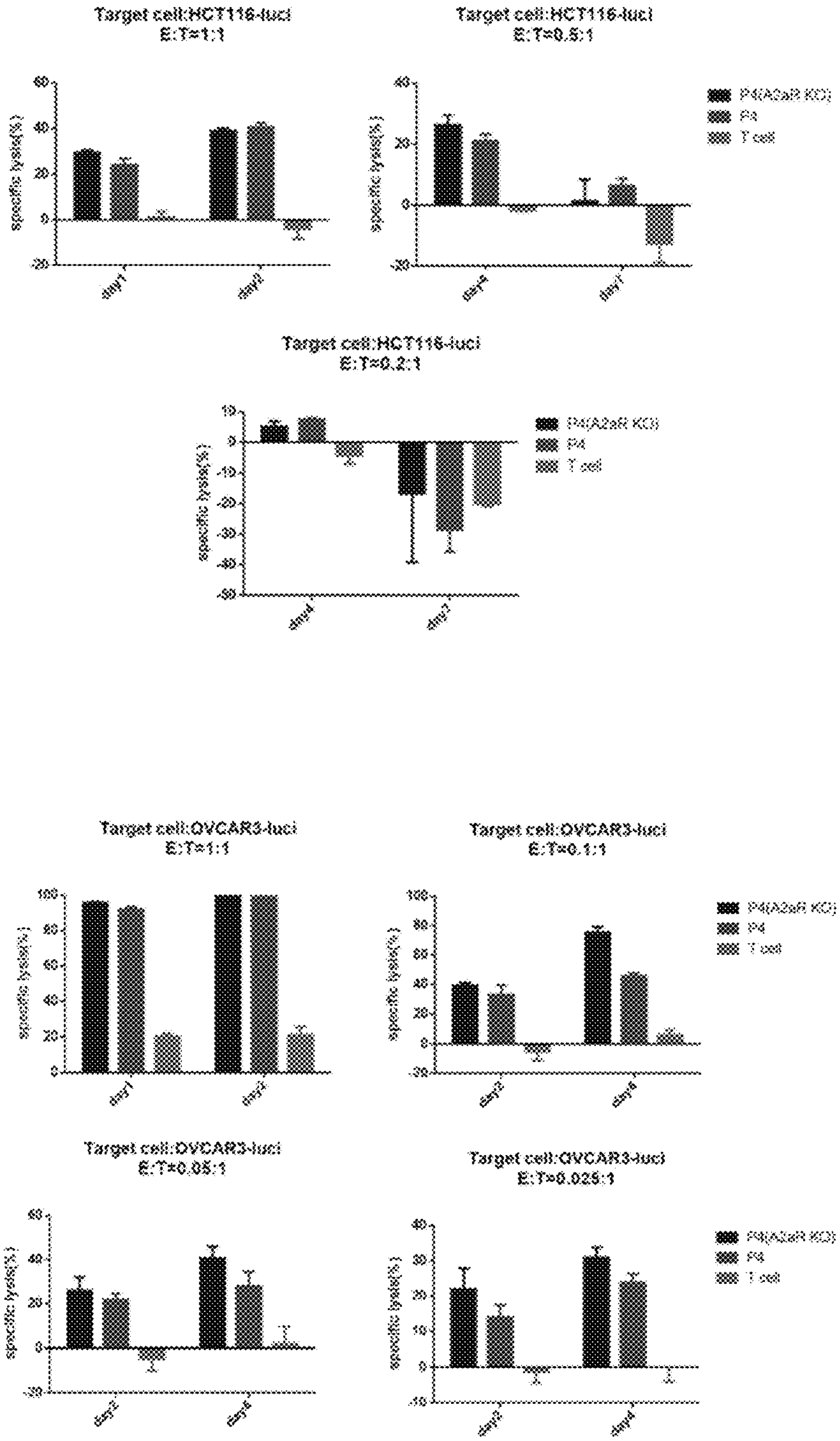
FIG. 19 shows the effect of A2aR knocked-out P4 CAR-T cells on target cells HCT116-luci and OVCAR3-luci under different effector: target ratios and treatment times.

At high effector: target ratio (1:1) and in short term (24h, 48h), the A2aR knock-out group showed a killing effect for OVCAR3-luci and HCT116-luci not lower than that of the control CAR-T cells. For long-term and low-efficitor: target ratio killing, it showed a killing stronger than that of the control CAR-T cells. (FIG. 19)

Figure 20:
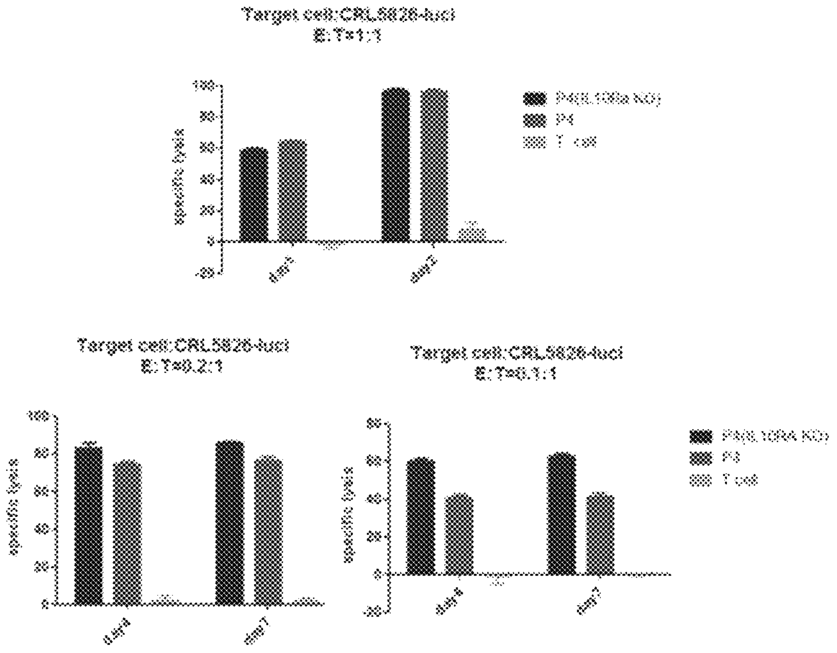
FIG. 20 shows the specific lysis of target cells CRL5826-luci by IL10Ra knocked-out P4 CAR-T cells under different effector: target ratios and treatment times.

At high effector: target ratio (1:1) and in short term (24h, 48h), the IL10RA knock-out group showed a killing effect for CRL5826-luci not lower than that of the control CAR-T cells. At lower effector: target ratio of 0.2:1, the killing of the knock-out group on the fourth and seventh days achieved above 70%, not lower than that of the control CAR-T cells. At an effector: target ratio reduced to 0.1:1, the killing of the IL10RA knock-out group on the fourth and seventh days was stronger than the control CAR-T cells. (FIG. 20)

Figure 21:
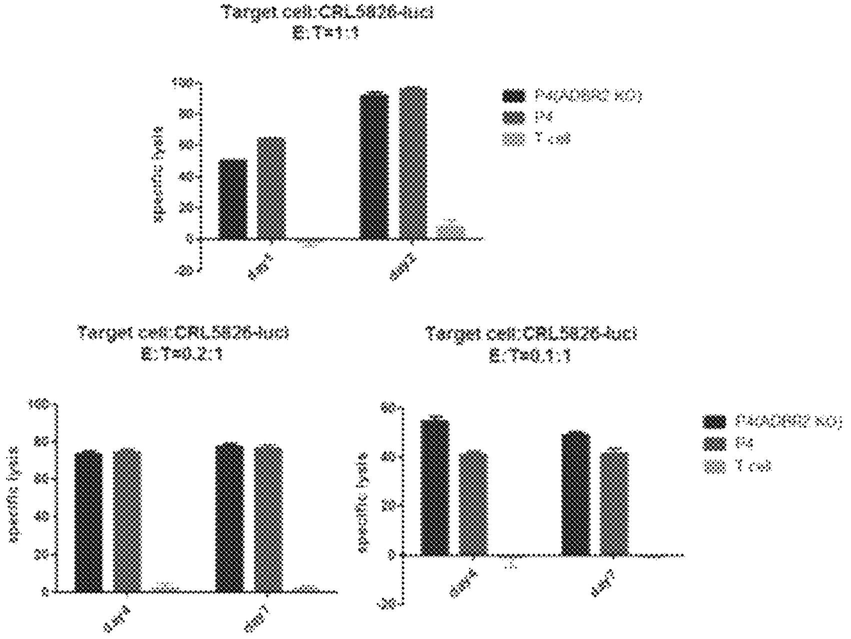
FIG. 21 shows the specific lysis of target cells CRL5826-luci by ADRB2 knocked-out P4 CAR-T cells under different effector: target ratios and treatment times.

At high effector: target ratio (1:1) and in short term (24h, 48h), the ADRB2 knock-out group showed a killing effect for CRL5826-luci not lower than that of the control CAR-T cells. At lower effector: target ratio of 0.2:1, the killing of the knock-out group on the fourth and seventh days achived above 70%, not lower than that of the control CAR-T cells. At an effector: target ratio reduced to 0.1:1, the killing of the ADRB2 knock-out group on the fourth and seventh days was stronger than the control CAR-T cells. (FIG. 21)

Example 5 the Effect of Editing Epigenetic Genes Related to T Cell Exhaustion in CAR-T Cells on Tumor Killing In this example, the T cell exhaustion-related epigenetic genes such as methyltransferase DNMT3A in CAR-T cells were knocked out through gene editing and their effects on tumor killing were studied.

Figure 22:
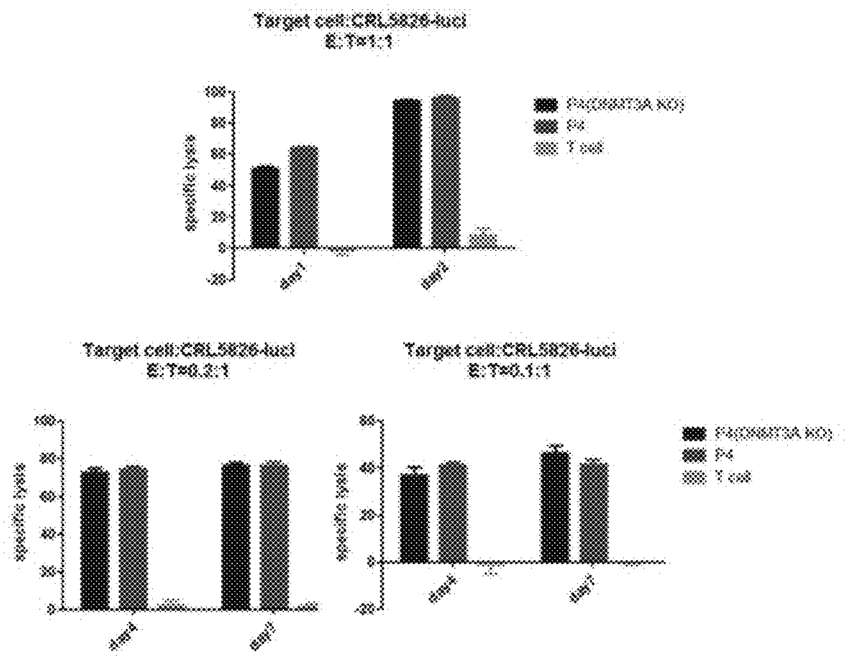
FIG. 22 shows the specific lysis of target cells CRL5826-luci by P4 CAR-T cells with DNMT3A gene knocked out under different effector: target ratios and treatment times.

At high effector: target ratio (1:1) and in short term (24h, 48h), the DNMT3A knock-out group showed a killing effect for CRL5826-luci not lower than that of the control CAR-T cells. At lower effector: target ratio of 0.2:1, the killing of the knock-out group on the fourth and seventh days achived above 70%, not lower than that of the control CAR-T cells. At an effector: target ratio reduced to 0.1:1, the killing of the DNMT3A knock-out group on the fourth and seventh days was slightly stronger than the control CAR-T cells. (FIG. 22)

Example 6: The Effect of Editing Genes Over-Expressed in Exhausted T Cells in CAR-T Cells on Tumor Killing In this example, some genes with unknown functions that are highly expressed in exhausted T cells in CAR-T cells were knocked out through gene editing and their effects on tumor killing were studied. These genes include: LAYN, MY07A, PHLDA1, RGS1, RGS2.

Figure 23:
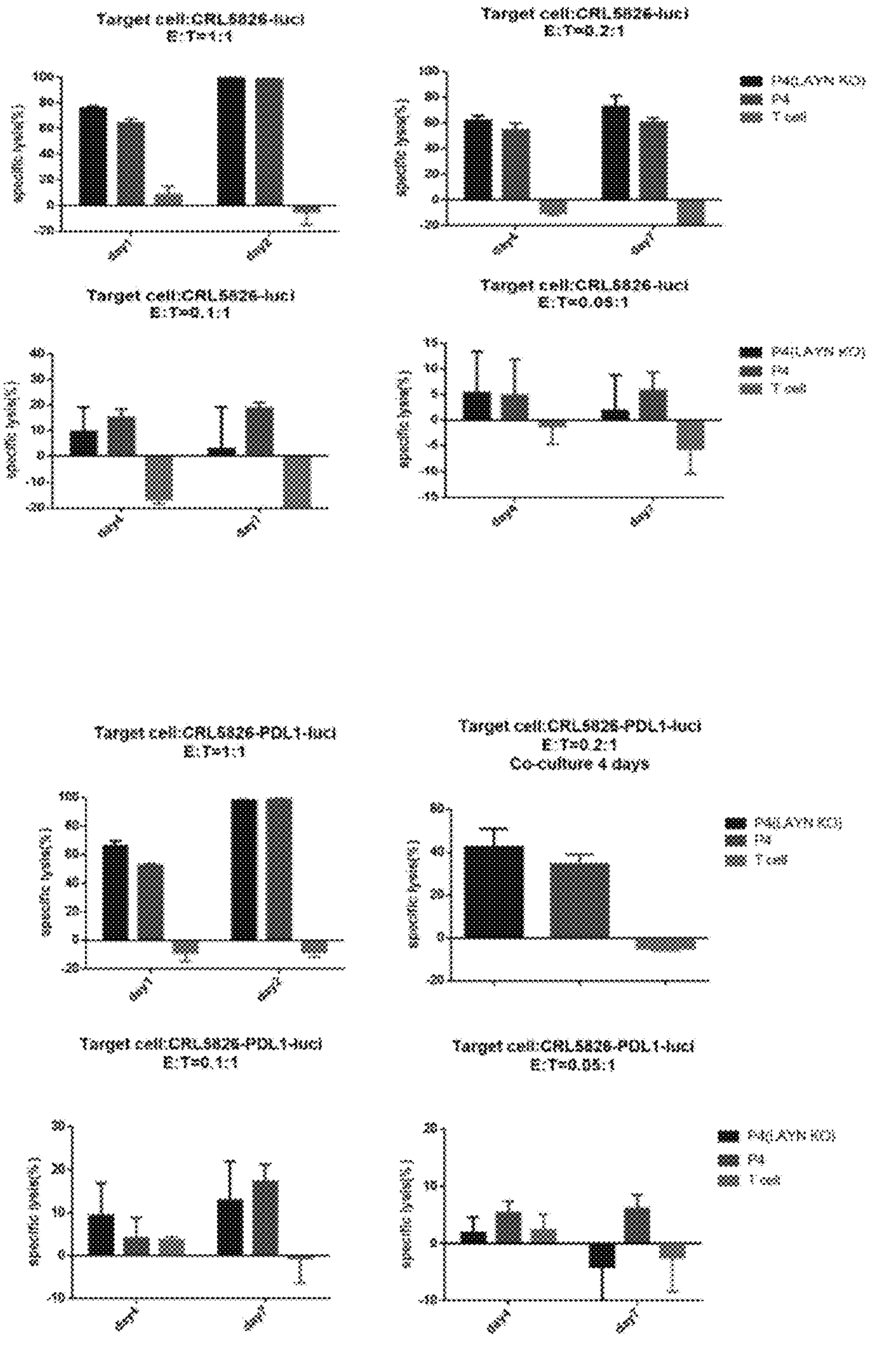
FIG. 23 shows the specific lysis of target cells CRL5826-luci and CRL5826-PDL1-luci by P4 CAR-T cells knocked out of LAYN gene under different effector: target ratios and treatment times.

At high effector: target ratio (1:1) and in short term (24h, 48h), the LAYN knock-out group showed a killing effect for CRL5826-luci and CRL5826-PDL1-luci not lower than that of the control CAR-T cells. For long-term and low-efficitor: target ratio killing, it showed a killing not lower than that of the control CAR-T cells. (FIG. 23)

Figure 24:
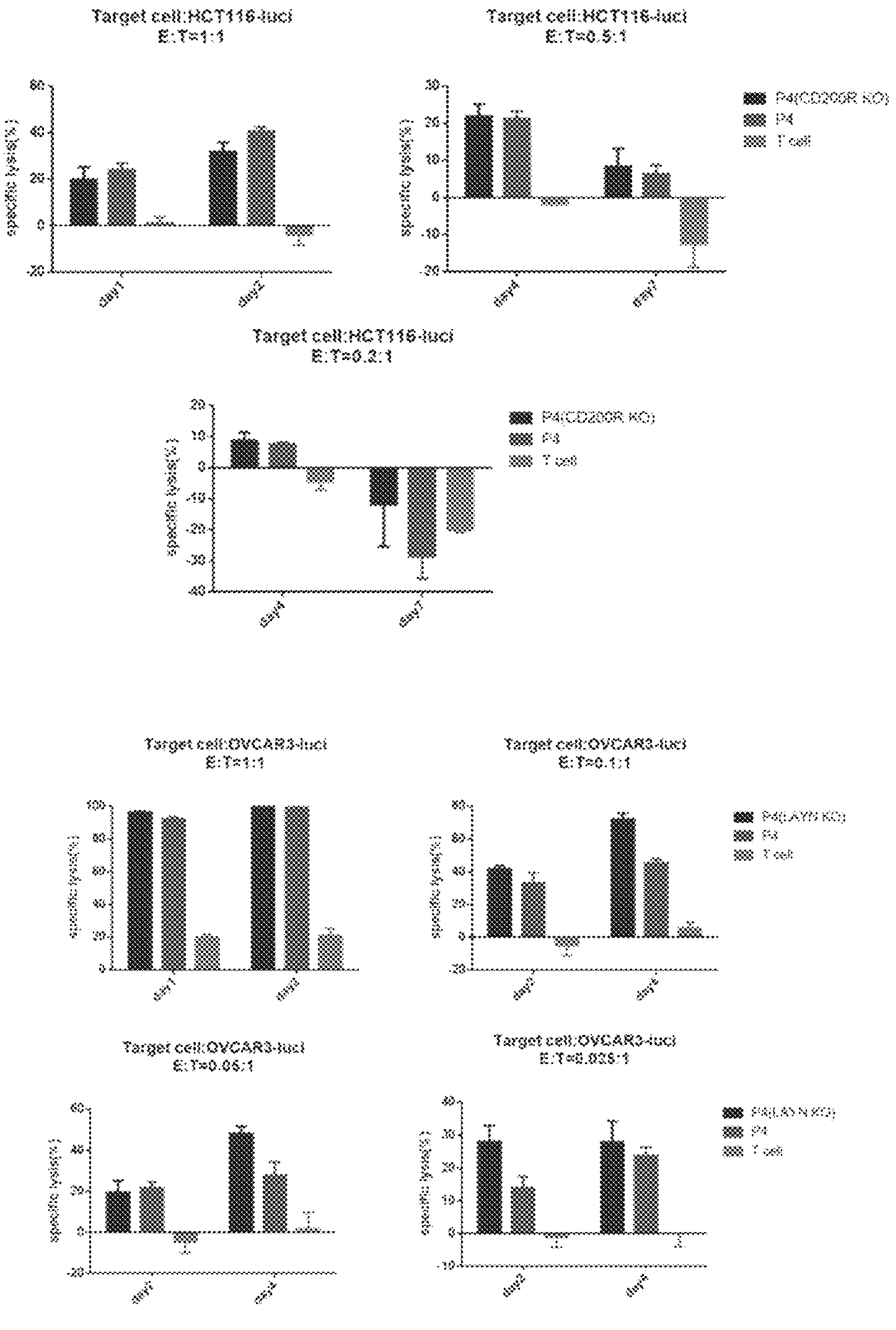
FIG. 24 shows the effects of P4 CAR-T cells knocked out of LAYN gene on target cells HCT116-luci and OVCAR3-luci under different effector: target ratios and treatment times.

At high effector: target ratio (1:1) and in short term (24h, 48h), the LAYN knock-out group showed a killing effect for OVCAR3-luci and HCT116-luci not lower than that of the control CAR-T cells. For long-term and low-efficitor: target ratio killing, it showed a killing stronger than that of the control CAR-T cells. (FIG. 24)

Figure 25:
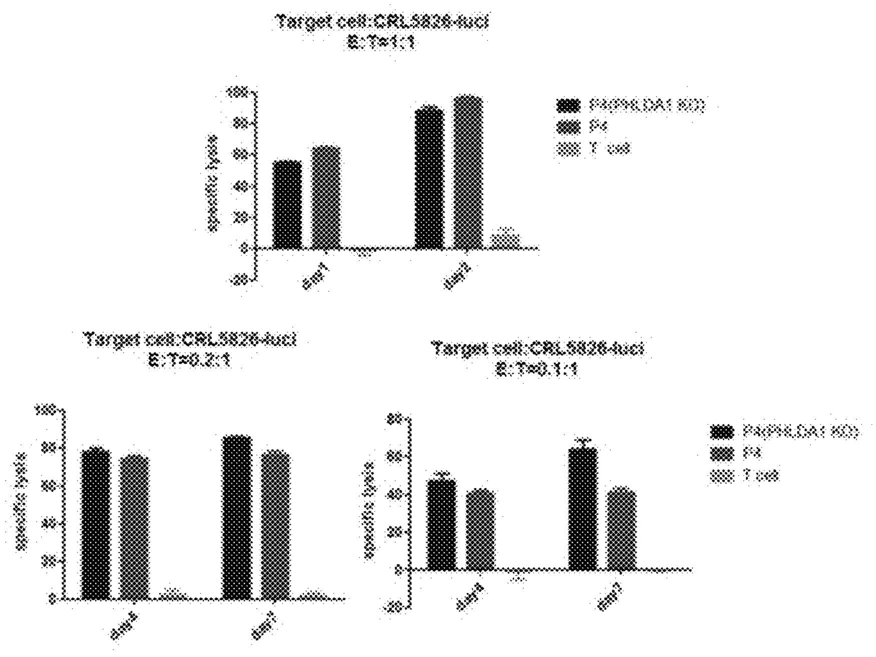
FIG. 25 shows the specific lysis of the target cell CRL5826-luci by P4 CAR-T cells with PHLDA1 gene knocked out under different effector: target ratios and treatment times.

At high effector: target ratio (1:1) and in short term (24h, 48h), the PHLDA1 knock-out group showed a killing effect for CRL5826-luci not lower than that of the control CAR-T cells. At lower effector: target ratio of 0.2:1, the killing of the knock-out group on the fourth and seventh days achived above 70%, not lower than that of the control CAR-T cells. At an effector: target ratio reduced to 0.1:1, the killing of the PHLDA1 knock-out group on the fourth and seventh day was stronger than the control CAR-T cells, especially on the seventh day. (FIG. 25)

Figure 26:
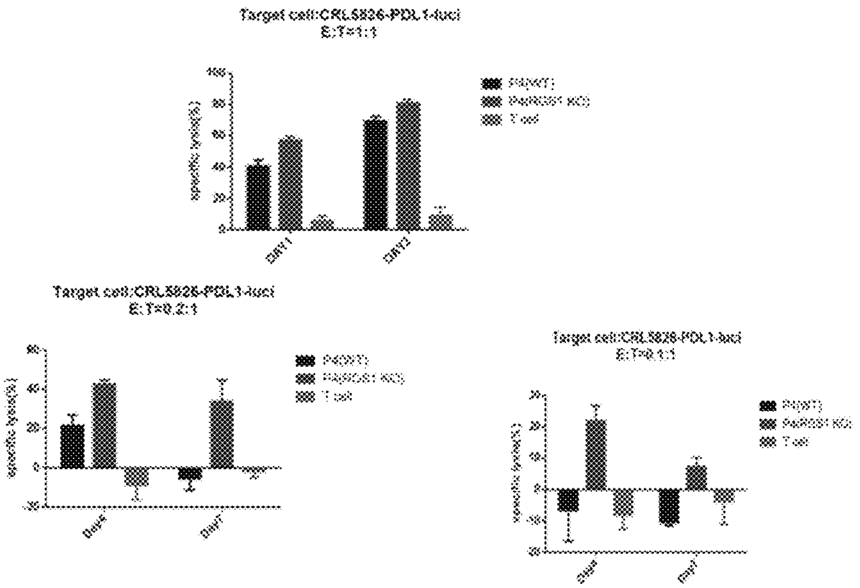
FIG. 26 shows the specific lysis of target cells CRL5826-luci by P4 CAR-T cells with RGS1 gene knocked out under different effector: target ratios and treatment times.

At high effector: target ratio (1:1) and in short term (24h, 48h), the RGS1 knock-out group showed a killing effect for CRL5826-luci not lower than that of the control CAR-T cells. At lower effector: target ratio of 0.2:1, the killing of the knock-out group on the fourth and seventh days achieved above 70%, not lower than that of the control CAR-T cells. At an effector: target ratio reduced to 0.1:1, the killing of the RGS1 knock-out group on the fourth and seventh day was stronger than the control CAR-T cells. (FIG. 26)

Figure 27:
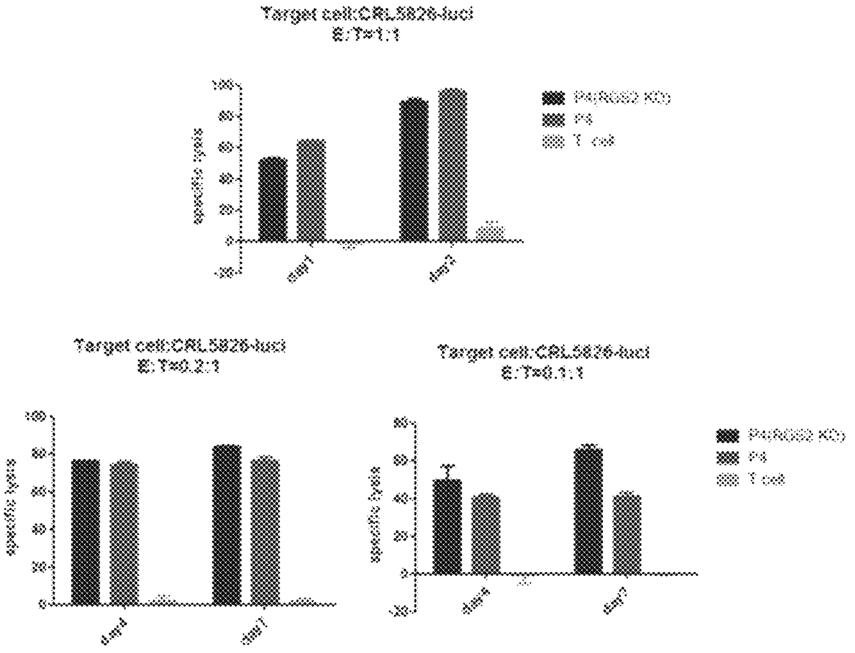
FIG. 27 shows the specific lysis of target cells CRL5826-luci by P4 CAR-T cells with RGS2 gene knocked out under different effector: target ratios and treatment times.

At high effector: target ratio (1:1) and in short term (24h, 48h), the RGS2 knock-out group showed a killing effect for CRL5826-luci not lower than that of the control CAR-T cells. At lower effector: target ratio of 0.2:1, the killing of the knock-out group on the fourth and seventh days achieved above 70%, not lower than that of the control CAR-T cells. At an effector: target ratio reduced to 0.1:1, the killing of the RGS2 knock-out group on the fourth and seventh day was much stronger than the control CAR-T cells. (FIG. 27)

Figure 28:
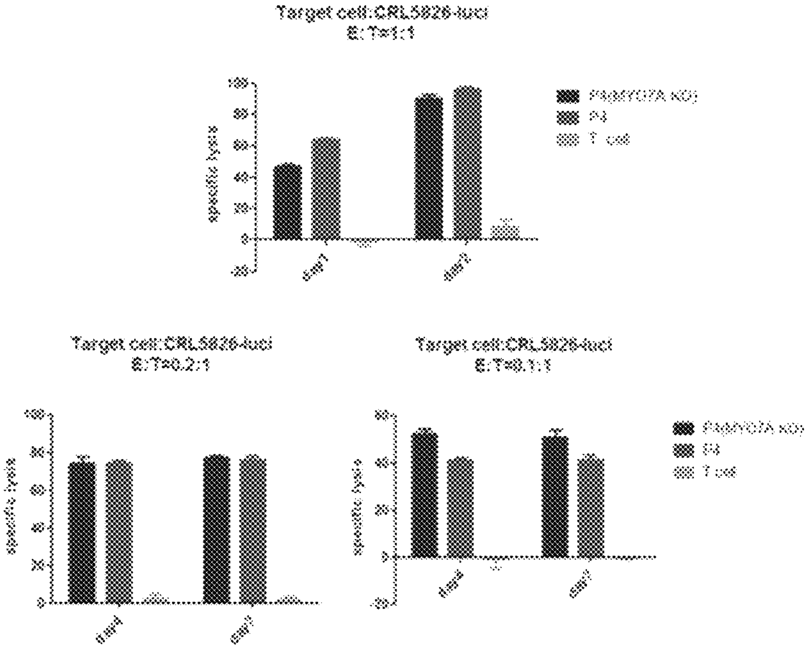
FIG. 28 shows the specific lysis of target cells CRL5826-luci by P4 CAR-T cells with MY07A gene knocked out under different effector: target ratios and treatment times.

At high effector: target ratio (1:1) and in short term (24h, 48h), the MYO7A knock-out group showed a killing effect for CRL5826-luci not lower than that of the control CAR-T cells. At lower effector: target ratio of 0.2:1, the killing of the knock-out group on the fourth and seventh days achieved above 70%, not lower than that of the control CAR-T cells. At an effector: target ratio reduced to 0.1:1, the killing of the MYO7A knock-out group on the fourth and seventh day was slightly stronger than the control CAR-T cells. (FIG. 28)

Example 7. The Effect of Editing Genes Related to the Endogenous Mechanism of T Cell Exhaustion in CAR-T Cells on Tumor Killing In this example, genes related to the endogenous mechanism of T cell exhaustion, such as SHP1, DGKa, Fas, and FasL in CAR-T cells were knocked out through gene editing and their effects on tumor killing were studied.

Figure 29:
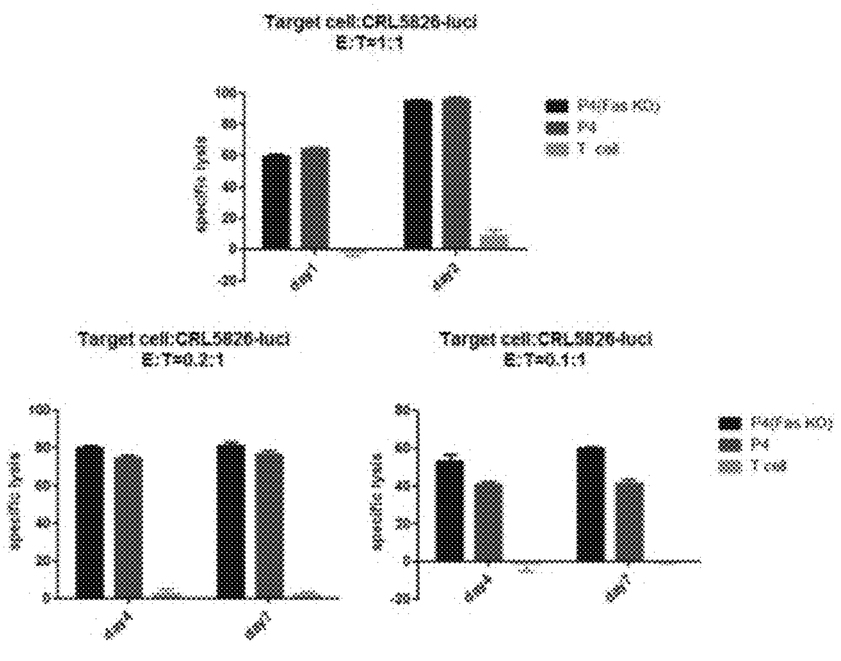
FIG. 29 shows the specific lysis of target cells CRL5826-luci by Fas knocked-out P4 CAR-T cells under different effector: target ratios and treatment times.

At high effector: target ratio (1:1) and in short term (24h, 48h), the Fas knock-out group showed a killing effect for CRL5826-luci not lower than that of the control CAR-T cells. At lower effector: target ratio of 0.2:1, the killing of the knock-out group on the fourth and seventh days achieved above 70%, not lower than that of the control CAR-T cells. At an effector: target ratio reduced to 0.1:1, the killing of the Fas knock-out group on the fourth and seventh day was stronger than the control CAR-T cells. (FIG. 29)

Figure 30:
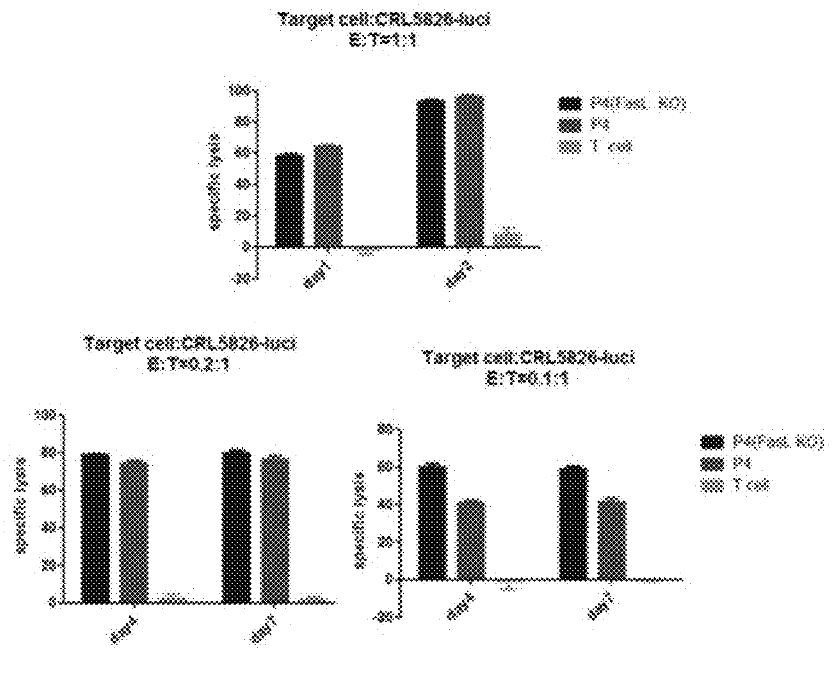
FIG. 30 shows the specific lysis of target cells CRL5826-luci by FasL knocked-out P4 CAR-T cells under different effector: target ratios and treatment times.

At high effector: target ratio (1:1) and in short term (24h, 48h), the FasL knock-out group showed a killing effect for CRL5826-luci not lower than that of the control CAR-T cells. At lower effector: target ratio of 0.2:1, the killing of the knock-out group on the fourth and seventh days achieved above 70%, not lower than that of the control CAR-T cells. At an effector: target ratio reduced to 0.1:1, the killing of the FasL knock-out group on the fourth and seventh day was stronger than the control CAR-T cells. (FIG. 30)

Figure 31:
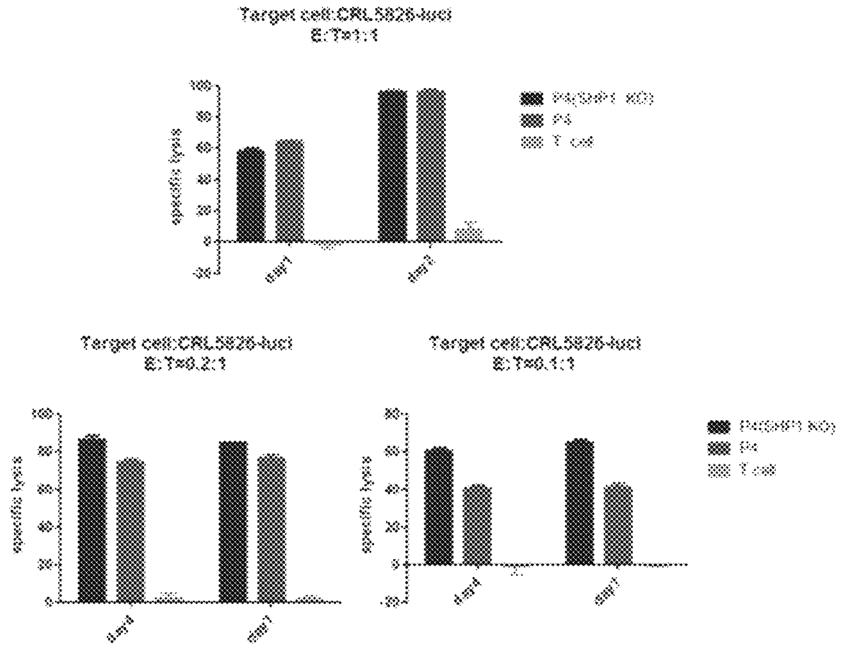
FIG. 31 shows the specific lysis of target cells CRL5826-luci by P4 CAR-T cells with SHP1 gene knocked out under different effector: target ratios and treatment times.

At high effector: target ratio (1:1) and in short term (24h, 48h), the SHP1 knock-out group showed a killing effect for CRL5826-luci not lower than that of the control CAR-T cells. At lower effector: target ratio of 0.2:1, the killing of the knock-out group on the fourth and seventh days achieved above 70%, not lower than that of the control CAR-T cells. At an effector: target ratio reduced to 0.1:1, the killing of the SHP1 knock-out group on the fourth and seventh day was much stronger than the control CAR-T cells. (FIG. 31)

Figure 32:
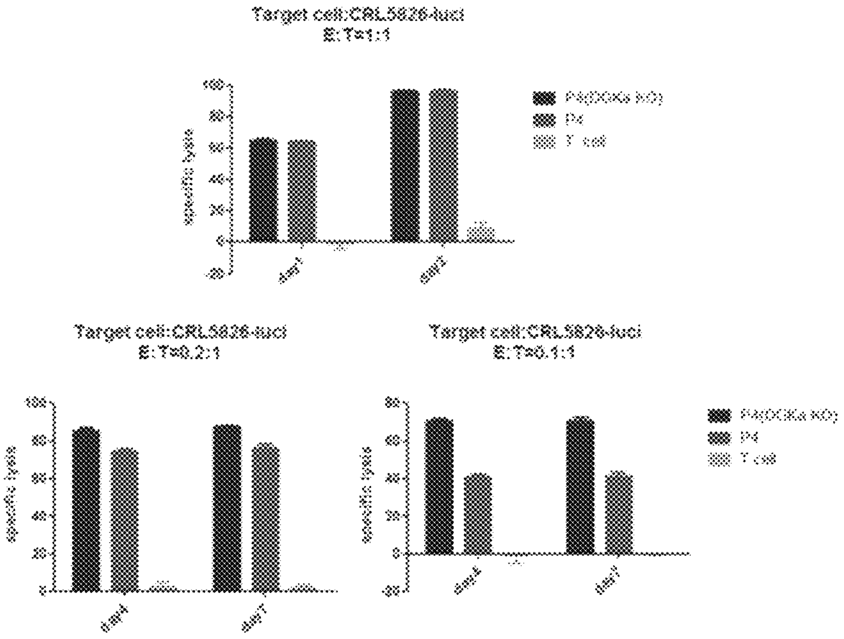
FIG. 32 shows the specific lysis of target cells CRL5826-luci by P4 CAR-T cells with DGKA gene knocked out under different effector: target ratios and treatment times.

At high effector: target ratio (1:1) and in short term (24h, 48h), the DGKa knock-out group showed a killing effect for CRL5826-luci not lower than that of the control CAR-T cells. At lower effector: target ratio of 0.2:1, the killing of the knock-out group on the fourth and seventh days achieved above 70%, not lower than that of the control CAR-T cells. At an effector: target ratio reduced to 0.1:1, the killing of the DGKa knock-out group on the fourth and seventh day was stronger than the control CAR-T cells. (FIG. 32)

Example 8. Improving the Effect of CAR-T Cells in the Treatment of Solid Tumors by Inhibiting the TGFβ Signaling Pathway 1. TGFβ1 negatively regulates the effects of P4-CAR-T cells and can induce P4-CAR-T cells to convert into functional regulatory T cells (Treg).

Figure 33:
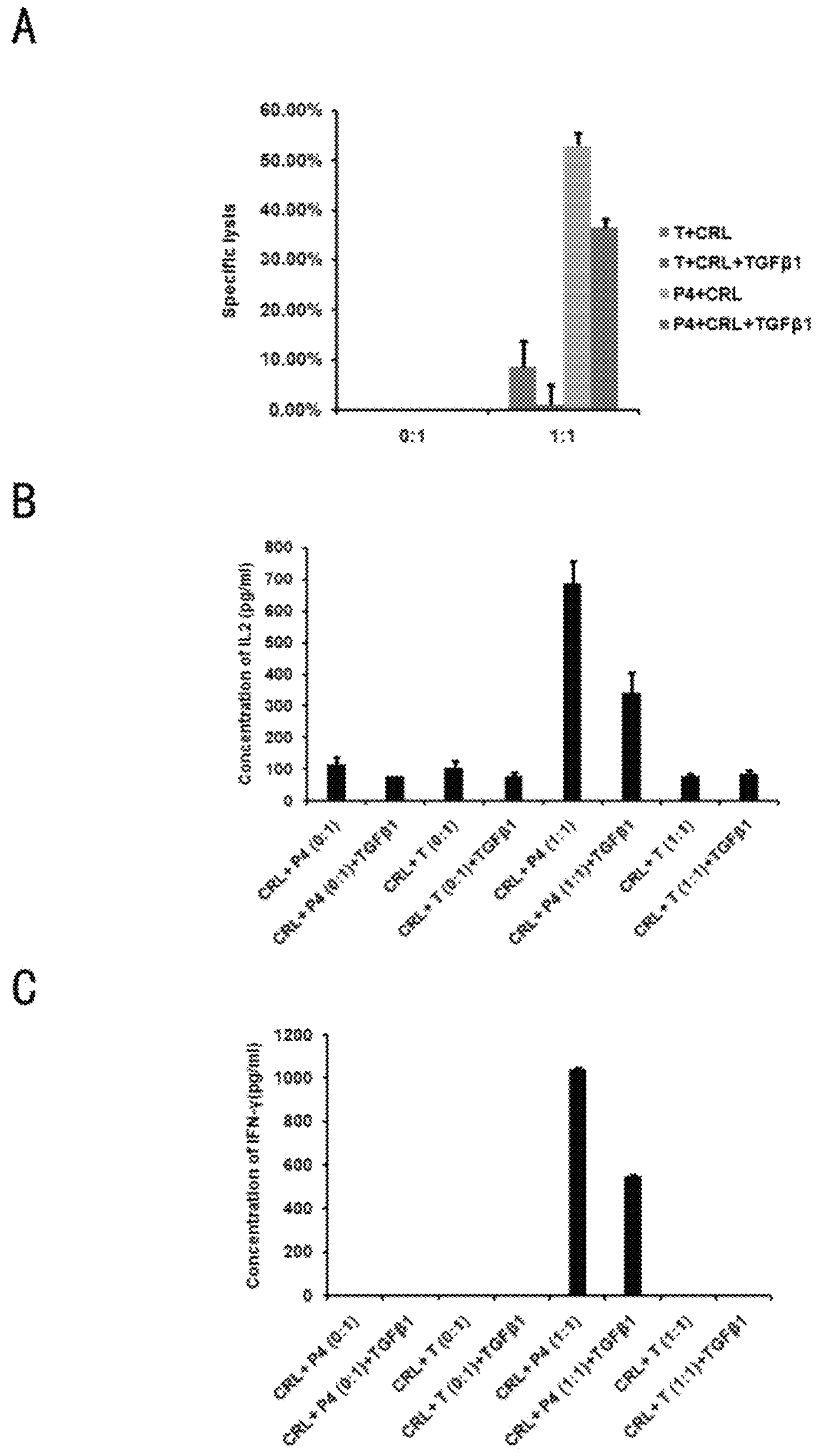
FIG. 33 shows that TGFβ1 negatively affects the function of P4-CAR-T cells. A: CRL5826 tumor cell specific lysis ability of P4-CAR-T cells with or without 5 ng/ml TGFβ1 added to the culture medium. B-C: The concentration of IL-2 (B) and IFN-γ (C) released by P4-CAR-T cells when 5 ng/ml TGFβ1 was added or not added to the culture medium after 24 hours of incubation with CRL5826 cells. T: T cell; P4: P4-CAR-T cell; CRL: CRL5826.

In order to verify whether TGFβ1 affects the killing effect of CAR-T cells, the inventors incubated P4-CAR-T cells targeting mesothelin with CRL5826 mesothelioma cells at a ratio of 1:1 in the culture system with or without addition of 5 ng/ml TGFβ1. The results showed that after 24 hours of co-incubation, the targeted killing ability of P4-CAR-T cells in the TGFβ1 group was significantly lower than that of the non-addition group (FIG. 33A). In order to initially explore the reasons for the decreased killing ability of P4-CAR-T cells in the TGFβ1 group, the release of IL-2 and IFN-γ in the culture medium was detected. It was found that when P4-CAR-T cells were incubated with CRL5826, large amounts of IL-2 and IFN-γ were produced. However, when TGFβ1 was added, the release of IL-2 and IFN-γ decreased by about 50% (FIGS. 33 B and C).

Figure 34:
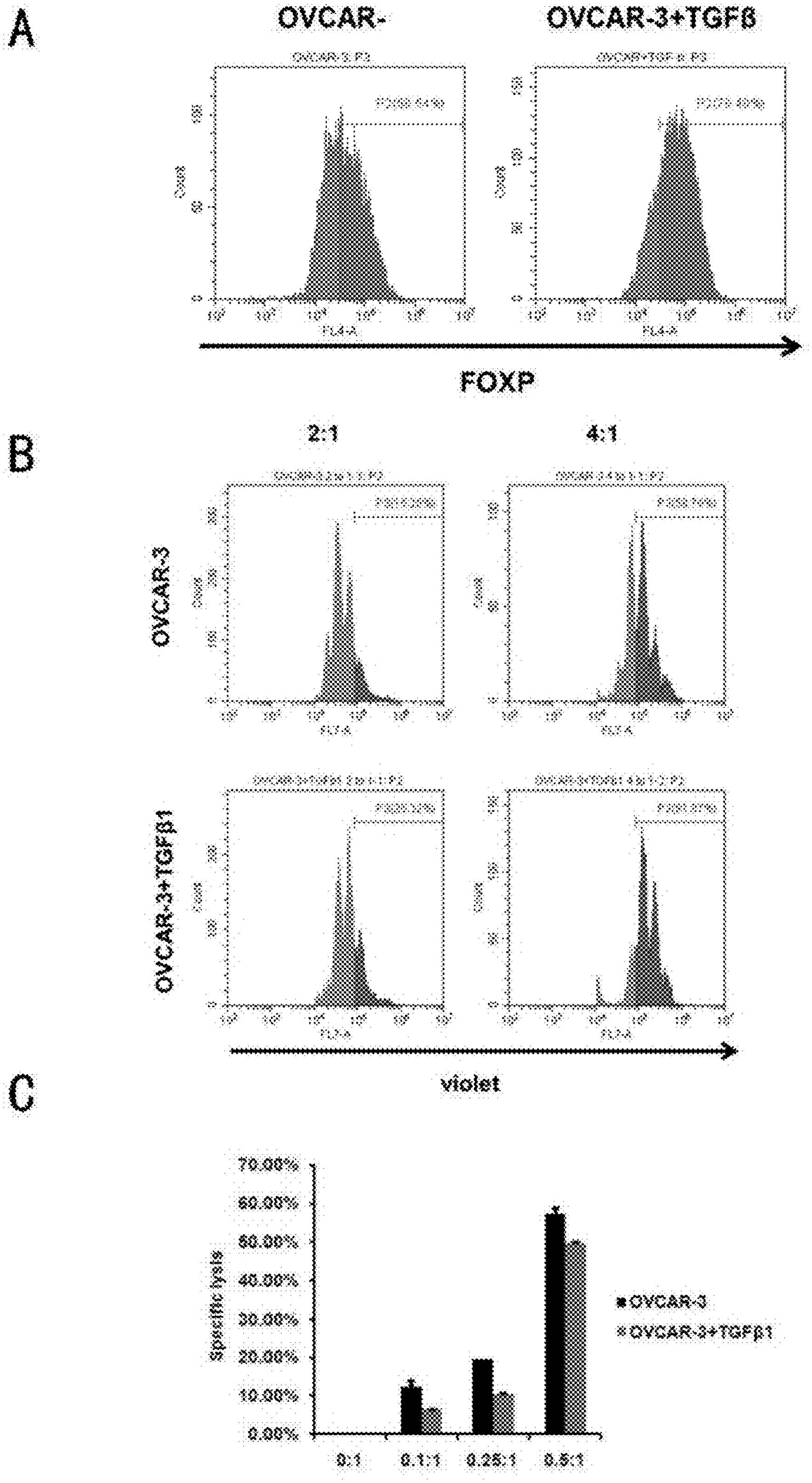
FIG. 34 shows that TGFβ1 can induce the convertion of P4-CAR-T cells into functional Tregs. A: After incubating with OVCAR3 tumor cells for 3 days, with addition or no addition of 5 ng/ml TGFβ1 to the culture medium, the expression of FOXP3 on P4-CAR-T cells. B: The ability of TGFβ1 to inhibit the proliferation of P4-CAR-T cells. P4-CAR-T cells were cultured together with OVCAR3 tumor cells for 3 days, with or without 5 ng/ml TGFβ1 added to the medium. Before the proliferation inhibition assay, GFP-positive P4-CAR-T cells were sorted by FACS. C: The cell lysis ability of P4-CAR-T cells, which were cultured together with OVCAR3 tumor cells for 3 days, with or without 5 ng/ml TGFβ1 added to the culture medium. Before the determination of cell lysis ability, GFP-positive P4-CAR-T cells were sorted by FACS.
Figure 35:
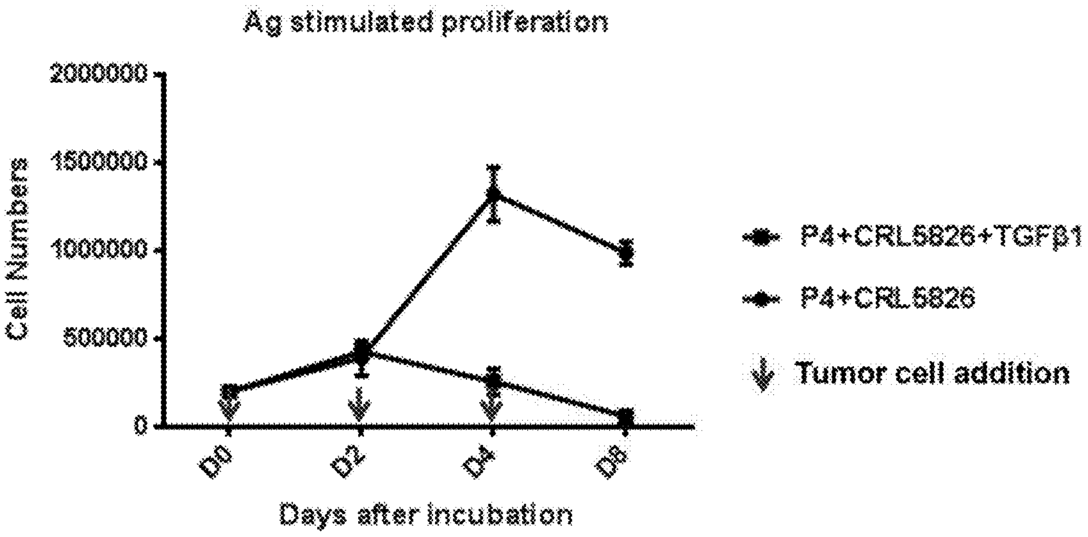
FIG. 35 shows that TGFβ1 affects antigen-induced proliferation ability and cell state of P4-CAR-T cells. A: When 5 ng/ml TGFβ1 wa added or not added to the culture medium, tumor cells induced the proliferation of P4-CAR-T cells. B: A typical image of P4-CAR-T cells 4 days after incubation with CRL5826 after adding or not adding 5 ng/ml TGFβ1 to the medium. P4: P4-CAR-T cells.
Figure 35:
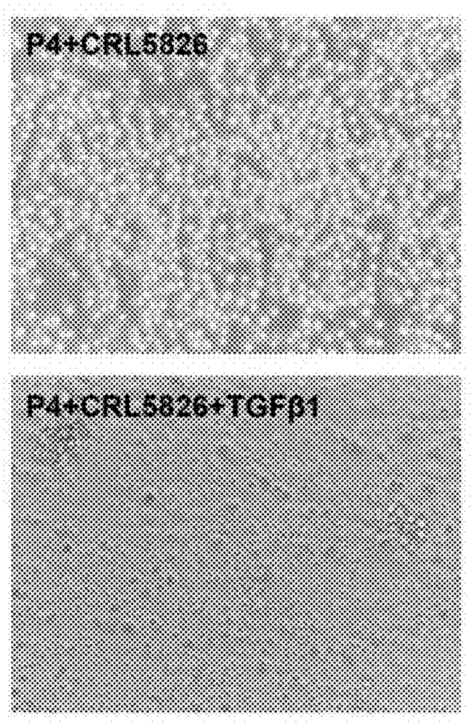

It was reported that, under the conditions of TCR activation and in the presence of TGFβ1, T cells can be converted into inducible Tregs. The inventors added 5 ng/ml TGFβ1 to the co-incubation system of P4-CAR-T and OVCAR-3 cells with strong mesothelin expression to observe whether it can induce the production of Treg. After a total of 3 days of incubation, P4-CAR-T cells were sorted out, and it was found that the expression level of FOXP3 in P4-CAR-T cells was significantly increased in the TGFβ1 group (FIG. 34A). These P4-CAR-T cells were incubated with violet-labeled CD4+CD25-responder cells at a ratio of 2:1 and 1:1, and it was found that P4-CAR-T cells added to the TGFβ1 group could significantly inhibit the proliferation of responder cells (FIG. 34B). This experiment shows that in the presence of TGFβ1, CAR-T cells can be converted into functional Tregs, which have the ability to inhibit proliferation. These P4-CAR-T cells were incubated with OVCAR-3 again, and it was found that the killing ability of P4-CAR-T cells in the TGFβ1 group was significantly lower than that in the non-TGFβ1 group (FIG. 34C). In addition, the effect of TGFβ1 on antigen-induced P4-CAR-T cell proliferation was observed. In the P4-CAR-T cell culture system without IL-2, CRL5826 tumor cells are added every 2 days to induce the proliferation of P4-CAR-T cells, with or without addition of TGFβ1. It can be seen that CRL5826 can induce significant proliferation of P4-CAR-T cells, but in the TGFβ1 group, P4-CAR-T cells basically did not proliferate (FIG. 35A). At the same time, it was observed that in the TGFβ1 group, the state of P4-CAR-T cells was also significantly worse than that in the TGFβ1 group (FIG. 35B).

2. Knockout of TGFBR II or FOXP3 can Improve the Effects of P4-CAR-T Cells

As mentioned above, it has been observed that TGFβ1 can indeed negatively regulate the effects of P4-CAR-T cells. In this experiment, the TGFβ1 binding receptor on P4-CAR-T cells or the important transcription factor FOXP3 produced by Treg was knocked out. The influence on the effects of P4-CAR-T cells in the presence of TGFβ1 was studied. The inventors used CRISPR/Cas9 technology to knock out TGFBR II or FOXP3 of P4-CAR-T cells.

Figure 36:
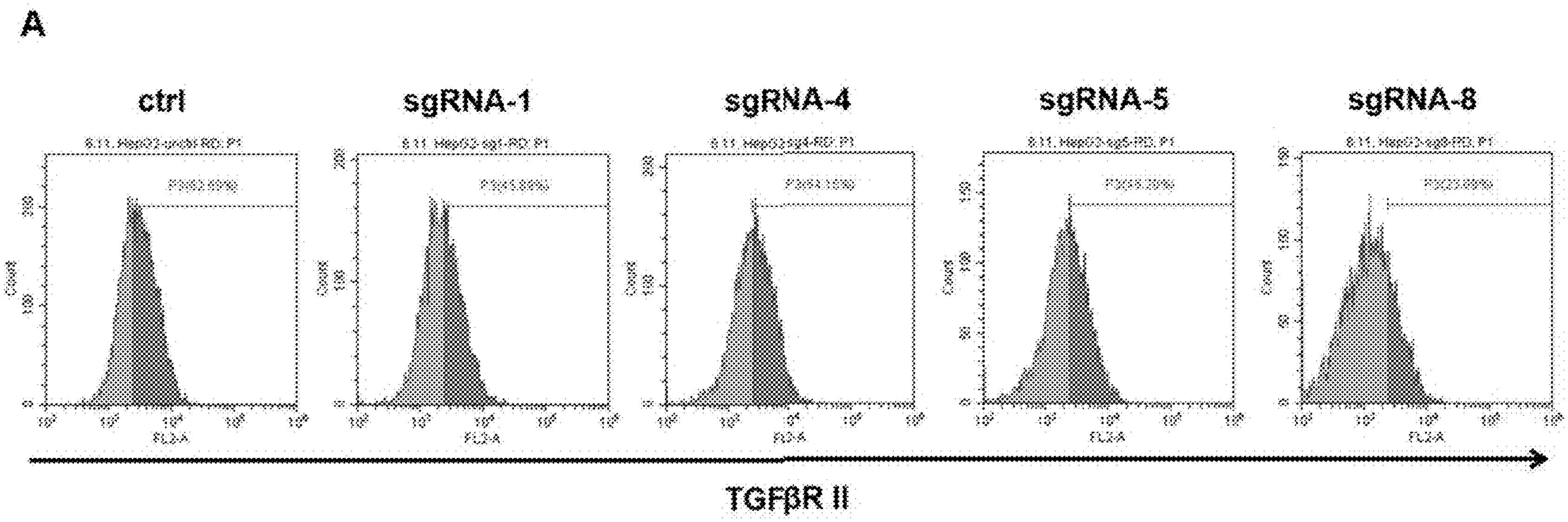
FIG. 36 shows TGFBR II sgRNA selection. A: The efficiency of TGFBR II knockout (KO) on HepG2 electroporated with sgRNA-1 (SEQ ID NO:28), sgRNA-4 (SEQ ID NO:29), sgRNA-5 (SEQ ID NO:30), or sgRNA-8 (SEQ ID NO:31) was detected by flow cytometry (FCM) and TIDE. B: The KO efficiency of TGFBR II on HepG2 electroporated with sgRNA-8 was tested by FCM and TIDE after the conditions were optimized.
Figure 36:
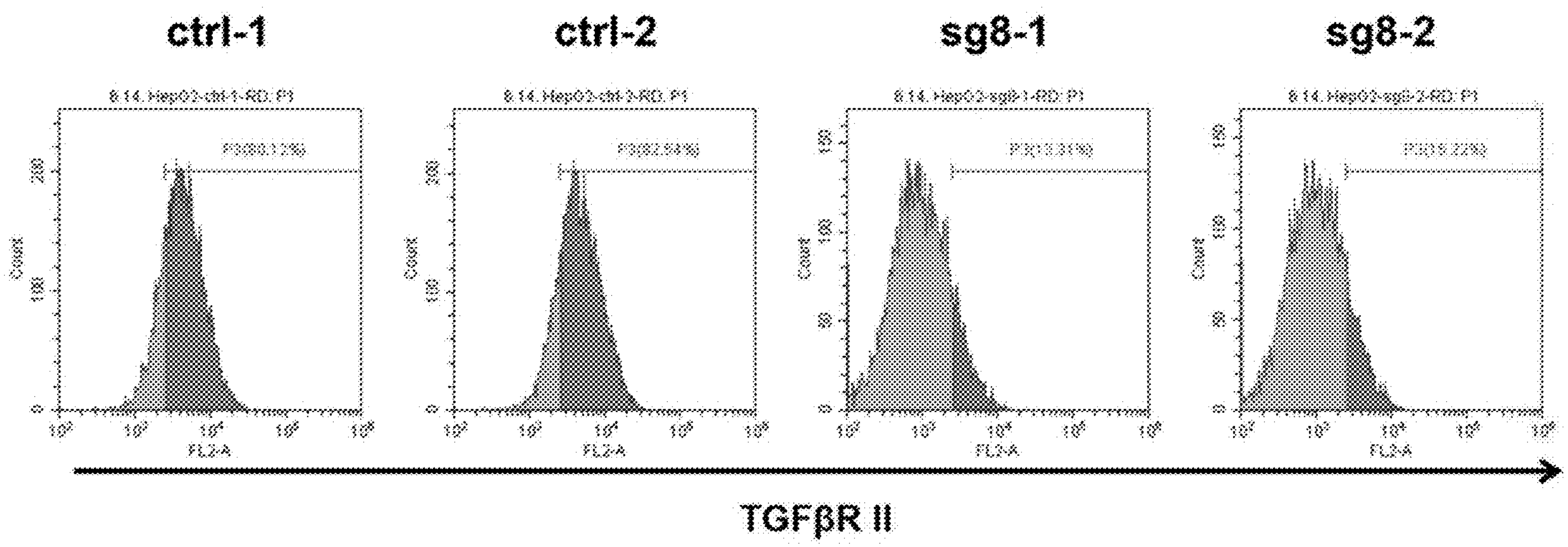

As shown in FIG. 36, sgRNAs against four different target sequences of TGFBR II were tested: sgRNA-1 (target sequence: TGCTGGCGATACGCGTCCAC, SEQ ID NO: 28), sgRNA-4 (target sequence: CCATGGGTCGGGGGCTGCTC, SEQ ID NO: 29), SgRNA-5 (target sequence: CGAGCAGCGGGGTCTGC-CAT, SEQ ID NO: 30), sgRNA-8 (target sequence: CCT-GAGCAGCCCCCGACCCA, SEQ ID NO: 31). These four sgRNAs can all achieve TGFBR II knockout (FIG. 36A). Among them, sgRNA-8 has the highest efficiency. After optimization, the knockout efficiency can reach more than 80%. Similarly FOXP3 was knocked out.

Figure 37:
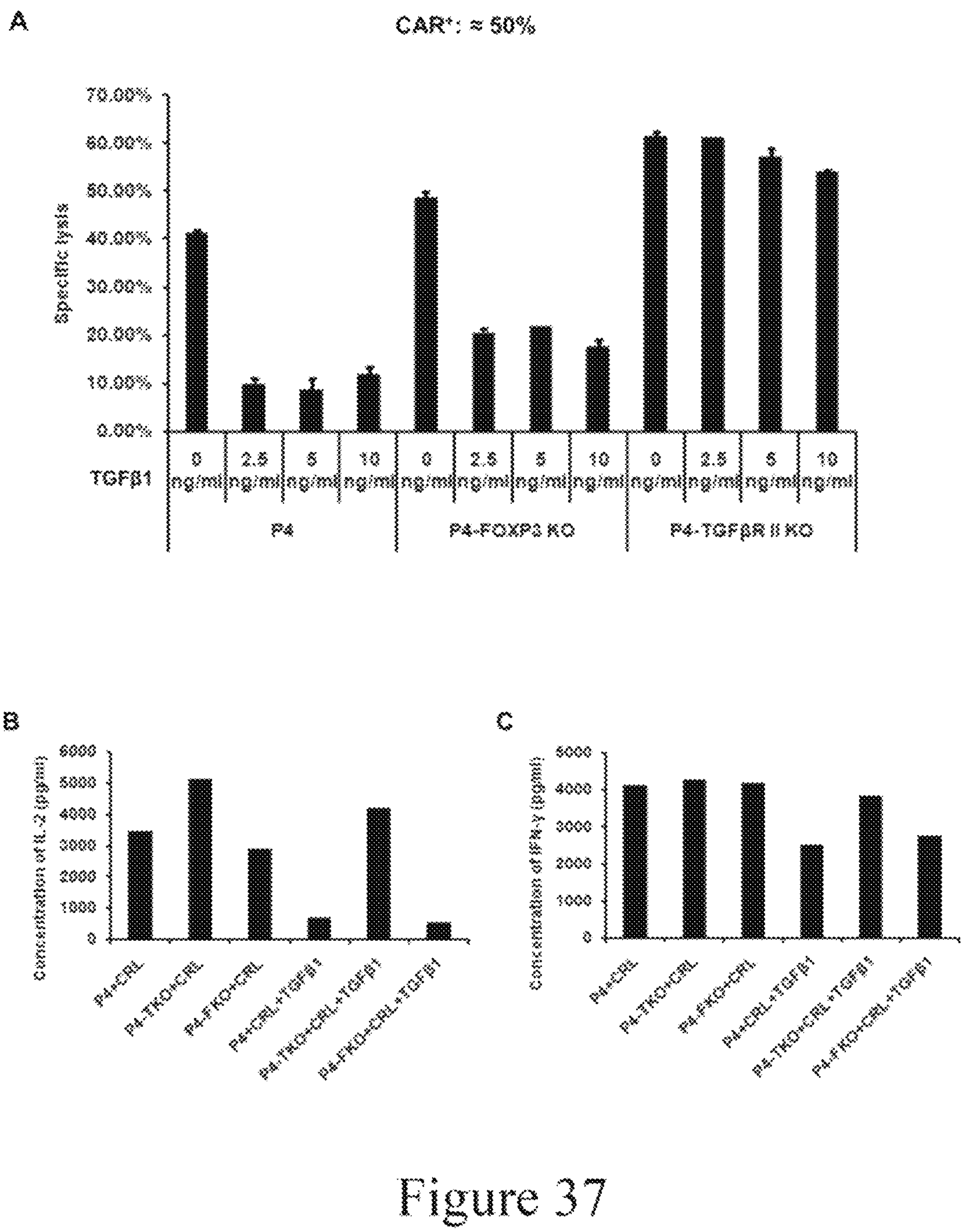
FIG. 37 shows that knocking out TGFBR II or FOXP3 improves the effects of P4-CAR-T cells. A: The tumor cell specific lysis ability of P4-CAR-T cells and TGTBR II/FOXP3 KO P4-CAR-T cells; 0, 2.5, 5 or 10 ng/ml TGFβ1 was added to the culture medium. The effector: target ratio (E: T) is 0.25:1. B-C: After 24 hours of culturing with tumor cells, the concentration of IL-2 (B) and IFN-γ (C) released by P4-CAR-T cells and TGTBR II/FOXP3 KO P4-CAR-T cells, with 5 ng/ml TGFβ1 added or not added into the medium.
Figure 38:
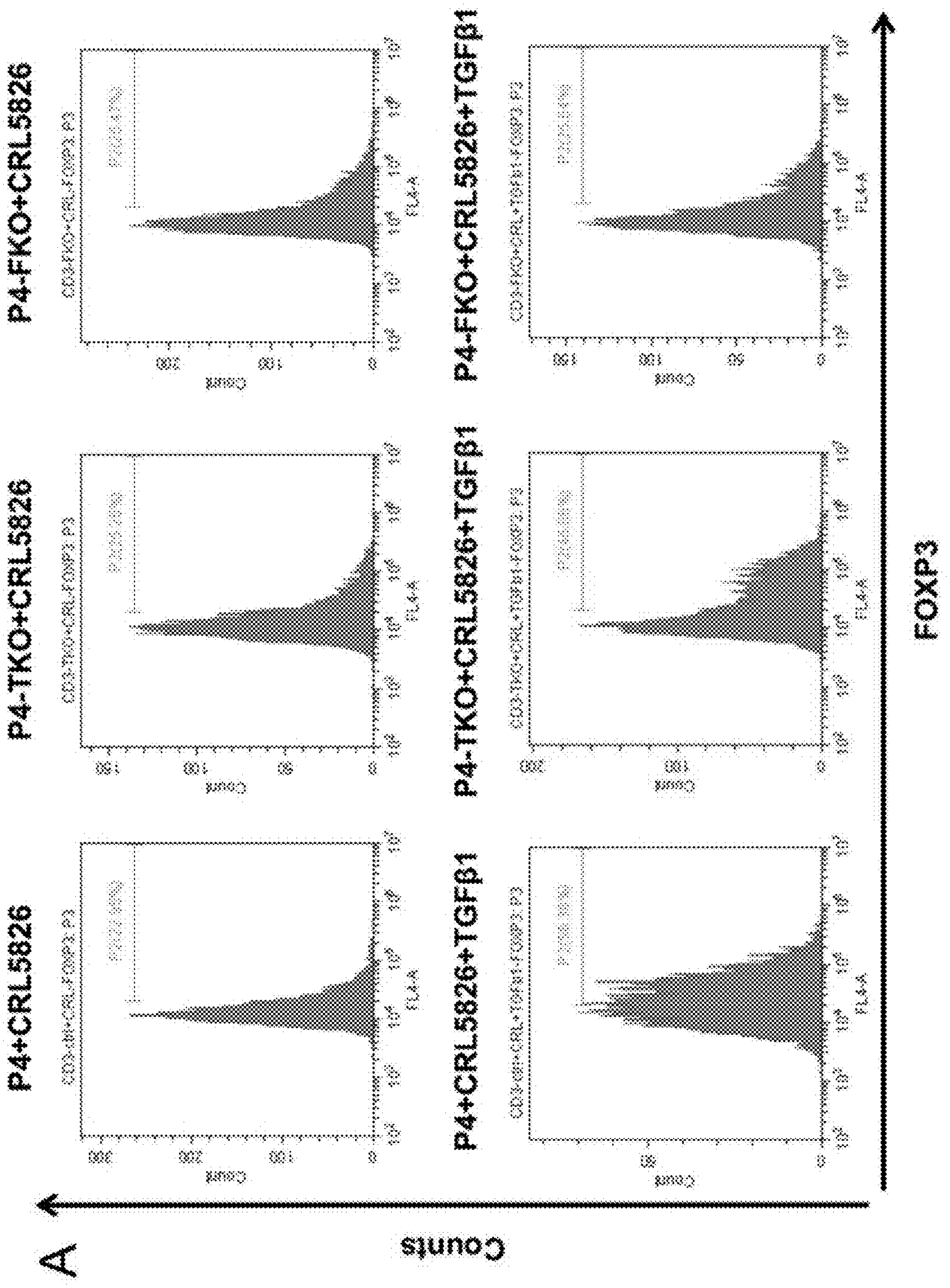
FIG. 38 shows that knocking out TGFBR II or FOXP3 improves the effects of P4-CAR-T cells. A: After incubating with tumor cells for 3 days, adding or not adding 5 ng/ml TGFβ1 to the culture medium, the expression of FOXP3 in P4-CAR-T cells and TGTBR II/FOXP3 KO P4-CAR-T cells. B: The cytolytic ability of P4-CAR-T cells and TGTBR II/FOXP3 KO P4-CAR-T cells, which were cultured together with CRL5826 tumor cells for 3 days, with or without 5 ng/ml TGFβ1 added to the culture medium. GFP-positive P4-CAR-T cells and TGTBR II/FOXP3 KO P4-CAR-T cells were sorted by FACS prior to the cell lysis assay.
Figure 38:
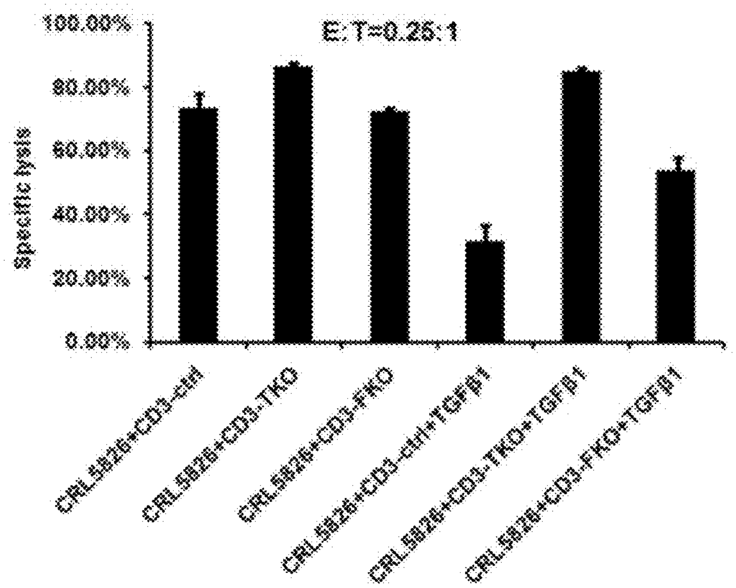
Figure 39:
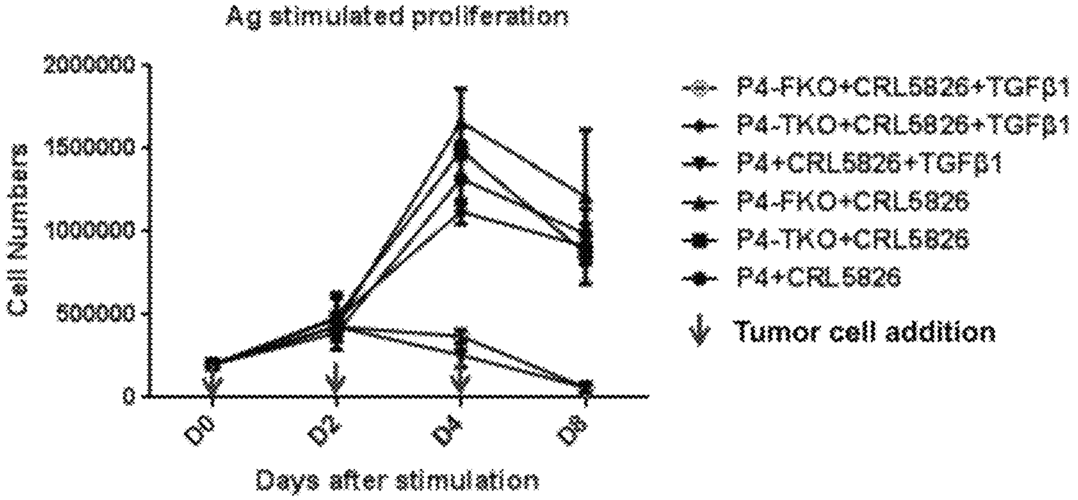
FIG. 39 shows that TGFBR II knockout significantly improved the antigen-induced proliferation ability and cell state of P4-CAR-T cells in the presence of TGFβ1. A: the proliferation of P4-CAR-T cells and TGTBR II/FOXP3 KO P4-CAR-T cells induced by tumor cells when 5 ng/ml TGFβ1 was added or not added to the culture medium. B: Typical images of P4-CAR-T cells and TGTBR II/FOXP3 KO P4-CAR-T cells after incubating with tumor cells with or without 5 ng/ml TGFβ1 in the culture medium for 4 days. FKO: FOXP3 knockout; TKO: TGFBR II knockout.
Figure 39:
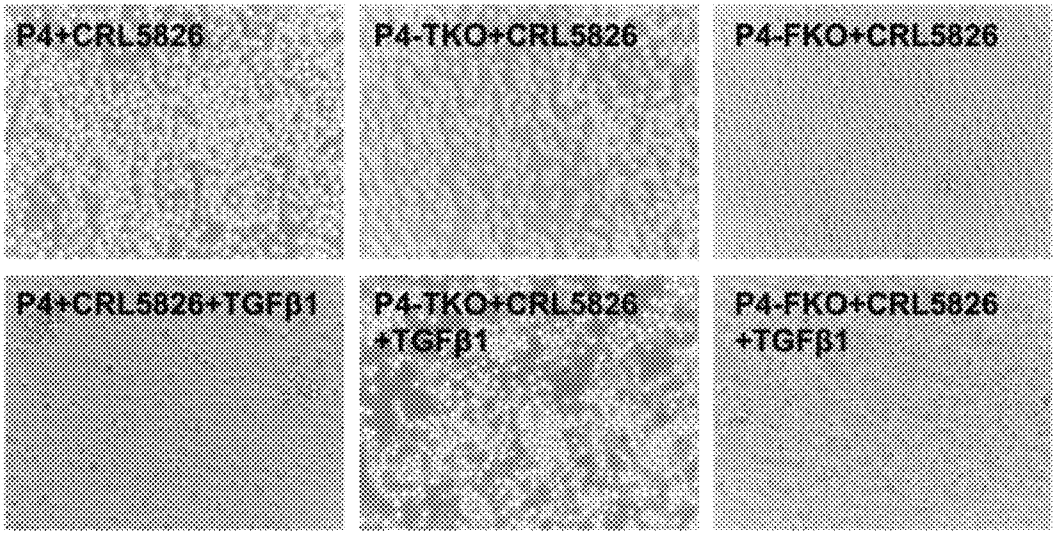
Figure 40:
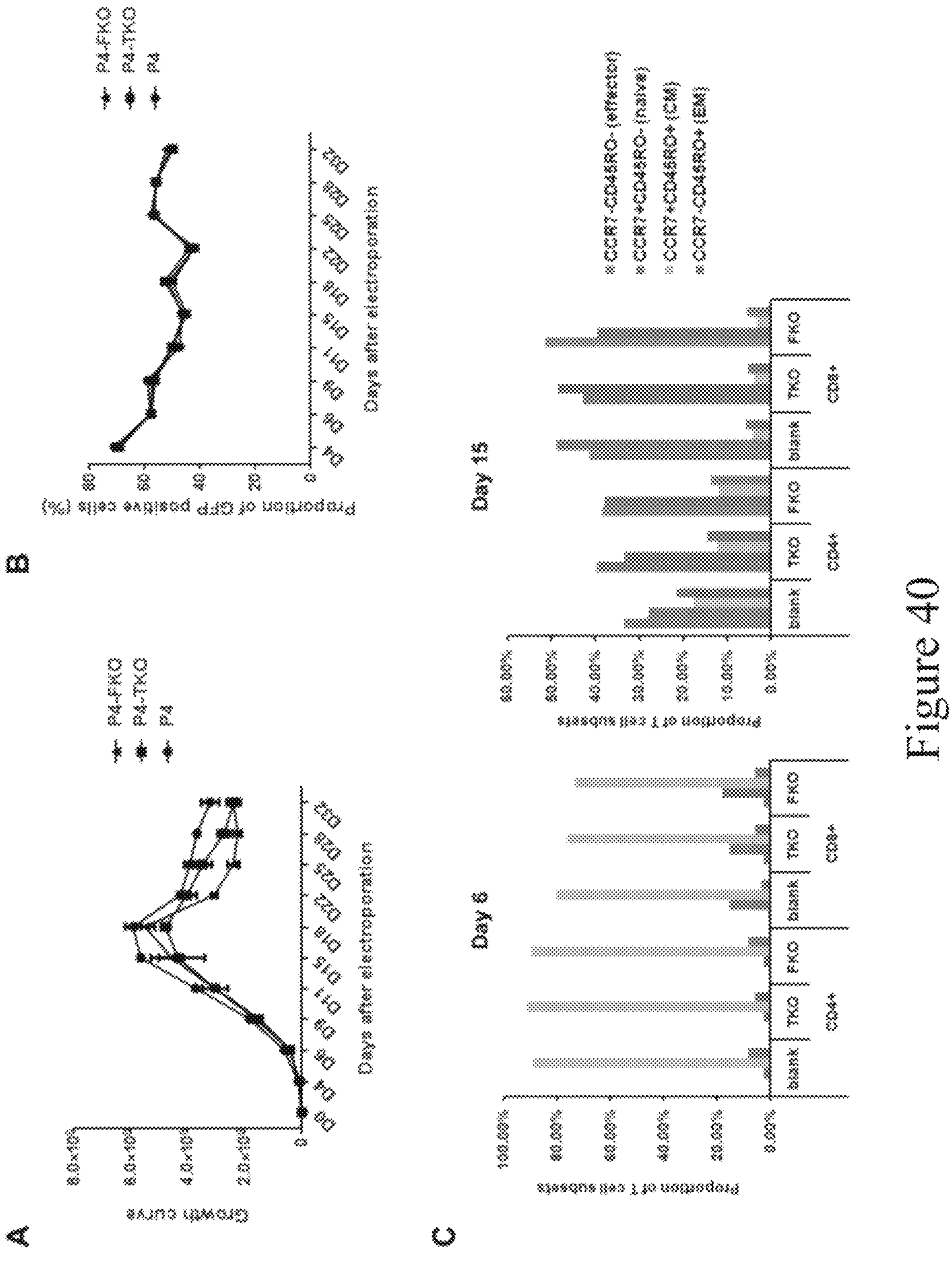
FIG. 40 shows the growth curve of the gene-edited P4 CAR-T cells, the ratio of GFP-positive cells, and the analysis of T cell subpopulations. A: Growth curves of P4 CAR-T cells and TGFBR II KO/FOXP3 KO P4 CAR-T cells after in vitro culture. B: The proportion of GFP-positive cells in P4 CAR-T cells and TGFBR II KO/FOXP3 KO CAR-T cells after in vitro culture. C: Analysis of T cell subsets in CD4+ and CD8+CAR-T cells and TGFBRII KO/FOXP3 KO CAR-T cells at 6 and 15 days after electroporation. P4: P4-CAR-T cells; FKO: FOXP3 knockout; TKO: TGFBR II knockout.

It was found that after knocking out TGFBR II, even if 10 ng/ml TGFβ1 was added, the killing effect of P4-CAR-T cells was not affected in any way, and FOXP3 knockout could also partially improve the killing effect of CAR-T cells (FIG. 37A). Also, it was found that TGFBR II knockout can significantly increase the release of IL-2 and IFN-γ from P4-CAR-T cells in the presence of TGFβ1. However, knockout of FOXP3 did not increase the release of IL-2 and IFN-γ from P4-CAR-T cells (FIGS. 37B and C). In addition, it was found that knockout of TGFBR II or FOXP3 can significantly reduce TCR activation and FOXP3 expression due to TGFβ1 addition in P4-CAR-T cells (FIG. 38A), and can significantly improve the killing ability of P4-CAR-T cells against tumor cells (FIG. 38B). In addition, TGFBR II knockout can significantly improve the proliferation and survival of P4-CAR-T cells induced by antigen in the presence of TGFβ1, however, FOXP3 knockout did not significantly improve the proliferation and survival of P4-CAR-T cells induced by antigen in the presence of TGFβ1 (FIGS. 39A and B). It is worth mentioning that knockout of TGFBR II or FOXP3 did not affect the proliferation ability of P4-CAR-T cells, the expression of CAR, and the distribution of T cell subsets (FIG. 40).

3. Knockout of TGBR II or FOXP3 can Improve the Effects of CD4+CAR-T Cells

Figure 41:
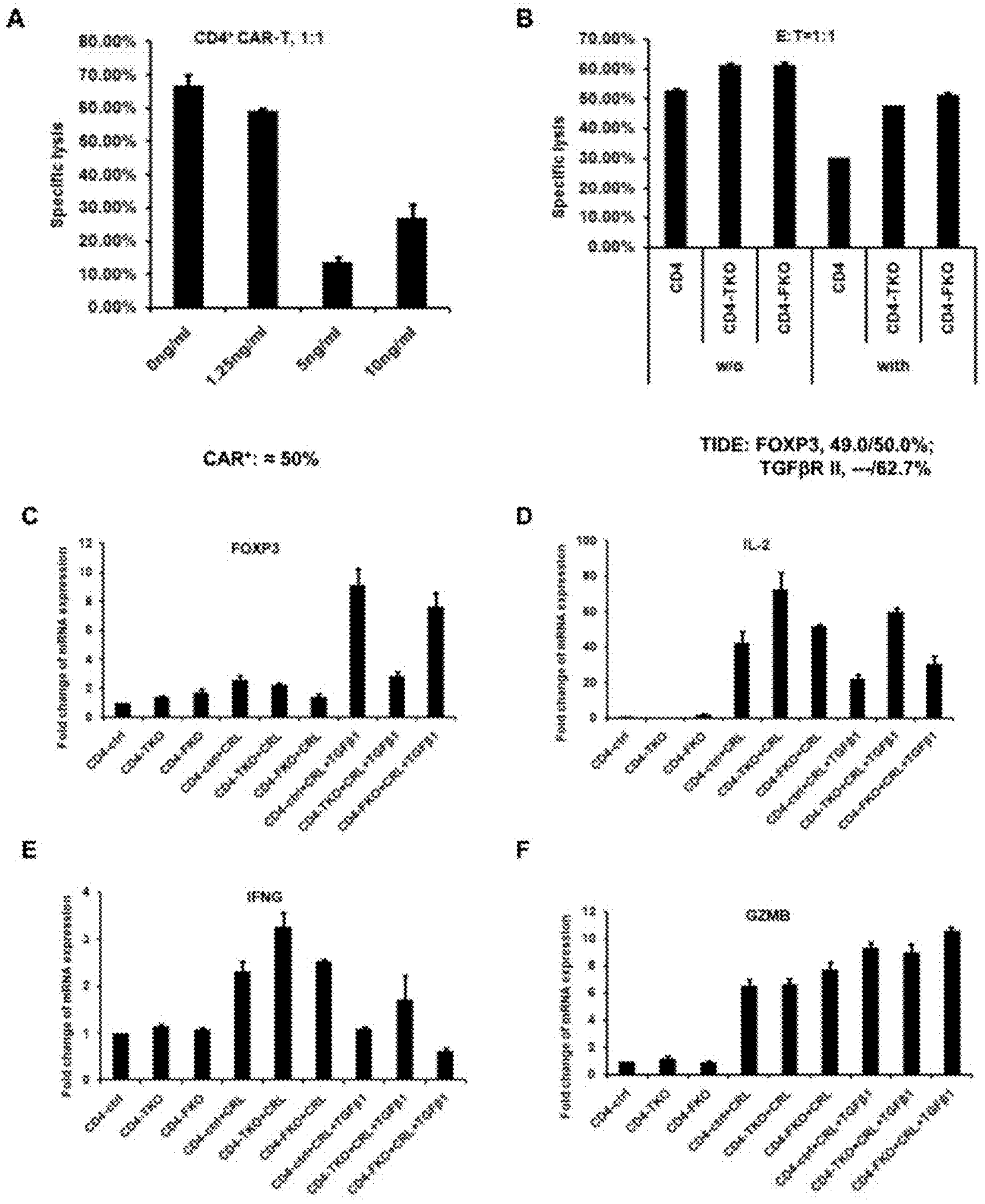
FIG. 41 shows that TGBRII or FOXP3 knockout improves the effects of CD4+CAR-T cells. A: The tumor cell specific lysis ability of CD4+CAR-T cells with 0, 1.25, 5 and 10 ng/ml TGFβ1 added to the culture medium. The effector: target ratio (E: T) is 1:1. B: The tumor cell specific lysis ability of CD4+CAR-T cells and TGFBR II/FOXP3 KO CD4+CAR-T cells, with or without 5 ng/ml TGFβ1 in the medium. The effector: target ratio (E: T) is 1:1. C-F: relative mRNA expression level of FOXP3 (C), IL-2 (D), IFN-γ (E) and GZMB (F) of CD4+CAR-T cells and TGFBR II/FOXP3 KO CD4+CAR-T cells, after 3 days of incubation with tumor cells, with or without 5 ng/ml TGFβ1 in the medium. GFP positive CAR-T cells were sorted by FACS prior to mRNA extraction. ctrl: control; FKO: FOXP3 KO; TKO: TGFBR II KO; CRL: CRL5826; w/o: no addition.
Figure 42:
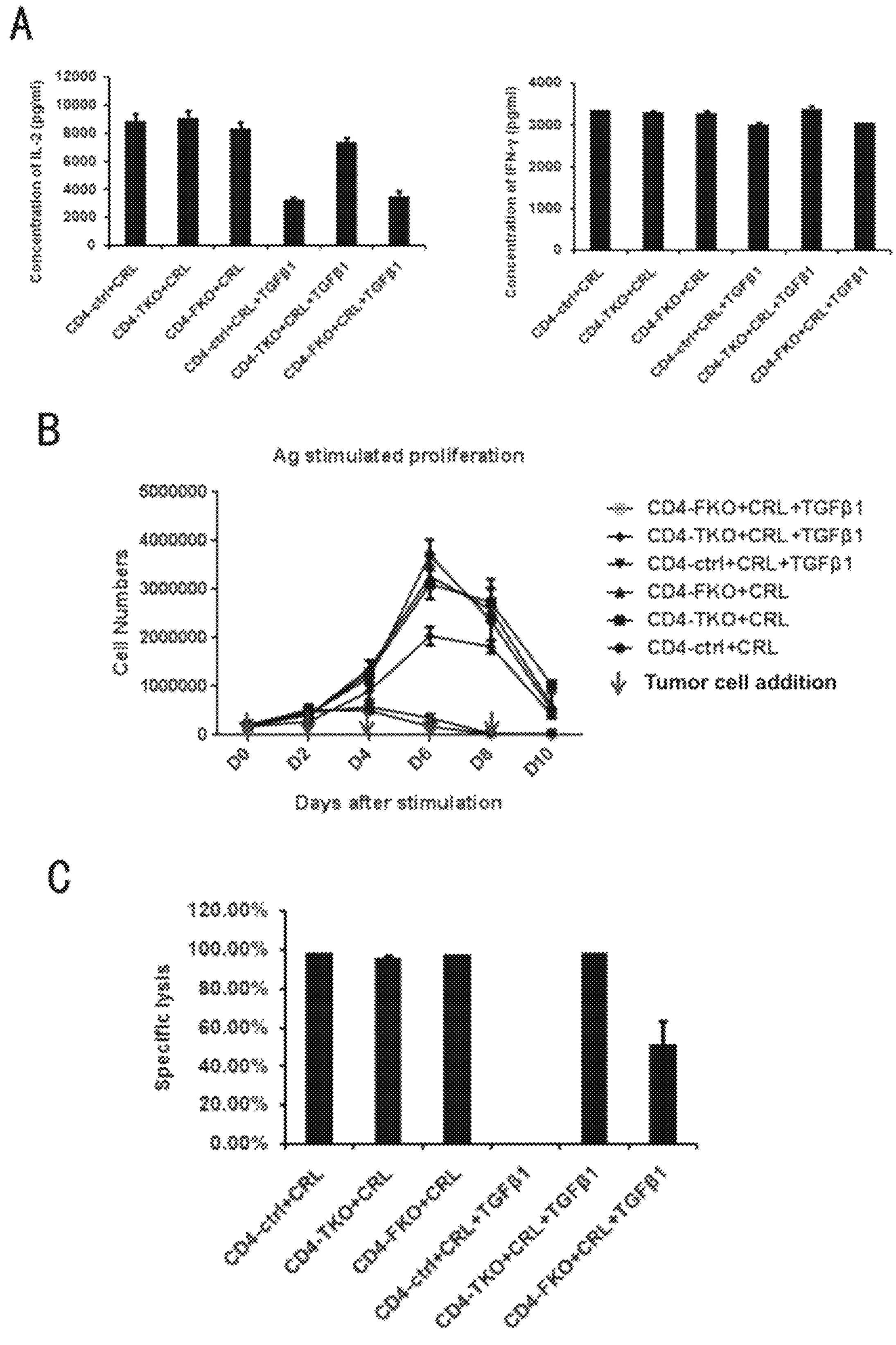
FIG. 42 shows that TGBR II or FOXP3 knockout improves the effects of CD4+CAR-T cells. A: The concentration of IL-2 (left) and IFN-γ (right) released by CD4+ CAR-T cells and TGTBR II/FOXP3 KO CD4+CAR-T cells after 48 hours of incubation with tumor cells, with or without addition of 5 ng/ml TGFβ1 to the medium. B: the proliferation of CD4+CAR-T cells and TGTBR II/FOXP3 KO CD4+CAR-T cells induced by tumor cells, with or without 5 ng/ml TGFβ1 in the medium. C: On the 8th day of incubation with tumor cells, the specific lysis ability of CD4+CAR-T cells and TGTBR II/FOXP3 KO CD4+ CAR-T cells, with or without 5 ng/ml TGFβ1 in the medium. ctrl: control; FKO: FOXP3 KO; TKO: TGFBR II KO; CRL: CRL5826.

This experiment investigated the effects of TGFβ1 on the CD4 and CD8 subgroups in P4-CAR-T cells. In the co-incubation system of CD4+CAR-T cells and CRL5826, different concentrations of TGFβ1 were added. It was found that when 5 or 10 ng/ml TGFβ1 was added, the targeted killing ability of P4-CAR-T cells could be significantly inhibited (FIG. 41A), while the knockout of TGFBR II or FOXP3 could significantly improve the killing ability of CD4+CAR-T cells (FIG. 41B). Also, it was found that TGFβ1 can regulate the expression of many genes at transcription level in CD4+CAR-T cells, such as up-regulating FOXP3 and down-regulating IL-2 and IFN-γ. After knocking out TGBR II, FOXP3 was reduced and IL-2 and IFN-γ were up-regulated (FIG. 41C-E). However, the expression of GZMB was not significantly affected by TGFβ1 (FIG. 41F). Similar changes in the expression of IL-2 and IFN-γ were also observed at the protein level (FIG. 42A). In addition, it was also observed that TGFβ1 can significantly inhibit the proliferation ability of CD4+CAR-T cells induced by antigen. TGFBR II knockout can significantly improve this phenomenon, but the effect of FOXP3 knockout is not obvious (FIG. 42B). Also, the killing ability of CD4+CAR-T cells with TGBR II or FOXP3 knocked out after multiple rounds of antigen stimulation was significantly better than that of unedited CD4+CAR-T cells (FIG. 42C).

4. Knockout of TGBR II or FOXP3 can Improve the Effects of CD8+CAR-T Cells

Figure 43:
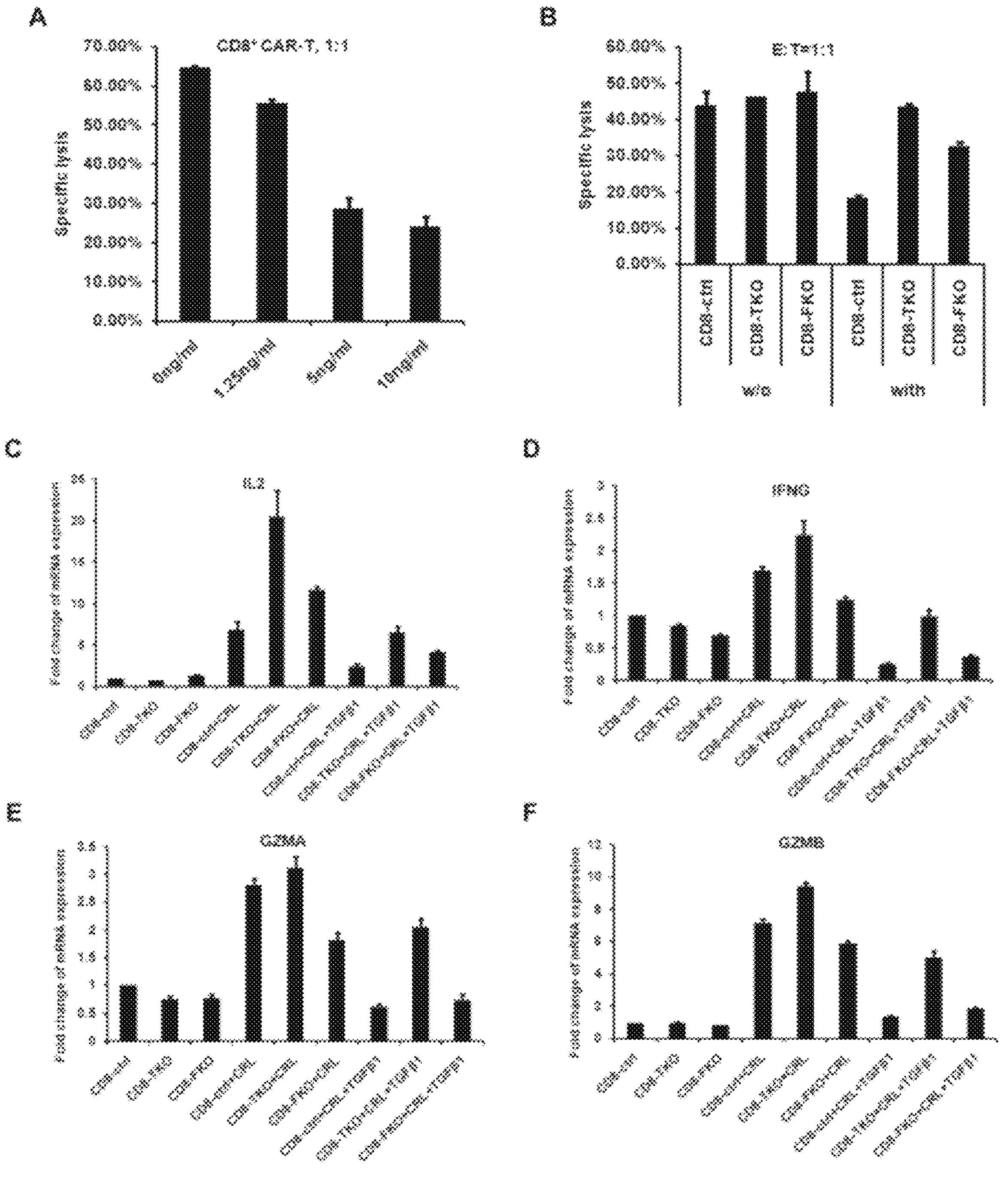
FIG. 43 shows that TGBR II or FOXP3 knockout improves the effects of CD8+CAR-T cells. A: The tumor cell specific lysis ability of CD8+CAR-T cells with 0, 1.25, 5 and 10 ng/ml TGFβ1 added to the culture medium. The effector: target ratio (E: T) is 1:1. B: The tumor cell specific lysis ability of CD8+CAR-T cells and TGFBR II/FOXP3 KO CD8+CAR-T cells, with or without 5 ng/ml TGFβ1 in the medium. The effector: target ratio (E: T) is 1:1. C-F: the relative mRNA expression level of IL-2 (C), IFN-γ (D), GZMA (E) and GZMB (F) of CD8+CAR-T cells and TGFBR II/FOXP3 KO CD8+CAR-T cells after 3 days of incubation with tumor cells, with or without 5 ng/ml TGFβ1 added to the medium. GFP positive CAR-T cells were sorted by FACS prior to mRNA extraction. ctrl: control; FKO: FOXP3 KO; TKO: TGFBR II KO; CRL: CRL5826; w/o: no addition.
Figure 44:
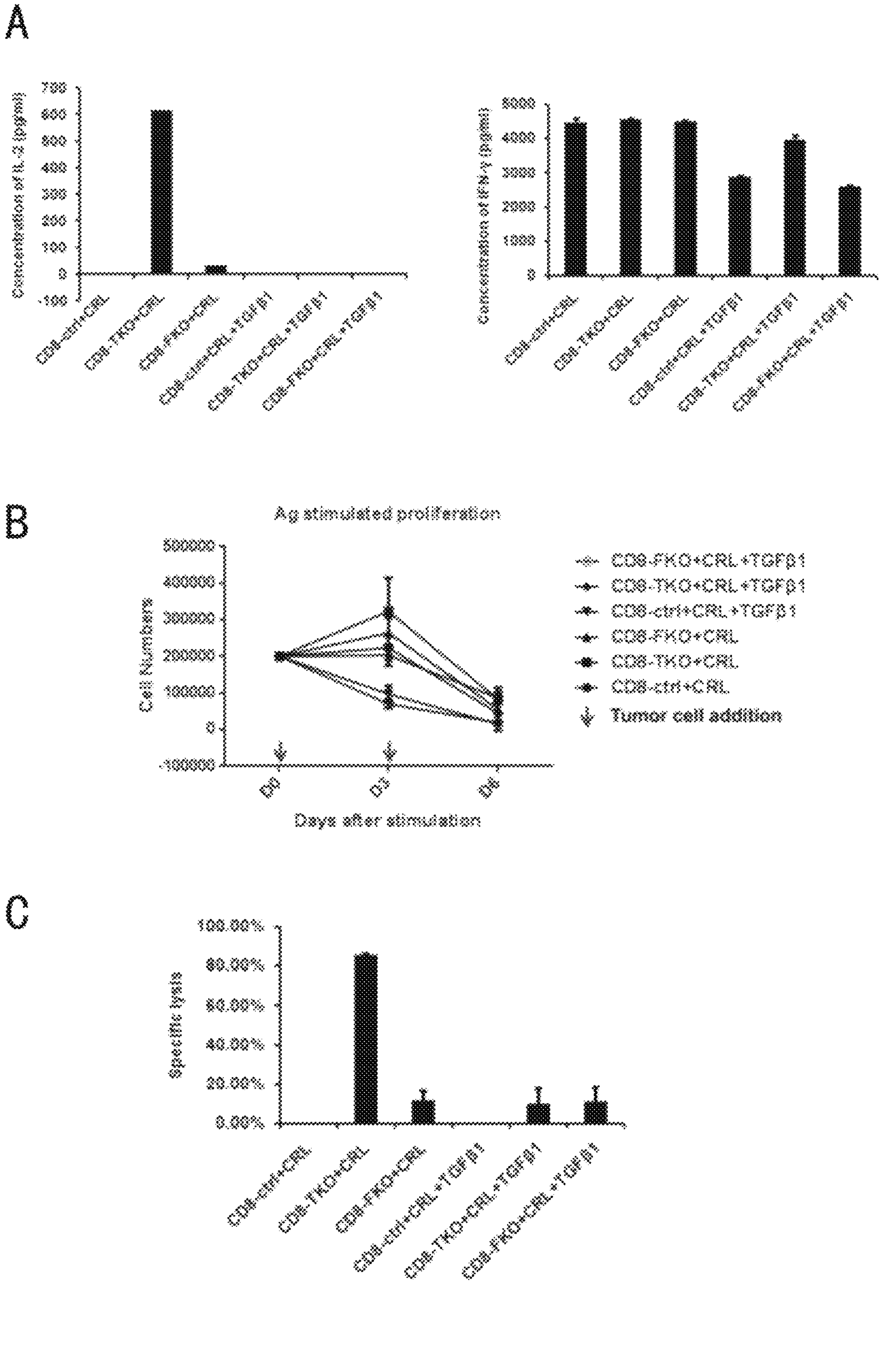
FIG. 44 shows that TGBR II or FOXP3 knockout improves the effects of CD8+CAR-T cells. A: The concentration of IL-2 (left) and IFN-γ (right) released by CD8+ CAR-T cells and TGTBR II/FOXP3 KO CD8+CAR-T cells after 48 hours of incubation with tumor cells, with or without 5 ng/ml TGFβ1. B: the proliferation of CD8+ CAR-T cells and TGTBR II/FOXP3 KO CD8+CAR-T cells induced by tumor cells, with or without 5 ng/ml TGFβ1 in the medium. C: On the 8th day of incubation with tumor cells, the specific lysis ability of CD8+CAR-T cells and TGTBR II/FOXP3 KO CD8+CAR-T cells, with or without 5 ng/ml TGFβ1 in the medium. ctrl: control; FKO: FOXP3 KO; TKO: TGFBR II KO; CRL: CRL5826.

In the co-incubation system of CD8+CAR-T cells and CRL5826, different concentrations of TGFβ1 were added. It was found that as the added concentration increased, the tumor-killing ability of CD8+CAR-T cells was inhibited more obviously (FIG. 43A), while TGFBR II or FOXP3 knockout can significantly improve the killing ability of CD8+CAR-T cells (FIG. 43B). Also, it was found that TGFβ1 can regulate the expression of many genes at transcription level in CD8+CAR-T cells, such as down-regulating IL-2, IFN-γ, GZMA and GZMB. After knocking out TGBR II, the expression of these genes can be up-regulated (FIG. 43C-F). We also observed similar changes in the expression of IFN-γ at the protein level (FIG. 44A). However, except for the obvious IL-2 expression in CD8+CAR-T cells with TGBR II knocked out, all other groups showed no obvious expression (FIG. 44A). In addition, it was also observed that TGFβ1 can significantly inhibit the proliferation ability of CD8+CAR-T cells induced by antigen. TGFBR II knockout can significantly improve this phenomenon, but the effect of FOXP3 knockout is not obvious (FIG. 44B). Also, the killing ability of CD8+CAR-T cells with TGBR II or FOXP3 knocked out after multiple rounds of antigen stimulation was significantly better than that of unedited CD8+CAR-T cells (FIG. 44C). However, it is worth mentioning that the antigen-stimulating proliferation ability and multi-round killing ability of CD8+CAR-T cells are significantly weaker than that of CD4+CAR-T cells.

Example 9. TGFBR II/PD1 Double-Edited CAR-T Cells have an Improved Therapeutic Effect on Solid Tumors 9.1 TGFβ1 Accelerates CAR-T Cell Depletion by Up-Regulating PD1

Figure 46:
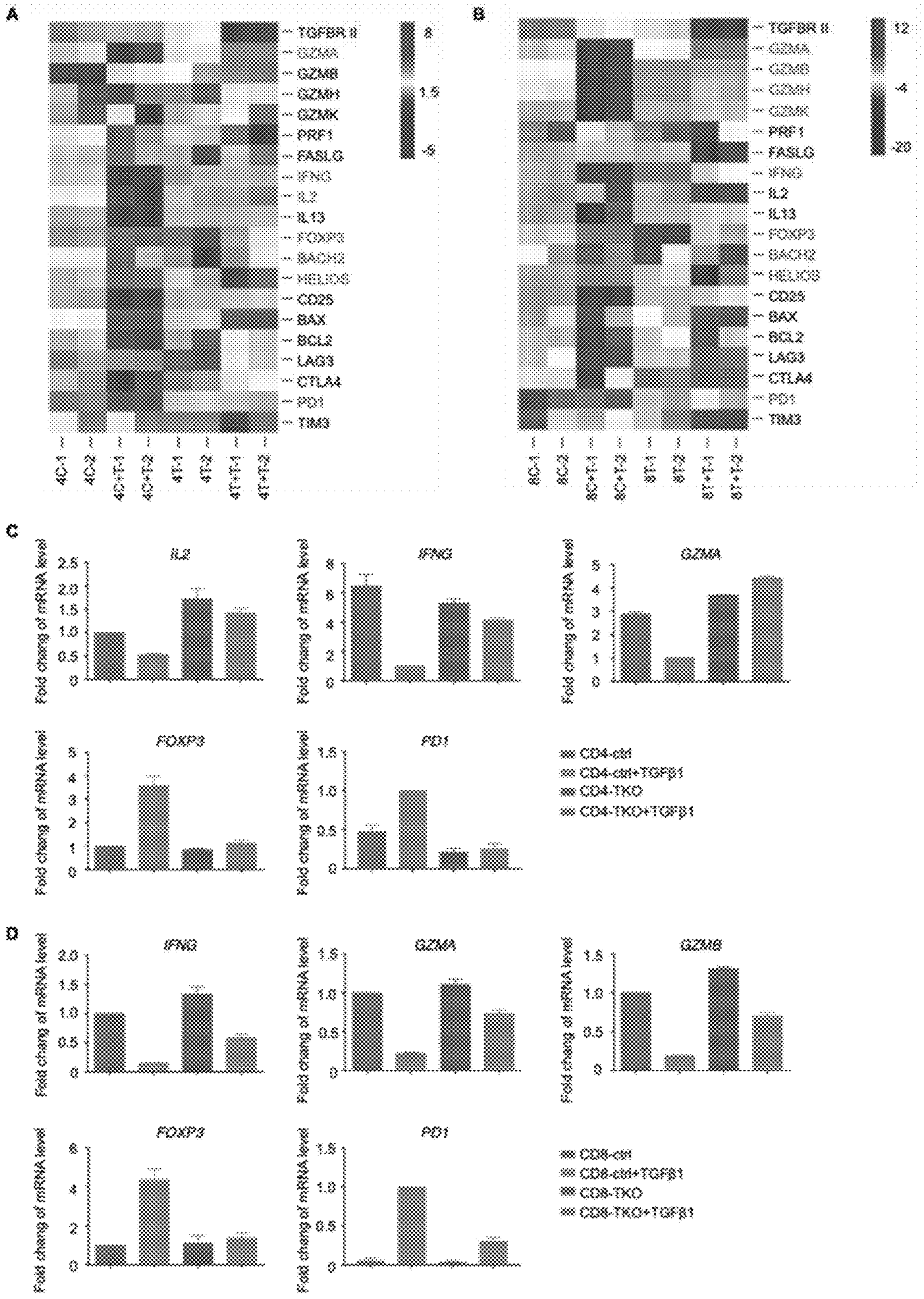
FIG. 46 shows that the expression of PD1 mRNA in M28z increased significantly after the addition of TGFβ1.
Figure 47:
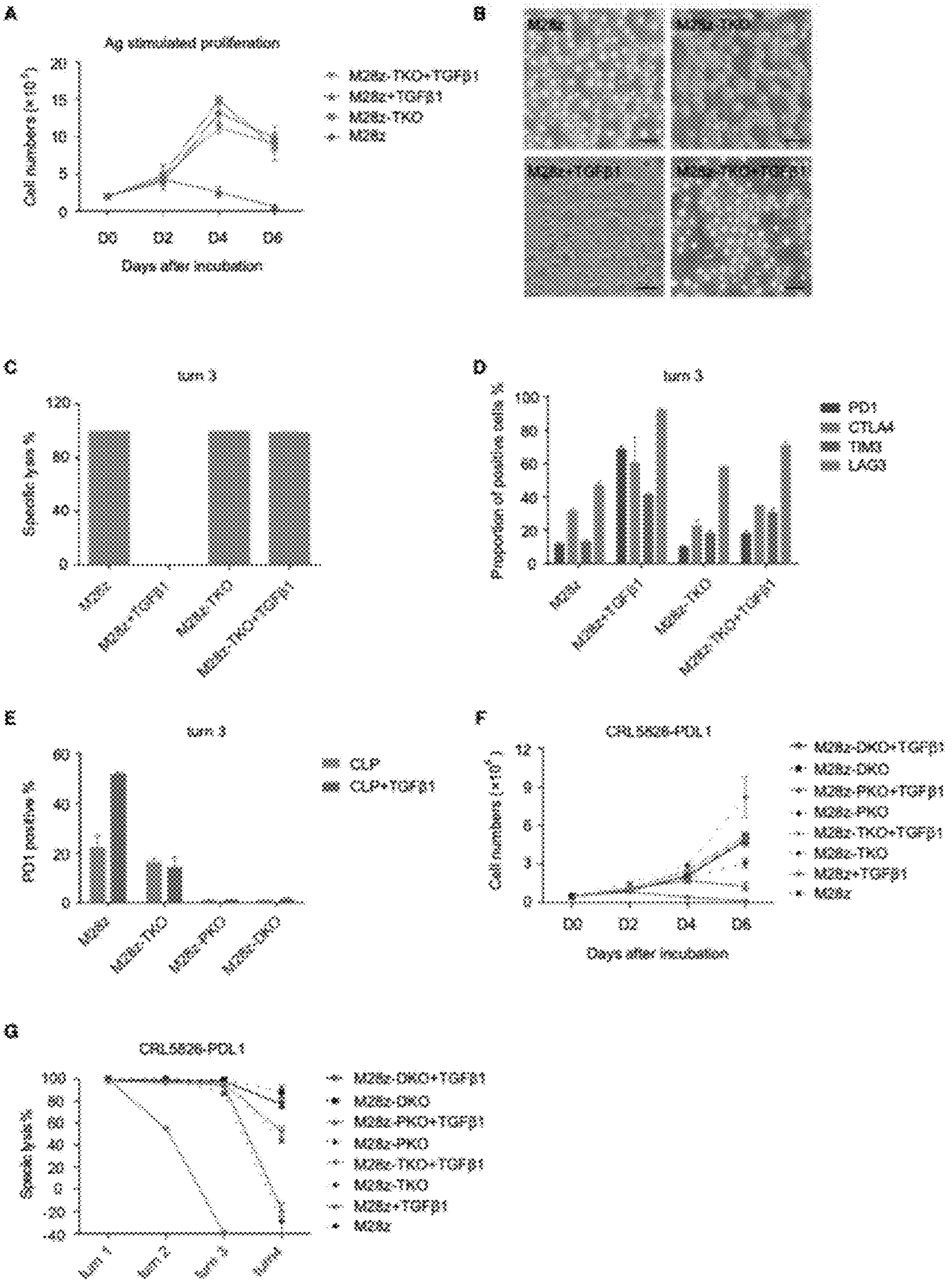
FIG. 47 shows that TGFβ1 accelerates CAR-T cell depletion by up-regulating PD1, while blocking both TGFB and PD1 signaling can further improve CAR-T resistance to inhibitory TME.

Continuous activation of T cell signaling leads to depletion. Depleted T cells have reduced proliferation capacity and effector function, and have immune checkpoint genes (such as PD1) overexpression. It was observed that the expression of PD1 mRNA in M28z increased significantly after the addition of TGFβ1 (FIG. 46), and multiple rounds of antigen stimulation assays were used to further investigate whether TGFβ1 accelerates CAR-T cell depletion. It was found that TGFβ1 significantly affected the proliferation of CAR-T cells after multiple tumor cell attacks. In the fourth challenge, almost all CAR-T cells died in the presence of TGFβ1, while the control cells survived well. Knockout of TGFBR II rendered CAR-T cells unresponsive to the TGFβ1 effect, resulting in survival similar to that of the control group (FIGS. 47A and 47B). In the presence of TGFβ1, the tumor lytic activity of CAR-T cells decreased to zero after two challenges, while M28z-TKO (TGFBR II KO) cells remained active (FIG. 47C). Therefore, after three rounds of tumor challenge, the addition of TGFβ1 significantly increased the expression of PD-1 in CAR-T cells, and knockout of TGFBR II reduced this effect. In contrast, the expression of TIM3, LAG3 and CTLA4 had a weaker response to TGFβ1, further indicating that PD1 is the main target induced by TGFβ1-driven CAR-T depletion (FIG. 47D). It is worth noting that there are still a significant number of PD1-expressing cells in M28z-TKO, indicating that although they do not respond to TGFβ1 signaling, they still tend to be inhibited by the corresponding ligands in the TME (tumor microenvironment).

In order to evaluate how upregulation of PD1 contributes to the inhibition effect of TGFβ, PD1 KO (M28z-PKO) and PD1/TGFBR II double KO (M28z-DKO) CAR-T cells were generated, and PDL1 was also overexpressed to model a more inhibitory effect TME. Compared with the up-regulation of PD1 in M28z induced by TGFβ1, the expression of PD1 in M28z-PKO and -DKO cells decreased to a basal level, indicating that the gene editing is effective. In multiple tumor challenges, knocking out PD1 did improve CAR-T proliferation, but it was still worse than TKO and DKO (FIG. 47F). In the presence of TGFβ1 and PDL1 overexpression, the tumor lysis ability of M28z was reduced in the second round and completely lost in the third round. In the 3rd round, M28z-PKO was able to achieve more than 90% tumor lysis and lost its efficacy in the 4th round. In contrast, M28z-TKO was able to maintain about 60% of the tumor lysis ability in the 4th round (FIG. 47G). All these data show that the upregulation of PD1 partially contributes to the negative regulation of TGFβ. On the other hand, TGFβ signaling is only part of the reason for PD1 expression, because some TKO cells still express PD1 and are therefore inhibited by PDL1. DKO CAR-T cells have the best performance, eliminating about 90% of tumors in the 4th round (FIG. 47G), indicating that blocking of both TGFβ and PD1 signaling can further improve CAR-T resistance to inhibitory TME.

Figure 48:
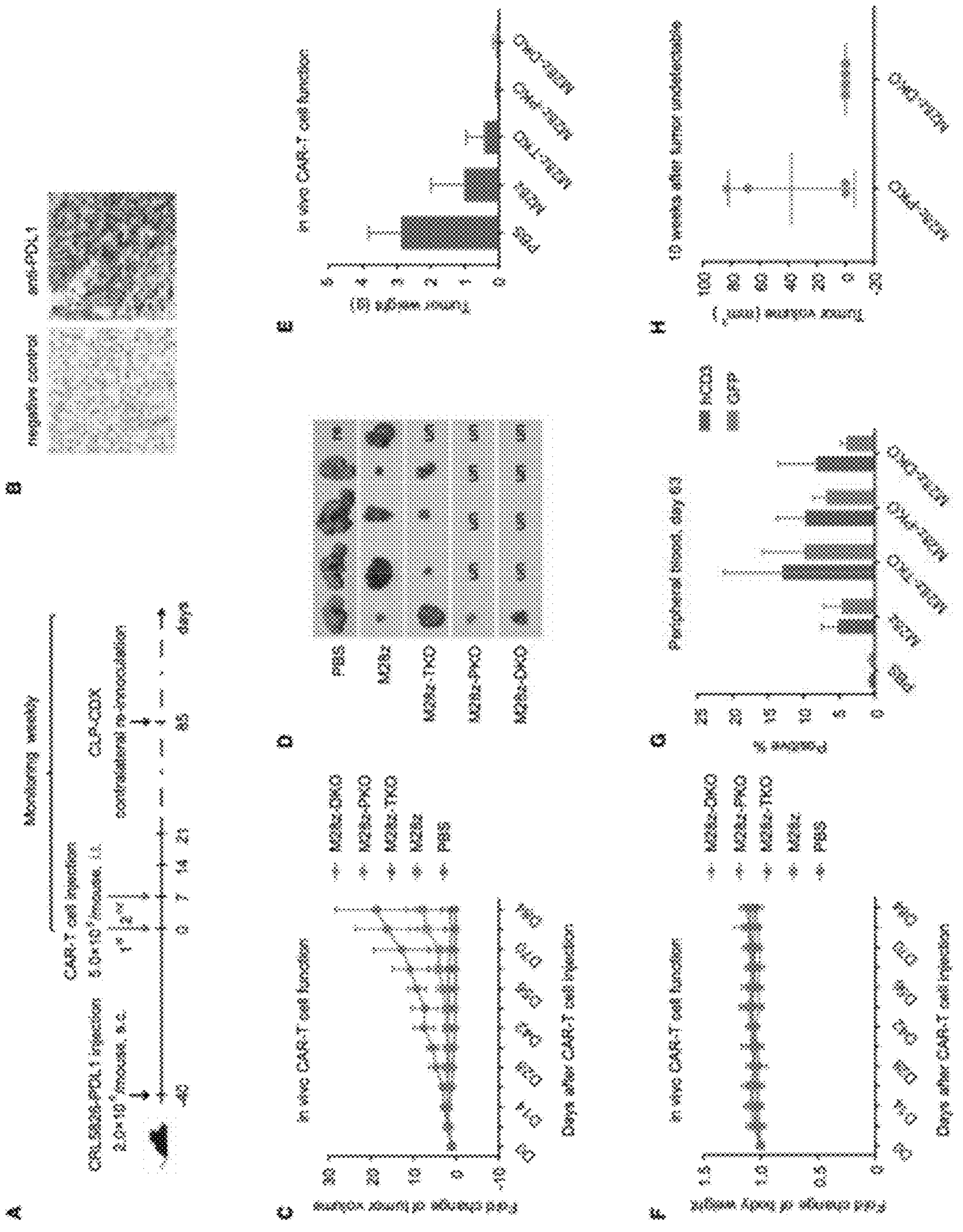
FIG. 48 shows that TGFBR II/PD1 dual-edited CAR-T cells have a better tumor elimination effect on the CDX model with PDL1 overexpression.
Figure 48:
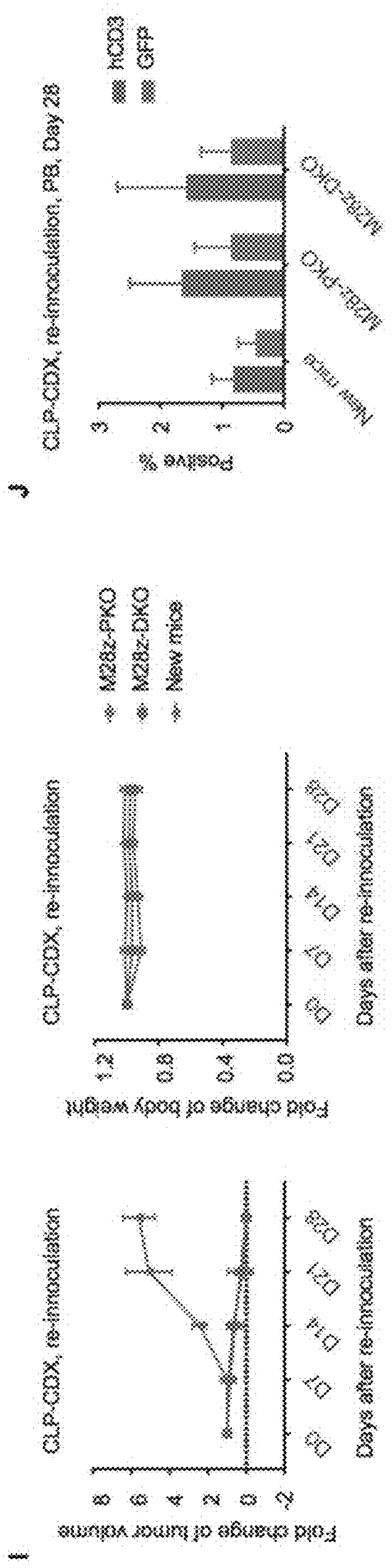

9.2 TGFBR II/PD1 Double-Edited CAR-T Cells have Better Tumor Elimination Effect on the CDX Model with PDL1 Overexpression After confirming the synergistic effect of TGFBR II and PD1 double KO to CAR-T cells against TGFβ1 and PDL1 double immunosuppression in vitro, the in vivo tumor elimination advantage of M28z-DKO in the CRL5826-PDL1 CDX model was further discussed (FIGS. 48A and 48B). Compared with the rapid increase in the PBS group and the slow increase in the M28z group, the tumor volume was controlled at a basic level, and 20% of the tumors were removed in the M28z-TKO group. However, at the end of the experiment, 80% of the tumors in the M28z-PKO and -DKO groups respectively disappeared completely (FIG. 48C). The same trend was detected in tumor size and tumor weight (FIGS. 48D and 48E). It is worth noting that no mice with GvHD symptoms were observed, and all mice maintained good body weight (FIG. 48F). Peripheral blood analysis showed that the proportion of hCD3 and GFP positive cells was low, and compared with the M28z group, they were increased but not significantly increased in the edited CAR-T cell treatment group (FIG. 48G).

Considering the possibility that the tumor burden is not enough to show the elimination advantage of M28z-DKO, in the M28z-PKO and -DKO groups, the tumor-removed mice were re-inoculated with the same CDX on the contralateral side. Compared with the rapid growth in the control group, tumors were eradicated again 28 days after re-inoculation in the M28z-PKO and -DKO groups (FIG. 48I, left panel). At the same time, no mice developed GvHD symptoms and maintained good body weight (FIG. 48I, right panel), and the ratio of hCD3 and GFP positive cells was only about 2% (FIG. 48J). However, after elimination of the contralateral reinoculated tumor, 50% of the primary tumor recurred in the M28z-PKO group 10 weeks after eradication (FIG. 48H). These data indicate that M28z-DKO has the advantage of long-lasting tumor elimination ability in vivo, which is consistent with its better anti-depletion ability in vitro.

The experimental results indicate that the CAR-T cells in which one or more inhibitory proteins of the present invention have been knocked out have the comparable effect as non-knocked out CAR-T cells at high-effector: target ratios. Unexpectedly, the knock-out CAR-T cells of the present invention are superior to non-knockout CAR-T cells under low-effector: target ratio and longer term action. This is particularly beneficial for reducing costs, reducing preparation time, and reducing side effects caused by high-dose administration.

What we claim is:

1. A method for preparing a modified T cell, comprising a step of eliminating the expression of at least one inhibitory protein in the T cell and a step of eliminating the expression of PD1 in the T cell, wherein the inhibitory protein is a T cell surface inhibitory receptor and/or a T cell exhaustion-related protein, wherein the inhibitory protein is a TGFBRII receptor, wherein said elimination of at least one inhibitory protein and elimination of the expression of PD1 is achieved by antisense RNA, antagomir, siRNA, shRNA, meganuclease, zinc finger nuclease, transcription activator-like effector nuclease, or a CRISPR system, wherein said T cell is a T cell comprising a chimeric antigen receptor (CAR).

2. The method of claim 1, wherein said CRISPR system is a CRISPR/Cas9 system.

3. The method of claim 2, wherein said CRISPR/Cas9 system targets one or more of the nucleotide sequences in the cells selected from the group consisting of SEQ ID NOs: 28-31.

4. The method of claim 1, wherein the CAR comprises an antigen binding domain against a tumor associated antigen.

5. The method of claim 4, wherein the tumor associated antigen is selected from the group consisting of CD16, CD64, CD78, CD96, CLL1, CD116, CD117, CD71, CD45, CD71, CD123, CD138, ErbB2, carcinoembryonic antigen (CEA), epithelial cell adhesion molecule (EpCAM), epidermal growth factor receptor (EGFR), EGFR variant III (EGFRvIII), CD19, CD20, CD30, CD40, disialylganglioside GD2, ductal epithelial mucin, gp36, TAG-72, glycosphingolipid, glioma-related antigens, p-human chorionic gonadotropin, a-fetoglobulin (AFP), lectin-responsive AFP, thyroglobulin, RAGE-1, MN-CA IX, human telomerase reverse transcriptase, RU1, RU2, intestinal carboxyl esterase, mut hsp70-2, M-CSF, prostase, prostate specific antigen (PSA), PAP, NY-ESO-1, LAGA-1a, p53, Prostein, PSMA, survival and telomerase, prostate cancer tumor antigen-1 (PCTA-1), MAGE, ELF2M, neutrophil elastase, ephrin B2, CD22, insulin growth factor (IGF)-I, IGF-II, IGF-I receptor, mesothelin, major histocompatibility complex (MHC) molecules that present tumor-specific peptide epitopes, 5T4, ROR1, Nkp30, NKG2D, tumor stromal antigen, fibronectin extra domain A (EDA) and extra domain B (EDB), tenascin-C A1 domain (TnC A1), fibroblast-associated protein (fap), CD3, CD4, CD8, CD24, CD25, CD33, CD34, CD133, CD138, Foxp3, B7-1, B7-2, GM-CSF, cytokine receptor, endothelial factor, BCMA, TNFRSF17, SLAMF7, GPRC5D, FKBP11, KAMP3, ITGA8 and FCRL5.

6. The method of claim 4, wherein the antigen binding domain is selected from the group consisting of a monoclonal antibody, a synthetic antibody, a human antibody, a humanized antibody, a single domain antibody, an antibody single-chain variable region, and an antigen binding fragment thereof.

7. The method of claim 1, wherein the CAR comprises a scFv against mesothelin, a CD8 hinge region, a CD28 transmembrane domain, a CD28 costimulatory domain, and a CD37 signal transduction domain.

8. The method of claim 7, wherein the CAR comprises an amino acid sequence set forth in SEQ ID NO:27.

9. A modified T cell prepared by the method of claim 1.

* * * * *

SEQUENCE LISTING

```
<160> NUMBER OF SEQ ID NOS: 31

<210> SEQ ID NO 1
<211> LENGTH: 20
<212> TYPE: DNA
<213> ORGANISM: Artificial Sequence
<220> FEATURE:
<223> OTHER INFORMATION: TIGIT target sequence

<400> SEQUENCE: 1

tcctcctgat ctgggcccag                                                20


<210> SEQ ID NO 2
<211> LENGTH: 20
<212> TYPE: DNA
<213> ORGANISM: Artificial Sequence
<220> FEATURE:
<223> OTHER INFORMATION: BTLA target sequence

<400> SEQUENCE: 2

aagacattgc ctgccatgct                                                20


<210> SEQ ID NO 3
<211> LENGTH: 20
<212> TYPE: DNA
<213> ORGANISM: Artificial Sequence
<220> FEATURE:
<223> OTHER INFORMATION: CD160 target sequence

<400> SEQUENCE: 3

tgcaggatgc tgttggaacc                                                20
```

<210> SEQ ID NO 4
<211> LENGTH: 20
<212> TYPE: DNA
<213> ORGANISM: Artificial Sequence
<220> FEATURE:
<223> OTHER INFORMATION: 2B4 target sequence

<400> SEQUENCE: 4
gatacacctt gaggagcagg 20

<210> SEQ ID NO 5
<211> LENGTH: 20
<212> TYPE: DNA
<213> ORGANISM: Artificial Sequence
<220> FEATURE:
<223> OTHER INFORMATION: CD200R target sequence

<400> SEQUENCE: 5
cctaggttag cagttctcca 20

<210> SEQ ID NO 6
<211> LENGTH: 20
<212> TYPE: DNA
<213> ORGANISM: Artificial Sequence
<220> FEATURE:
<223> OTHER INFORMATION: BATF target sequence

<400> SEQUENCE: 6
gctgtcggag ctgtgaggca 20

<210> SEQ ID NO 7
<211> LENGTH: 20
<212> TYPE: DNA
<213> ORGANISM: Artificial Sequence
<220> FEATURE:
<223> OTHER INFORMATION: GATA3 target sequence

<400> SEQUENCE: 7
ttccgtagta gggcgggacg 20

<210> SEQ ID NO 8
<211> LENGTH: 20
<212> TYPE: DNA
<213> ORGANISM: Artificial Sequence
<220> FEATURE:
<223> OTHER INFORMATION: IRF4 target sequence

<400> SEQUENCE: 8
ctgatcgacc agatcgacag 20

<210> SEQ ID NO 9
<211> LENGTH: 20
<212> TYPE: DNA
<213> ORGANISM: Artificial Sequence
<220> FEATURE:
<223> OTHER INFORMATION: RARA target sequence

<400> SEQUENCE: 9
ccattgaggt gcccgccccc 20

<210> SEQ ID NO 10
<211> LENGTH: 20
<212> TYPE: DNA
<213> ORGANISM: Artificial Sequence
<220> FEATURE:

<223> OTHER INFORMATION: A2AR target sequence

<400> SEQUENCE: 10
ctcctcggtg tacatcacgg 20

<210> SEQ ID NO 11
<211> LENGTH: 20
<212> TYPE: DNA
<213> ORGANISM: Artificial Sequence
<220> FEATURE:
<223> OTHER INFORMATION: IL10RA target sequence

<400> SEQUENCE: 11
gcgccgccag cagcactacg 20

<210> SEQ ID NO 12
<211> LENGTH: 20
<212> TYPE: DNA
<213> ORGANISM: Artificial Sequence
<220> FEATURE:
<223> OTHER INFORMATION: ADRB2 target sequence

<400> SEQUENCE: 12
caagaaggcg ctgccgttcc 20

<210> SEQ ID NO 13
<211> LENGTH: 20
<212> TYPE: DNA
<213> ORGANISM: Artificial Sequence
<220> FEATURE:
<223> OTHER INFORMATION: LAYN target sequence

<400> SEQUENCE: 13
tagcgcggtt cccggcctca 20

<210> SEQ ID NO 14
<211> LENGTH: 20
<212> TYPE: DNA
<213> ORGANISM: Artificial Sequence
<220> FEATURE:
<223> OTHER INFORMATION: MYO7A target sequence

<400> SEQUENCE: 14
agcttcacca ccgccccgat 20

<210> SEQ ID NO 15
<211> LENGTH: 20
<212> TYPE: DNA
<213> ORGANISM: Artificial Sequence
<220> FEATURE:
<223> OTHER INFORMATION: PHLDA1 target sequence

<400> SEQUENCE: 15
ggcgcacgcc tcattaactt 20

<210> SEQ ID NO 16
<211> LENGTH: 20
<212> TYPE: DNA
<213> ORGANISM: Artificial Sequence
<220> FEATURE:
<223> OTHER INFORMATION: RGS1 target sequence

<400> SEQUENCE: 16
gtcgtctaga agtgaatgag 20

<210> SEQ ID NO 17
<211> LENGTH: 20
<212> TYPE: DNA
<213> ORGANISM: Artificial Sequence
<220> FEATURE:
<223> OTHER INFORMATION: RGS2 target sequence

<400> SEQUENCE: 17
agacccatgg acaagagcgc 20

<210> SEQ ID NO 18
<211> LENGTH: 20
<212> TYPE: DNA
<213> ORGANISM: Artificial Sequence
<220> FEATURE:
<223> OTHER INFORMATION: SHP1 target sequence

<400> SEQUENCE: 18
tcggcccagt cgcaagaacc 20

<210> SEQ ID NO 19
<211> LENGTH: 20
<212> TYPE: DNA
<213> ORGANISM: Artificial Sequence
<220> FEATURE:
<223> OTHER INFORMATION: DGKa target sequence

<400> SEQUENCE: 19
gttgcttgga cctcttcaga 20

<210> SEQ ID NO 20
<211> LENGTH: 20
<212> TYPE: DNA
<213> ORGANISM: Artificial Sequence
<220> FEATURE:
<223> OTHER INFORMATION: Fas target sequence

<400> SEQUENCE: 20
gagggtccag atgcccagca 20

<210> SEQ ID NO 21
<211> LENGTH: 20
<212> TYPE: DNA
<213> ORGANISM: Artificial Sequence
<220> FEATURE:
<223> OTHER INFORMATION: FasL target sequence

<400> SEQUENCE: 21
gtaattgaag ggctgctgca 20

<210> SEQ ID NO 22
<211> LENGTH: 258
<212> TYPE: PRT
<213> ORGANISM: Artificial Sequence
<220> FEATURE:
<223> OTHER INFORMATION: scFv(P4) against mesothelin

<400> SEQUENCE: 22

Gln Val Gln Leu Gln Gln Ser Gly Pro Gly Leu Val Thr Pro Ser Gln
1 5 10 15

Thr Leu Ser Leu Thr Cys Ala Ile Ser Gly Asp Ser Val Ser Ser Asn
20 25 30

Ser Ala Thr Trp Asn Trp Ile Arg Gln Ser Pro Ser Arg Gly Leu Glu
35 40 45

Trp Leu Gly Arg Thr Tyr Tyr Arg Ser Lys Trp Tyr Asn Asp Tyr Ala

```
    50                  55                  60

Val Ser Val Lys Ser Arg Met Ser Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Met Met Thr Tyr Tyr Tyr Gly Met Asp Val
            100                 105                 110

Trp Gly Gln Gly Thr Thr Val Thr Val Ser Ser Gly Ile Leu Gly Ser
        115                 120                 125

Gly Gly Gly Gly Ser Gly Gly Gly Gly Ser Gly Gly Gly Gly Ser Gln
    130                 135                 140

Pro Val Leu Thr Gln Ser Ser Ser Leu Ser Ala Ser Pro Gly Ala Ser
145                 150                 155                 160

Ala Ser Leu Thr Cys Thr Leu Arg Ser Gly Ile Asn Val Gly Pro Tyr
                165                 170                 175

Arg Ile Tyr Trp Tyr Gln Gln Lys Pro Gly Ser Pro Pro Gln Tyr Leu
            180                 185                 190

Leu Asn Tyr Lys Ser Asp Ser Asp Lys Gln Gln Gly Ser Gly Val Pro
        195                 200                 205

Ser Arg Phe Ser Gly Ser Lys Asp Ala Ser Ala Asn Ala Gly Val Leu
    210                 215                 220

Leu Ile Ser Gly Leu Arg Ser Glu Asp Glu Ala Asp Tyr Tyr Cys Met
225                 230                 235                 240

Ile Trp His Ser Ser Ala Ala Val Phe Gly Gly Gly Thr Gln Leu Thr
                245                 250                 255

Val Leu


<210> SEQ ID NO 23
<211> LENGTH: 27
<212> TYPE: PRT
<213> ORGANISM: Artificial Sequence
<220> FEATURE:
<223> OTHER INFORMATION: CD28 transmembrane domain

<400> SEQUENCE: 23

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25


<210> SEQ ID NO 24
<211> LENGTH: 45
<212> TYPE: PRT
<213> ORGANISM: Artificial Sequence
<220> FEATURE:
<223> OTHER INFORMATION: CD8 hinge region

<400> SEQUENCE: 24

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45


<210> SEQ ID NO 25
<211> LENGTH: 112
<212> TYPE: PRT
```

<213> ORGANISM: Artificial Sequence
<220> FEATURE:
<223> OTHER INFORMATION: CD3?? signal transduction domain

<400> SEQUENCE: 25

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 26
<211> LENGTH: 41
<212> TYPE: PRT
<213> ORGANISM: Artificial Sequence
<220> FEATURE:
<223> OTHER INFORMATION: CD28 costimulatory domain

<400> SEQUENCE: 26

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 27
<211> LENGTH: 483
<212> TYPE: PRT
<213> ORGANISM: Artificial Sequence
<220> FEATURE:
<223> OTHER INFORMATION: P4-CAR

<400> SEQUENCE: 27

```
Gln Val Gln Leu Gln Gln Ser Gly Pro Gly Leu Val Thr Pro Ser Gln
1               5                   10                  15

Thr Leu Ser Leu Thr Cys Ala Ile Ser Gly Asp Ser Val Ser Ser Asn
            20                  25                  30

Ser Ala Thr Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Met Ser Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Met Met Thr Tyr Tyr Tyr Gly Met Asp Val
            100                 105                 110

Trp Gly Gln Gly Thr Thr Val Thr Val Ser Ser Gly Ile Leu Gly Ser
        115                 120                 125
```

-continued

```
Gly Gly Gly Gly Ser Gly Gly Gly Gly Ser Gly Gly Gly Gly Ser Gln
    130                 135                 140

Pro Val Leu Thr Gln Ser Ser Ser Leu Ser Ala Ser Pro Gly Ala Ser
145                 150                 155                 160

Ala Ser Leu Thr Cys Thr Leu Arg Ser Gly Ile Asn Val Gly Pro Tyr
                165                 170                 175

Arg Ile Tyr Trp Tyr Gln Gln Lys Pro Gly Ser Pro Pro Gln Tyr Leu
            180                 185                 190

Leu Asn Tyr Lys Ser Asp Ser Asp Lys Gln Gln Gly Ser Gly Val Pro
        195                 200                 205

Ser Arg Phe Ser Gly Ser Lys Asp Ala Ser Ala Asn Ala Gly Val Leu
    210                 215                 220

Leu Ile Ser Gly Leu Arg Ser Glu Asp Glu Ala Asp Tyr Tyr Cys Met
225                 230                 235                 240

Ile Trp His Ser Ser Ala Ala Val Phe Gly Gly Gly Thr Gln Leu Thr
                245                 250                 255

Val Leu Thr Thr Thr Pro Ala Pro Arg Pro Pro Thr Pro Ala Pro Thr
            260                 265                 270

Ile Ala Ser Gln Pro Leu Ser Leu Arg Pro Glu Ala Cys Arg Pro Ala
        275                 280                 285

Ala Gly Gly Ala Val His Thr Arg Gly Leu Asp Phe Ala Cys Asp Phe
    290                 295                 300

Trp Val Leu Val Val Val Gly Gly Val Leu Ala Cys Tyr Ser Leu Leu
305                 310                 315                 320

Val Thr Val Ala Phe Ile Ile Phe Trp Val Arg Ser Lys Arg Ser Arg
                325                 330                 335

Leu Leu His Ser Asp Tyr Met Asn Met Thr Pro Arg Arg Pro Gly Pro
            340                 345                 350

Thr Arg Lys His Tyr Gln Pro Tyr Ala Pro Pro Arg Asp Phe Ala Ala
        355                 360                 365

Tyr Arg Ser Arg Val Lys Phe Ser Arg Ser Ala Asp Ala Pro Ala Tyr
    370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg
```

<210> SEQ ID NO 28
<211> LENGTH: 20
<212> TYPE: DNA
<213> ORGANISM: Artificial Sequence
<220> FEATURE:
<223> OTHER INFORMATION: TGFBRII sgRNA-1 target sequence

<400> SEQUENCE: 28

-continued

```
tgctggcgat acgcgtccac                                                  20


<210> SEQ ID NO 29
<211> LENGTH: 20
<212> TYPE: DNA
<213> ORGANISM: Artificial Sequence
<220> FEATURE:
<223> OTHER INFORMATION: TGFBRII sgRNA-4 target sequence

<400> SEQUENCE: 29

ccatgggtcg ggggctgctc                                                  20


<210> SEQ ID NO 30
<211> LENGTH: 20
<212> TYPE: DNA
<213> ORGANISM: Artificial Sequence
<220> FEATURE:
<223> OTHER INFORMATION: TGFBRII sgRNA-5 target sequence

<400> SEQUENCE: 30

cgagcagcgg ggtctgccat                                                  20


<210> SEQ ID NO 31
<211> LENGTH: 20
<212> TYPE: DNA
<213> ORGANISM: Artificial Sequence
<220> FEATURE:
<223> OTHER INFORMATION: TGFBRII sgRNA-8 target sequence

<400> SEQUENCE: 31

cctgagcagc ccccgaccca                                                  20
```